(12) United States Patent
Pierson et al.

(10) Patent No.: US 11,990,230 B2
(45) Date of Patent: May 21, 2024

(54) MANAGEMENT OF MEDICAL EQUIPMENT AND RESPONDERS

(71) Applicant: ZOLL Medical Corporation, Chelmsford, MA (US)

(72) Inventors: John P. Pierson, Tewksbury, MA (US); Kristopher M. Edgell, Shreveport, LA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 307 days.

(21) Appl. No.: 17/621,411

(22) PCT Filed: Jul. 6, 2020

(86) PCT No.: PCT/US2020/070235
§ 371 (c)(1),
(2) Date: Dec. 21, 2021

(87) PCT Pub. No.: WO2021/007588
PCT Pub. Date: Jan. 14, 2021

(65) Prior Publication Data
US 2022/0359064 A1    Nov. 10, 2022

Related U.S. Application Data

(60) Provisional application No. 62/871,316, filed on Jul. 8, 2019.

(51) Int. Cl.
*G16H 40/20* (2018.01)
*G16H 40/40* (2018.01)

(52) U.S. Cl.
CPC ............. *G16H 40/20* (2018.01); *G16H 40/40* (2018.01)

(58) Field of Classification Search
CPC ...... G16H 40/20; G16H 40/40; G08B 25/005; G08B 25/006; G08B 25/016; H04W 4/02; H04W 4/90
See application file for complete search history.

(56) References Cited

U.S. PATENT DOCUMENTS 6,292,687 B1    9/2001    Lowell et al.
6,493,581 B2    12/2002   Russell
(Continued)

FOREIGN PATENT DOCUMENTS

EP    3236408    10/2017
JP    2017-044480    3/2017
(Continued)

OTHER PUBLICATIONS

US 8,639,774 B2, 01/2014, Gaines et al. (withdrawn)
(Continued)

*Primary Examiner* — Christopher B Tokarczyk
(74) *Attorney, Agent, or Firm* — Finch & Maloney PLLC

(57) ABSTRACT

A system for managing responders acquiring medical equipment and responding to an emergency medical event includes mobile devices associated with responders; a computer aided dispatch (CAD), and an equipment/responder management system communicatively coupled to the mobile devices and CAD and configured to receive an event location from the CAD, retrieve medical equipment locations from a database, receive responder locations from the mobile devices, send the event and equipment locations to a first mobile device, generate an activity log for the event including first responder status information based on the responder location, the event and medical equipment locations, send the activity log to the first mobile device, send the event location and the medical equipment locations to a second mobile device, update the activity log with second responder status information based on the responder, event (Continued)

and medical equipment locations, and send the activity log to the mobile devices.

24 Claims, 37 Drawing Sheets

(56) References Cited

U.S. PATENT DOCUMENTS

| | | |
|---|---|---|
| 6,747,556 B2 | 6/2004 | Medema et al. |
| 6,937,150 B2 | 8/2005 | Medema et al. |
| 7,048,185 B2 | 5/2006 | Hart |
| 7,510,526 B2 | 3/2009 | Merry et al. |
| 7,769,465 B2 | 8/2010 | Matos |
| 7,793,850 B1 | 9/2010 | Ho et al. |
| 8,095,403 B2 | 1/2012 | Price |
| 8,234,125 B2 | 7/2012 | Skocic |
| 8,300,922 B1 | 10/2012 | Garvey, III |
| 8,319,632 B1 | 11/2012 | Vaisnys et al. |
| 8,423,128 B2 | 4/2013 | Goto |
| 8,526,910 B2 | 9/2013 | Messerly |
| 8,565,871 B2 | 10/2013 | Tuysserkani |
| 8,636,670 B2 | 1/2014 | Ferren et al. |
| 8,725,254 B2 | 5/2014 | Freeman |
| 8,818,522 B2 | 8/2014 | Mass et al. |
| 8,880,168 B2 | 11/2014 | Pearce et al. |
| 8,923,805 B2 | 12/2014 | Single |
| 8,981,927 B2 | 3/2015 | McSheffrey |
| 8,996,393 B2 | 3/2015 | Sobie |
| 9,026,147 B2 | 5/2015 | Galvin et al. |
| 9,035,787 B2 | 5/2015 | Bongberg et al. |
| 9,220,912 B2 | 12/2015 | Elghazzawi |
| 9,232,040 B2 | 1/2016 | Barash et al. |
| 9,269,251 B2 | 2/2016 | Lalonde et al. |
| 9,289,621 B2 | 3/2016 | Aoyama et al. |
| 9,301,132 B2 | 3/2016 | Ashley et al. |
| 9,307,383 B1 | 4/2016 | Patrick |
| 9,324,120 B2 | 4/2016 | Braun |
| 9,342,976 B2 | 5/2016 | Pfeffer |
| 9,364,682 B2 | 6/2016 | Peterson et al. |
| 9,482,739 B2 | 11/2016 | Mole et al. |
| 9,495,511 B2 | 11/2016 | Harrington et al. |
| 9,498,152 B2 | 11/2016 | Bowers |
| 9,594,875 B2 | 3/2017 | Arrizza et al. |
| 9,619,767 B2 | 4/2017 | Braun |
| 9,628,946 B2 | 4/2017 | Elghazzawi |
| 9,703,931 B2 | 7/2017 | Hinkel |
| 9,769,610 B1 | 9/2017 | Gordon et al. |
| 9,775,520 B2 | 10/2017 | Tran |
| 9,847,030 B2 | 12/2017 | Kadobayashi et al. |
| 9,872,998 B2 | 1/2018 | Aoyama et al. |
| 9,897,459 B2 | 2/2018 | Johnson |
| 9,928,478 B2 | 3/2018 | Ragusky et al. |
| 9,986,404 B2 | 5/2018 | Mehta et al. |
| 10,035,023 B2 | 7/2018 | Das |
| 10,044,857 B2 | 8/2018 | Philbin |
| 10,058,709 B2 | 8/2018 | Tilton, Jr. |
| 10,090,716 B2 | 10/2018 | Stever et al. |
| 10,092,767 B1 | 10/2018 | Newton et al. |
| 10,099,061 B2 | 10/2018 | Buchanan |
| 10,178,534 B2 | 1/2019 | Barash et al. |
| 10,298,072 B2 | 5/2019 | Stever et al. |
| 10,449,380 B2 | 10/2019 | Andrews |
| 10,517,479 B2 | 12/2019 | Tran |
| 10,701,542 B2 | 6/2020 | Martin et al. |
| 10,769,741 B2 | 9/2020 | Braun et al. |
| 10,773,091 B2 | 9/2020 | Andrews et al. |
| 10,841,775 B2 | 11/2020 | Barash et al. |
| 10,903,675 B2 | 1/2021 | Beyer et al. |
| 11,077,311 B2 | 8/2021 | Beyer et al. |
| 11,097,121 B2 | 8/2021 | Beyer et al. |
| 2003/0069648 A1 | 4/2003 | Douglas et al. |
| 2003/0149759 A1 | 8/2003 | Hetherington et al. |
| 2004/0049233 A1 | 3/2004 | Edwards |
| 2006/0030891 A1 | 2/2006 | Saltzstein et al. |
| 2006/0041278 A1 | 2/2006 | Cohen et al. |
| 2006/0149321 A1 | 7/2006 | Merry et al. |
| 2006/0149322 A1 | 7/2006 | Merry et al. |
| 2007/0174438 A9 | 7/2007 | Johnson et al. |
| 2007/0270909 A1 | 11/2007 | Saketkhou |
| 2008/0014869 A1 | 1/2008 | Demirbasa et al. |
| 2008/0250166 A1 | 10/2008 | Edwards |
| 2009/0149894 A1 | 6/2009 | Merry et al. |
| 2010/0017471 A1 | 1/2010 | Brown et al. |
| 2010/0286490 A1 | 11/2010 | Koverzin |
| 2011/0071880 A1 | 3/2011 | Spector |
| 2011/0145191 A1* | 6/2011 | Anderson ............... G06F 16/27 709/224 |
| 2012/0218102 A1 | 8/2012 | Bivens et al. |
| 2013/0012151 A1 | 1/2013 | Hankins |
| 2013/0040600 A1 | 2/2013 | Reitnour et al. |
| 2013/0087609 A1 | 4/2013 | Nichol et al. |
| 2013/0281818 A1 | 10/2013 | Vija et al. |
| 2014/0002241 A1 | 1/2014 | Elghazzawi |
| 2014/0236615 A1 | 8/2014 | Ragusky et al. |
| 2015/0163765 A1 | 6/2015 | Hobbs et al. |
| 2015/0173843 A1 | 6/2015 | Maughan et al. |
| 2015/0289122 A1* | 10/2015 | Friesen ................ H04W 4/90 455/404.2 |
| 2016/0100302 A1* | 4/2016 | Barash ............... G08B 21/0211 455/404.2 |
| 2016/0210581 A1 | 7/2016 | Braun |
| 2016/0213942 A1 | 7/2016 | Elghazzawi et al. |
| 2016/0328950 A1 | 11/2016 | Pelletier et al. |
| 2017/0003141 A1 | 1/2017 | Voeller et al. |
| 2017/0172424 A1 | 6/2017 | Eggers et al. |
| 2017/0173460 A1 | 6/2017 | Leu |
| 2017/0367927 A1 | 12/2017 | Cervantes |
| 2018/0369598 A1 | 12/2018 | Newton et al. |
| 2019/0099608 A1 | 4/2019 | Elghazzawi et al. |
| 2019/0117983 A1 | 4/2019 | Andrews et al. |
| 2019/0361437 A1* | 11/2019 | Wilson .................. G06F 40/58 |
| 2021/0074417 A1 | 3/2021 | Pierson et al. |

FOREIGN PATENT DOCUMENTS

| | | |
|---|---|---|
| WO | 20070058835 | 5/2007 |
| WO | 20070089225 | 8/2007 |
| WO | 20090034506 | 3/2009 |
| WO | 20090136259 | 11/2009 |
| WO | 20130149982 | 10/2013 |
| WO | 20170162627 | 9/2017 |
| WO | 20170167708 | 10/2017 |

OTHER PUBLICATIONS

Kosuke et al. ("An Effective Support System of Emergency Medical Services With Tablet Computers", JMIR Mhealth Uhealth 2015; 3(1):e23) (Year: 2015).*

* cited by examiner

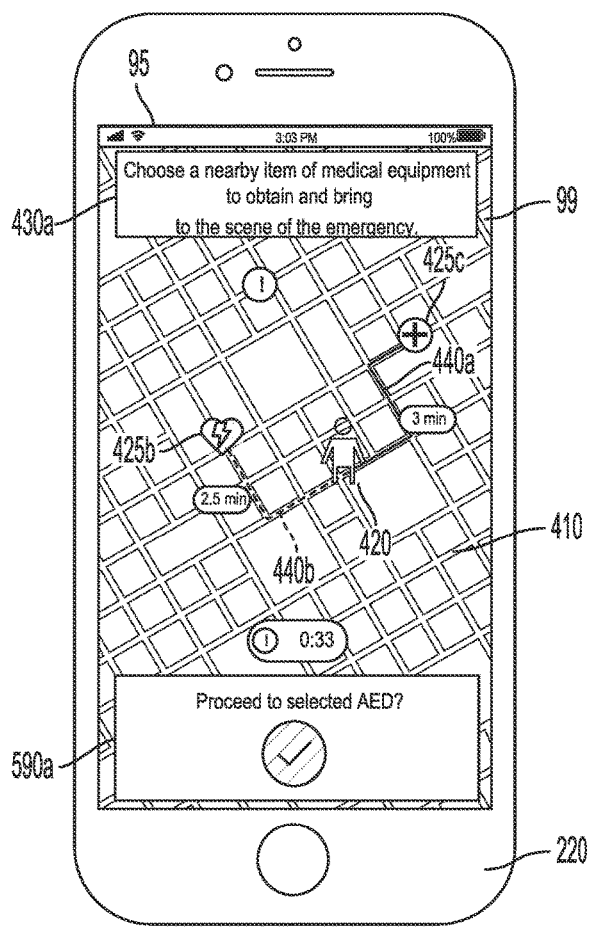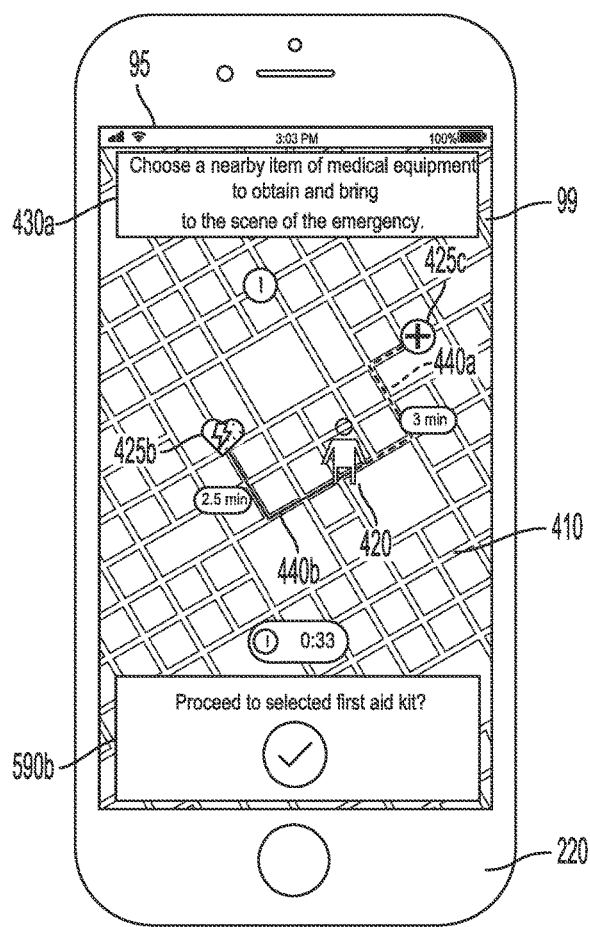
FIG. 5A
FIG. 5B

| Responder | Time with medical equipment | Time without medical equipment | Equipment |
|---|---|---|---|
| ▷ 2910 | 6 min | ▷ 2 min | 2921 |
| ▷ 2912 | ▷ 4 min | 3 min | ▷ 2922 |
| 2914 | 10 min | 8 min | 2923 |

MANAGEMENT OF MEDICAL EQUIPMENT AND RESPONDERS

CROSS-REFERENCE TO RELATED APPLICATIONS

This application is a United States National Phase entry under 35 U.S.C. § 371 of International Application No. PCT/US2020/070235, filed Jul. 6, 2020, which claims benefit under 35 U.S.C. § 119(e) to U.S. Provisional Application Ser. No. 62/871,316, filed on Jul. 8, 2019. All subject matter set forth in the above referenced applications is hereby incorporated by reference in its entirety into the present application as if fully set forth herein.

BACKGROUND

Emergency health events such as cardiac arrest, trauma, drug overdose, chemical exposure, etc. may kill or cause permanent injury to victims of these events. A fast and competent response to these events may be essential to a positive outcome. For example, the chance of surviving a cardiac arrest falls by ten percent for every minute in delaying effective treatment.

Emergency events are usually responded to by personnel associated with an emergency medical service (EMS) organization, for example, an ambulance crew or a fire crew. However, these EMS personnel are generally not on the scene at the time of the emergency health event. During the time it takes for the EMS personnel to arrive at the scene of the event, lay persons not associated with an EMS organization or not on duty with that organization may be located closer to the event. The proximity of these lay persons to the event may enable them to function as first responders that provide potentially life-saving care until the arrival of the EMS personnel.

Access to appropriate and publicly available medical equipment may enable these lay responders to provide the potentially life-saving care. For example, automated external defibrillators (AEDs) are generally made publicly accessible in order to reduce the response time to sudden cardiac arrest. Survival rates for victims of sudden cardiac arrest are typically reduced by ten percent for every minute of delay in providing resuscitative care. Therefore, timely defibrillation may be crucial for survival of the victims. As AEDs are used infrequently, routine monitoring of operational status along with inspections and maintenance may be necessary to ensure that AEDs placed in publicly accessible spaces are in working order. Similarly, routine monitoring along with inspections and maintenance of other types of medical equipment, including emergency equipment, may be necessary to ensure this equipment is in working order when needed for a response to the emergency health event.

SUMMARY

An example of a computer-implemented method for managing medical equipment and responders includes providing emergency event information and medical equipment location information to a first computing device associated with a first registered responder, the emergency event information including a location of an emergency event, receiving a selection of at least one first item of registered medical equipment via the first computing device and based on the medical equipment location information, determining responder status information for the first registered responder based on a current first responder location and at least one of the selected at least one first item of registered medical equipment and the location of the emergency event, and providing an activity log to the first computing device associated with the first registered responder, the activity log including an indication of the selected at least one first item of registered medical equipment, and the responder status information.

Implementations of one or more of the computer-implemented methods described herein may include one or more of the following features. The responder status information may include a navigation status for the first registered responder. The navigation status may include one of: en route to the selected at least one first item of registered medical equipment, arrived at the selected at least one first item of registered medical equipment, en route to the emergency event, and arrived at the emergency event. The responder status information may include an equipment acquisition status. The equipment acquisition status may include one of: acquired the selected at least one first item of medical equipment and proceeding to the emergency event without acquiring any medical equipment. One or more of the methods may include identifying the selected at least one first item of medical equipment based on a touch screen gesture on an interactive map. The first computing device may include a touch screen configured to provide the interactive map. The interactive map may include selectable location indicators for registered medical equipment. The selectable location indicators may be configured to capture the touch screen gesture indicative of an equipment selection by the first registered responder. One or more of the methods may include prompting the first registered responder to confirm acquisition of the selected at least one first item of medical equipment via the touch screen. One or more of the methods may include providing an emergency assistance request to the first computing device, receiving an acceptance of the emergency assistance request, providing the emergency event information and the medical equipment location information to the first computing device in response to receiving the acceptance of the emergency assistance request from the first computing device, automatically tracking the location of the first computing device in response to the acceptance of the emergency assistance request, and providing the tracked location of the first computing device on the interactive map. One or more of the methods may include providing the emergency event information to a second computing device associated with a second registered responder, determining the responder status information for the second registered responder based at least in part on a current second responder location, providing the activity log to the second computing device associated with the second registered responder, and updating the activity log provided to the first computing device and to the second computing device to include the responder status information for the first registered responder and for the second registered responder. One or more of the methods may include providing the medical equipment location information to the second computing device, capturing a selection of at least one second item of registered medical equipment via the second computing device, determining the responder status information for the second registered responder based on the selected at least one second item of registered medical equipment, and updating the activity log provided to the first computing device and to the second computing device to include an indication of the selected at least one second item of registered medical equipment. One or more of the methods may include displaying a timer with the activity log. The timer may indicate an elapsed time between a current time and a time of receipt of the emergency event information from an emergency dispatch service. One or more of the methods may include automatically updating the activity log based on an update to the responder status information. The activity log may include a timestamp for the responder status information. The responder status information may include current status information and historical status information. One or more of the methods may include providing the location of the emergency event to a plurality of computing devices included in a responder database, receiving an availability indication from each of one or more computing devices that the respective computing device has self-determined itself to be located within a vicinity of the location of the emergency event, the one or more computing devices including the first computing device, and providing an emergency assistance request to the first computing device in response to the received availability indication. The vicinity of the location of the emergency event may correspond to a distance of 0-400 meters from the emergency event. One or more of the methods may include filtering responder registration information in the responder database to identify a set of computing devices from the plurality of computing devices, the set of computing devices currently located within the vicinity of the location of the emergency event, and providing the location of the emergency event only to the set of computing devices. One or more of the methods may include filtering equipment registration information in an equipment database to identify a set of medical equipment located within a vicinity of the location of the emergency event. The provided medical equipment location information may only include the set of medical equipment located within the vicinity of the location of the emergency event. The vicinity of the location of the emergency event may correspond to a distance of 0-400 meters from the emergency event. The at least one first item of registered medical equipment may include one of a patient monitor, an external defibrillator, an automated external defibrillator, ventilation equipment, drug delivery equipment, a physiological sensor, a fire extinguisher, an oxygen tank, a drug overdose kit, a first aid kit, tourniquet equipment, eye wash equipment, an epinephrine auto-injector, and chemical exposure equipment.

An example of a computer-implemented method for managing medical equipment and responders includes providing emergency event information and medical equipment location information to a first computing device associated with a first registered responder, the emergency event information including a location of an emergency event, providing an interactive map to the first computing device associated with the first registered responder, the interactive map including an indicator of the location of the emergency event, an indicator of a current location of the first computing device, and selectable location indicators for a plurality of items of registered medical equipment located in a vicinity of the emergency event, and receiving a selection from the first computing device of at least one first item of registered medical equipment via the selectable location indicators on the interactive map.

Implementations of one or more of the computer-implemented methods described herein may include one or more of the following features. The selectable location indicators for the plurality of items of registered medical equipment may include graphic icons configured to capture a touch screen gesture. The one or more methods may include receiving equipment status information from one or more databases comprising medical equipment registration information, and selecting an appearance aspect of the selectable location indicators for the plurality of items of registered medical equipment based on the equipment status information. The appearance aspect may include one or more of a shape, size, and color. The equipment status information may include a time availability. The equipment status information may include an operational status. The one or more methods may include selecting a first color for a first operational status and a second color for a second operational status. The first operational status may include a verified operable condition of the selected at least one first item of registered medical equipment and the second operational status may include an unverified operable condition of the selected at least one first item of registered medical equipment. The one or more methods may include automatically changing an appearance of a selectable location indicator for the at least one first item of registered medical equipment to indicate the selection of the at least one first item of registered medical equipment. The one or more methods may include receiving a confirmation of acquisition of the selected at least one first item of registered medical equipment via the first computing device, and providing an indication on the interactive map that the at least one first item of registered medical equipment has been acquired by the first registered responder. The interactive map may include an information control. The one or more methods may include providing medical equipment information for the selected at least one first item of registered medical equipment in response to a selection of the information control. The one or more methods may include providing an emergency assistance request to the first computing device, receiving an acceptance of the emergency assistance request, providing the emergency event information and the medical equipment location information to the first computing device in response to receiving the acceptance of the emergency assistance request from the first computing device, automatically tracking the location of the first computing device in response to the acceptance of the emergency assistance request, and providing the tracked location of the first computing device on the interactive map. The one or more methods may include displaying a timer with the interactive map. The timer may indicate an elapsed time between a current time and a time of receipt of the emergency event information from an emergency dispatch service. The one or more methods may include changing a color of the timer based on the elapsed time. The one or more methods may include providing the location of the emergency event to a plurality of computing devices included in a responder database, receiving an availability indication from each of one or more computing devices that the respective computing device has self-determined itself to be located within the vicinity of the location of the emergency event, the one or more computing devices including the first computing device, and providing an emergency assistance request to the first computing device in response to the received availability indication. The vicinity of the location of the emergency event may correspond to a distance of 0-400 meters from the emergency event. The one or more methods may include filtering responder registration information in the responder database to identify a set of computing devices from the plurality of computing devices, the set of computing devices currently located within the vicinity of the location of the emergency event, and providing the location of the emergency event only to the set of computing devices. The one or more methods may include filtering equipment registration information in an equipment database to identify a set of medical equipment located within the vicinity of the location of the emergency event. The provided medical equipment location information may only include the set of medical equipment located within the vicinity of the location of the emergency event. The vicinity of the location of the emergency event may correspond to a distance of 0-400 meters from the emergency event. The one or more methods may include providing the emergency event information to a second computing device associated with a second registered responder, providing the interactive map to the second computing device associated with the second registered responder, the interactive map including an indicator of a current location of the second computing device, and receiving a selection from the second computing device of at least one second item of registered medical equipment via the selectable location indicators on the interactive map. The one or more methods may include providing the interactive map at the second computing device associated with the second registered responder and at the first computing device associated with the first registered responder. The interactive map may include indicators of updates to one or more of the navigation status for the first registered responder, a navigation status for the second registered responder, an equipment acquisition status for the first registered responder, and an equipment acquisition status for the second registered responder. The updates to one or more of the navigation status for the first registered responder and the navigation status for the second registered responder may include one or more of: updates to the current location of the first computing device, updates to the current location of the second computing device, an arrival by the first registered responder at the at least one first item of registered medical equipment, an arrival by the second registered responder at the at least one second item of registered medical equipment, an arrival by the first registered responder at the location of the emergency event, and an arrival by the second registered responder at the location of the emergency event. The at least one first item of registered medical equipment may include one of a patient monitor, an external defibrillator, an automated external defibrillator, ventilation equipment, drug delivery equipment, a physiological sensor, a fire extinguisher, an oxygen tank, a drug overdose kit, a first aid kit, tourniquet equipment, eye wash equipment, an epinephrine auto-injector, and chemical exposure equipment.

An example of a computer-implemented method for managing medical equipment and responders includes providing emergency event information and medical equipment location information to a first computing device associated with a first registered responder, the emergency event information including a location of an emergency event, providing an interactive map to the first computing device associated with the first registered responder, the interactive map including an indicator of the location of the emergency event, and location indicators for a plurality of items of registered medical equipment located in a vicinity of the emergency event, the location indicators corresponding to locations of the registered medical equipment, automatically tracking a current location of the first computing device, providing the tracked current location of the first computing device via the interactive map, determining a plurality of first estimated travel times between the tracked current location of the first computing device and the locations of the registered medical equipment, determining a plurality of second estimated travel times between the locations of the registered medical equipment and the location of the emergency event, providing a recommendation on the interactive map of an item of registered medical equipment for the first registered responder to select based at least in part on the plurality of first estimated travel times, and providing a recommendation on the interactive map of a first navigable route between the tracked current location of the first computing device and a location of the recommended item of registered medical equipment and of a second navigable route between the location of the recommended item of registered medical equipment and the location of the emergency event based at least in part on the plurality of first estimated travel times and the plurality of second estimated travel times.

Implementations of one or more of the computer-implemented methods described herein may include one or more of the following features. The plurality of items of registered medical equipment may include one or more of a patient monitor, an external defibrillator, an automated external defibrillator, ventilation equipment, drug delivery equipment, a physiological sensor, a fire extinguisher, an oxygen tank, a drug overdose kit, a first aid kit, tourniquet equipment, eye wash equipment, an epinephrine auto-injector, and chemical exposure equipment. The one or more methods may include indicating the recommended item of registered medical equipment on the interactive map with a first appearance aspect of a location indicator corresponding to the recommended item of registered medical equipment. The one or more methods may include providing a plurality of navigable routes between the tracked current location of the first computing device and the location of the recommended item of registered medical equipment, and indicating the recommendation on the interactive map of the first navigable route with a first appearance aspect of the first navigable route that differs from the plurality of navigable routes. The first appearance aspect of the first navigable route and the first appearance aspect of the location indicator may include one or more of shape, size, and color. The one or more methods may include receiving a user selection of one of the plurality of navigable routes other than the first navigable route, and indicating the user selected one of the plurality of navigable routes with a second appearance aspect that differs from the plurality of navigable routes. The one or more methods may include providing a plurality of navigable routes between the location of the recommended item of registered medical equipment and the location of the emergency event, and indicating the recommendation on the interactive map of the second navigable route with a first appearance aspect of the second navigable route that differs from the plurality of navigable routes. The one or more methods may include receiving a user selection of one of the plurality of navigable routes other than the second navigable route, and indicating the user selected one of the plurality of navigable routes with a second appearance aspect that differs from the plurality of navigable routes. The one or more methods may include receiving a confirmation of acquisition of the recommended item of registered medical equipment via the first computing device, and providing an indication on the interactive map that the recommended item of registered medical equipment has been acquired by the first registered responder. The one or more methods may include providing the plurality of navigable routes between the location of the recommended item of registered medical equipment and the location of the emergency event in response to the confirmation of acquisition of the recommended item of registered medical equipment. The one or more methods may include determining the plurality of first estimated travel times and the plurality of second estimated travel times based on an estimated average walking speed for a responder. The one or more methods may include prompting the first registered responder to indicate a mode of transport, and determining the plurality of first estimated travel times and the plurality of second estimated travel times based on the mode of transport. The mode of transport may include walking or driving. The one or more methods may include determining the plurality of first estimated travel times and the plurality of second estimated travel times based on an assumed speed associated with the mode of transport. The vicinity of the emergency event may include locations within a pre-determined distance from the emergency event based on the assumed speed associated with the mode of transport. The vicinity of the emergency event may include locations from which the location of the emergency event can be reached in a pre-determined amount of time based on the mode of transport. The one or more methods may include providing the plurality of items of registered medical equipment in an ordered list based at least in part on one or more of the plurality of first estimated travel times and the plurality of second estimated travel times. The one or more methods may include estimating an amount of time needed for the first registered responder to locate the recommended item of registered medical equipment once the first registered responder has arrived at a location of the recommended item of registered medical equipment, and determining at least one of the plurality of first estimated travel times and the plurality of second estimated travel times based on the amount of time needed for the first registered responder to locate the recommended item of registered medical equipment. The one or more methods may include determining the amount of time needed for the first registered responder to locate the recommended item of registered medical equipment based on an interior map comprising the location of the recommended item of registered medical equipment. The interior map may be a three-dimensional map that includes multiple stories and access routes comprising at least one of stairs and elevators. The first navigable route and the second navigable route may include a graphic representation of turn-by-turn directions. The one or more methods may include providing a directions control on the interactive map, and providing the turn-by-turn directions in a list format in response to a selection of the directions control.

An example of a computer-implemented method for managing medical equipment and responders includes providing an emergency assistance request to one or more computing devices, each computing device associated with a respective registered responder, the emergency assistance request including a location of an emergency event and an emergency response category, and medical equipment information for a plurality of items of registered medical equipment, the medical equipment information including location information and a type of medical equipment, receiving a selection of at least one item of registered medical equipment via a first computing device of the one or more computing devices and based on the location of the emergency event, the emergency response category, and the medical equipment information, tracking a location of the first computing device, and providing navigation instructions from the tracked location of the first computing device to a location of the at least one item of registered medical equipment and to the location of the emergency event.

Implementations of one or more of the computer-implemented methods described herein may include one or more of the following features. The type of medical equipment may include one or more of a trauma kit, a drug overdose kit, and a ventilator. The type of medical equipment may include one or more of a patient monitor, drug delivery equipment, a physiological sensor, a fire extinguisher, an oxygen source, tourniquet equipment, eye wash equipment, an epinephrine auto-injector, and chemical exposure equipment. The emergency response category may include trauma, drug overdose, cardiac arrest, respiratory distress. The one or more methods may include providing the location of the emergency event to a plurality of computing devices included in a responder database, receiving an availability indication from each of the one or more computing devices that a respective computing device has self-determined itself to be located within a vicinity of the location of the emergency event, receiving responder profile information for the respective registered responder associated with each of the one or more computing devices from a responder registration database, and providing the emergency assistance request to the one or more computing devices in response to the received availability indication and based on the responder profile information. The one or more methods may include recommending particular items of the plurality of items of registered medical equipment to one or more of the respective registered responders based on the responder profile information. The responder profile information may include responder training information. The responder training information may include a proficiency level for the emergency response category. The proficiency level for the emergency response category may include one or more of basic first aid for trauma, advanced first aid for trauma, lay rescuer for adult CPR, lay rescuer for pediatric CPR, professional rescuer for adult CPR, professional rescuer for pediatric CPR, lay rescuer for defibrillation, and professional rescuer for defibrillation. The one or more methods may include receiving the medical equipment information from an equipment registration database for the plurality of items of registered medical equipment for which the type of medical equipment corresponds to the emergency response category and for which the location may be in a vicinity of the location of the emergency event. The vicinity of the location of the emergency event may correspond to a distance traversed by a responder within a pre-determined response time based on the emergency response category. The pre-determined response time may be based on the emergency response category. The distance traversed by the responder within the pre-determined response time may depend on a mode of transport for the responder. The mode of transport may be walking or driving and the distance traversed by the responder within the pre-determined response time may be based on an assumed average speed for the mode of transport. The distance traversed by the responder may include a distance from a current location of the responder to the at least one item of registered medical equipment and a distance from the at least one item of registered medical equipment to the location of the emergency event. The distance traversed by the responder may include a distance from an entryway to a facility that houses the at least one item of registered medical equipment to a storage location of the at least one item of registered medical equipment. The pre-determined response time may be 1-4 minutes. The distance traversed by the responder may be 0-400 meters. The medical equipment information may include user support information. The user support information may indicate CPR prompting and/or CPR feedback provided by the at least one first item of registered medical equipment. The user support information may indicate a rescuer skill level corresponding to the one or more of the user prompting and the user feedback. The one or more methods may include providing the emergency assistance request to at least a second computing device associated with a second registered responder, and instructing the second registered responder via the second computing device to proceed to the location of the emergency event without selecting and/or acquiring any registered medical equipment.

An example of a computer-implemented method for managing medical equipment and responders includes receiving emergency event information for an emergency event from an emergency dispatch service, the emergency event information including a location of the emergency event, receiving EMS agency information from an EMS agency responding to the emergency event, selecting at least one registered responder and at least one item of registered medical equipment based on the EMS agency information and the location of the emergency event, and providing the location of the emergency event and medical equipment location information for the at least one item of registered medical equipment to a first computing device associated with the at least one registered responder.

Implementations of one or more of the computer-implemented methods described herein may include one or more of the following features. The one or more methods may include providing an activity log to the first computing device, the activity log including time stamped activity information for the at least one registered responder and for the EMS agency. The one or more methods may include providing an interactive map to the first computing device. The interactive map may include a location indicator for at least one dispatched vehicle from the EMS agency responding to the emergency event. The one or more methods may include tracking a current location of the at least one dispatched vehicle, tracking a current location of the first computing device, and updating the current locations of the at least one dispatched vehicle and the first computing device on the interactive map. The one or more methods may include providing an indication of an estimated time of arrival of personnel from the EMS agency at the emergency event. The one or more methods may include providing instructions from the EMS agency for the at least one registered responder to the first computing device. The one or more methods may include filtering responder registration information in a responder database to identify a set of computing devices from a plurality of computing devices in the responder registration information. The set of computing devices may be currently located closer to the emergency event than the EMS agency responding to the emergency event. The one or more methods may include providing the location of the emergency event only to the set of computing devices. The EMS agency information may include a recommendation of responder training and/or proficiency level for the at least one registered responder. The EMS agency information may include a recommendation of the at least one item of registered medical equipment. The one or more methods may include receiving a confirmation of acquisition of the at least one item of registered medical equipment via the first computing device, and sending the confirmation of acquisition of the at least one item of registered medical equipment to the EMS agency. The one or more methods may include receiving a notification from the EMS agency that at least one dispatched vehicle from the EMS agency arrived at the emergency event, and providing an end of event screen to the first computing device. The one or more methods may include providing the end of event screen to one or more second computing devices associated with one or more additional registered responders en route to the emergency event. The one or more methods may include receiving a patient care record from the EMS agency for the emergency event, appending the patient care record with stored management system information for the emergency event based on activities of the at least one registered responder, and sending the appended patient care record to the EMS agency. The one or more methods may include sending stored management system information for the emergency event to the EMS agency. The at least one item of registered medical equipment may include one of a patient monitor, an external defibrillator, an automated external defibrillator, ventilation equipment, drug delivery equipment, a physiological sensor, a fire extinguisher, an oxygen tank, a drug overdose kit, a first aid kit, tourniquet equipment, eye wash equipment, an epinephrine auto-injector, and chemical exposure equipment.

An example of a system for remote communications with mobile communication devices for managing responders acquiring medical equipment and responding to an emergency medical event includes a first mobile computing device associated with a first registered responder; a second mobile computing device associated with a second registered responder, a computer aided dispatch (CAD) system, and a medical equipment and responder management system communicatively coupled to the first and second mobile computing devices and to the CAD and the management system is configured to receive emergency medical event information from the CAD, the emergency medical event information including an emergency medical event location, retrieve medical equipment information stored in a medical equipment database, the medical equipment information including medical equipment locations, receive a current first responder location from the first mobile computing device, send the emergency medical event location and the medical equipment locations to the first mobile computing device, generate an activity log for the emergency medical event, the activity log including first responder status information based at least in part on the current first responder location, the emergency medical event location, and the medical equipment locations, send the activity log to the first mobile computing device, send the emergency medical event location and the medical equipment locations to the second mobile computing device, receive a current second responder location from the second mobile computing device, update the activity log with second responder status information based at least in part on the current second responder location, the emergency medical event location, and the medical equipment locations, and send the updated activity log to the first and the second mobile computing devices.

Implementations of one or more systems described herein may include one or more of the following features. The first and second responder status information may include time stamped activity information for the first and second registered responders. The activity log may include a timer that indicates an elapsed time between a current time and a time of receipt of the emergency medical event information from the CAD at the management system. The first and second responder status information may include a navigation status and an equipment acquisition status. The navigation status may include one of: (a) en route to an item of medical equipment in the medical equipment database, (b) arrived at the item of medical equipment in the medical equipment database, (c) en route to the emergency medical event, and (d) arrived at the emergency medical event. The equipment acquisition status may include one of: (a) acquired an item of medical equipment in the medical equipment database, and (b) proceeding to the emergency medical event without acquiring any medical equipment in the medical equipment database. The management system may be configured to retrieve registered responder information stored in a responder database, retrieve user selected tracking permission settings from the responder database for the first and second responders, automatically track locations for the first and second mobile computing devices in response to the user selected tracking permission settings, and update the first and second responder statuses in the activity log at the first and second mobile computing devices based on the automatically tracked locations. The management system may be configured to provide interactive map information at the first and second mobile computing devices, wherein the interactive map information may include the automatically tracked locations of the first and second mobile computing devices, the emergency medical event location, and the medical equipment location information. The management system may be configured to filter equipment registration information in the medical equipment database to identify a set of medical equipment located within a vicinity of the emergency medical event location, and send the medical equipment location information for only the set of medical equipment located within the vicinity of the emergency medical event location to the first mobile computing device. The vicinity of the emergency medical event location may correspond to a distance of 0-400 meters from the emergency medical event. The vicinity of the emergency medical event location may correspond to a distance within a predetermined travel time from the emergency medical event based on a speed associated with a responder mode of transport. The management system may be configured to estimate a plurality of first travel times for the first and second responders between the automatically tracked locations of the first and second mobile computing devices and the medical equipment locations, estimate a plurality of second travel times for the first and second responders between the medical equipment locations and the emergency medical event location, and send an equipment acquisition recommendation configured for display on the interactive map based at least in part on the plurality of first and second travel times. The management system may be configured to retrieve a mode of transport stored in the responder database for each of the first and second responders, and estimate the first and second travel times based on an estimated speed for the mode of transport, wherein the mode of transport includes walking or driving. The equipment acquisition recommendation may include an indication of a navigable routes between the emergency medical event location, the automatically tracked locations of the first and second mobile computing devices, and the medical equipment locations for a set of medical equipment located within a vicinity of the emergency medical event location. The navigable routes may include one or more of graphic or text representations of turn-by-turn directions. The management system may be configured to estimate the first and second travel times based on one or more interior maps corresponding to one or more facilities storing medical equipment in the medical equipment database. The one or more interior maps may be three-dimensional maps that include multiple stories and access routes including at least one of stairs and elevators. The estimated first and second travel times may account for a distance from a facility entryway to a medical equipment storage location. The management system may be configured to estimate a plurality of third travel times for the first and second responders between the automatically tracked locations of the first and second mobile computing devices and the emergency medical event location, rank the first and second responders according to the third travel times and a sum of the first and second travel times, select one of the first or second responders to acquire the medical equipment based on the rank, select another one of the first or second responders to proceed to the emergency medical event location without acquiring the medical equipment, and send instructions to the first and second mobile computing devices based on the selections. One or more of the activity log and the interactive map may include an indication of medical equipment acquisition by the first and/or second responder. The medical equipment database may include registration information for one or more of automated external defibrillators and trauma kits. The registration information may include equipment status information and the medical equipment information. The management system may be configured to send the location of the emergency medical event to a plurality of computing devices associated with registered responders and included in a responder database, receive availability indications from one or more computing devices, wherein the respective computing device has self-determined itself to be located within a vicinity of the location of the emergency medical event and wherein the one or more computing devices comprise the first and second mobile computing devices, and send the emergency medical event location to the first and second mobile computing devices in response to the received availability indications. The responder database may include responder training information indicative of a proficiency level for a category of emergency medical event. The management system may be configured to determine the category of the emergency medical event based on the emergency medical event information received from the CAD, and send the one or more computing devices the emergency medical event location based on the proficiency level of an associated responder and the category of the emergency medical event.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIGS. 5A and 5B show examples of equipment selection features provided at the interactive map by the software application.

DETAILED DESCRIPTION

Figure 1:
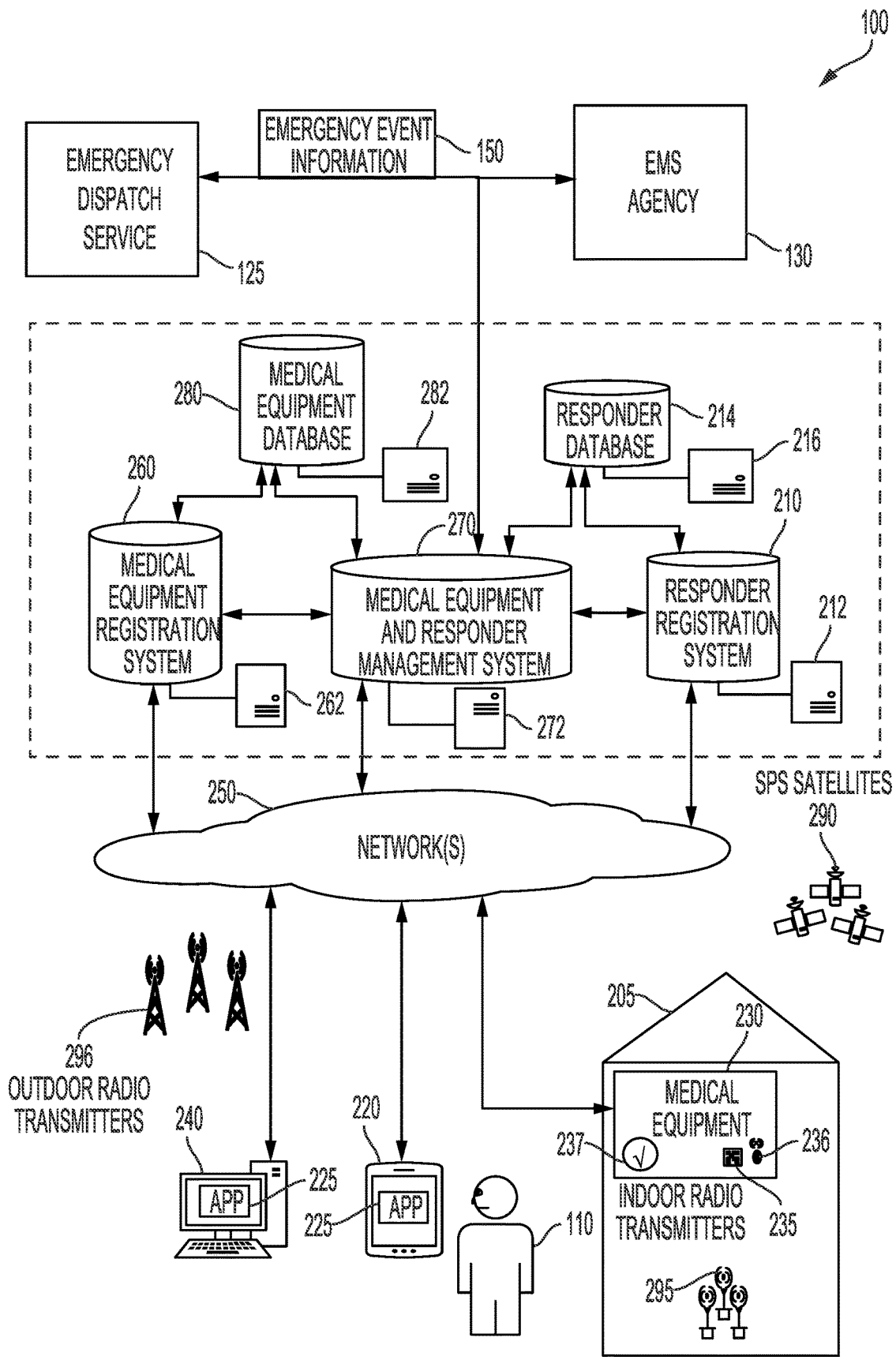
FIG. 1 shows a schematic diagram of an example of a system for responder and medical equipment management.

Techniques are presented herein to provide a responder and equipment management system that tracks locations, maintenance, operational status, and inspections for medical equipment. Further, this system may register and track responders and provide the responders with equipment status and location information during a response to the emergency event.

A medical equipment and responder management system may provide a software application for registering emergency responders and for registering medical equipment for use by the registered emergency responders. The software application may provide various user interfaces on an end user device. The user may access the software application, for example, on a computing device (e.g., a mobile device, a cellular phone, a smartphone, a tablet computer, etc.) via a web application and/or application download and a computer network such as the Internet. This software application may be compatible with various mobile device operating systems (e.g., iOS, Android, etc.). The user interfaces may capture registration information for the responders and the equipment information. Further the user interfaces may capture information from and provide information to the registered responders in real-time during an ongoing emergency event. As such, the software application may organize and facilitate the presence of the responders at the emergency event. Further, the software application may provide equipment information to the responders in order to organize and facilitate procurement and use of the medical equipment by the responders at the emergency event. The management system and the software application may access responder and equipment databases populated via the registration with the management system. Further, the management system may be communicatively linked with an emergency dispatch service so that the management system has access to emergency event information in real-time. In this manner, the responder and equipment services provided by the management system and the software application may run in parallel with dispatch services provided via an emergency medical services (EMS) agency like police, fire, ambulance, etc. However, the management system may be separate from the dispatch service as human dispatchers and/or dispatch software may not coordinate, oversee, or otherwise organize and administrate the responders and equipment registered with the management system.

Medical and/or public safety equipment like automated external defibrillators (AEDs), drug overdose kits (e.g., NARCAN®), fire extinguishers, first aid kits, trauma kits, etc. may be publicly available and designed for ease of use without specialized training. In this way, a lay person, or a professional, may provide resuscitative care to the victim within minutes of an emergency event (e.g., a cardiac arrest, a drug overdose, a fire, an injury, etc.) and possibly prior to treatment by medical professionals and/or emergency medical services. However, in order to ensure that this equipment is ready for use and compliant with local regulations and/or manufacturer's guidelines, the medical equipment may require monitoring of operational status along with routine maintenance and/or inspection. Public safety equipment, emergency equipment, and/or hospital equipment may require monitoring, maintenance, and possibly inspections to ensure that the medical equipment is in working order at the time of use. For example, medical equipment that is subject to a maintenance cycle, has a life span or expiration date and/or includes parts with a life span or expiration date, and/or includes consumable parts may require periodic inspections. Examples include, but are not limited to, external defibrillators, ventilation equipment, drug delivery equipment, physiological sensors, fire extinguishers, oxygen tanks, naloxone hydrochloride (e.g., NARCAN®) or other drug overdose kits, first aid kits, trauma kits, tourniquet equipment, eye wash kits, epinephrine auto-injectors, etc.

In order to make this medical equipment available for responders to an emergency event, an equipment management system that tracks maintenance, operational status, and inspections for the medical equipment may additionally track and/or store location information for the medical equipment. Further, the equipment management system may be a part of a larger equipment and responder management system. Responders may register with the management system and the management system may track and/or receive responder locations. At the time of an emergency event, the management system may notify responders and direct the responders to a location of the emergency equipment along with a location of the emergency event. In this way, the management system may leverage information about medical equipment in working order to enable responders to provide viable medical equipment to the emergency scene and response.

The medical equipment database may be a medical equipment registry or a database listing of medical equipment owned by particular entities. The medical equipment database may include registered location information for equipment in the database. The registered location information may be provided by an owner, user, or administrator of the equipment and/or may be self-provided by the medical equipment via a communicative coupling between the medical equipment and the database. Further, the medical equipment database may include operational status information based on an inspector's physical inspection of the medical equipment, a remote inspection, and/or a self-reported operational status.

The registered responder database may be a responder registry. This database may include identification and contact information for responders. The contact information may be contact information for the responder and a computing device associated with the responder (e.g., a cellular telephone number, an email address, an IP address, etc.). The database may include responder preferences with regard to types of emergencies, hours of availability, preferred locations, preferred equipment, etc.). The database may further include user certifications, verifications of certifications, qualifications for various medical situations, and information about equipment owned and/or in the responder's possession.

The integrated system described herein for equipment and responders may improve the efficiency and response times for first responders. Differences of fractions of minutes in a response time can mean the difference between life and death for a victim. Further, these small improvements in time can mean the difference between, for example, a neurologically and/or physiologically intact survival and a survival with serious impairment. This system may ensure that equipment procured for use at the emergency event is fully operational. Additionally, the system may identify equipment located en route to an emergency scene but difficult to find without assistance. The system may facilitate the procurement of the equipment by the responder and provide navigation instructions to the equipment as well as the emergency event. These first responders are often lay responders and the integrated system described herein may assist these responders in the use of the equipment they bring to the event. Additionally, in a situation with multiple responders, the system may coordinate the equipment procured by various responders as well as enable responders to be aware of each other's activities. As this system is managing responders outside of dispatch and outside of an EMS agency, in the absence of such a management system and associated software, these responders are not necessarily under the purview of an umbrella organization coordinating their response. Thus, this system enables otherwise independent personnel to provide a coordinated, efficient, and speedy response to an emergency event. By virtue of the management system storing and accessing equipment status information along with responder training and proficiency information, the management system may enable a response that is more likely to improve victim outcomes over an uninformed system (e.g., a system lacking a combination of equipment status information and responder training and proficiency information. Responder training and skills may be coordinated with acquisition of appropriate medical equipment and may be tailored to the needs of various types of emergency events. This may be accomplished in conjunction with professional EMS services. The registered medical equipment covers a range of types, not limited to AEDs, and therefore enables coordination of responses to emergency situations not limited to cardiac events or events requiring CPR. Further, the aggregation of equipment and responder information in a centralized management system enables data analysis directed at determining correlations between a geographic distribution of responders and equipment and emergency event outcomes. Additionally, the aggregated data may inform improvements in allocations of resources. For example, if emergency event outcomes are poor in areas that lack responders and/or medical equipment, then steps may be taken to populate such an area with responders and/or medical equipment.

Other capabilities may be provided and not every implementation according to the disclosure must provide all of the capabilities discussed. Further description and non-limiting illustrative examples of the medical equipment management software application are provided below.

Referring to FIG. 1, a schematic diagram of an example of a system for responder and medical equipment management is shown. The quantity of each component in FIG. 1 is by way of example only and other quantities of each, or any, component could be used. A high level description of FIG. 1 is provided here with a more detailed description provided following FIG. 10.

The system 100 may include a mobile computing device 220, medical equipment 230, a medical equipment and responder management system 270, a medical equipment database 280, a medical equipment registration system 260, a responder database 214, and a responder registration system 210.

The mobile computing device 220 may be, for example, but not limited to a cellular telephone, a tablet, a laptop, a wearable device, etc. In an implementation, the mobile computing device 220 may be a group of communicatively coupled devices. Claimed subject matter is not limited to a particular type, category, size, etc. of computing device. Specific hardware components of the mobile computing device 220 are discussed in detail with regard to FIG. 30A. These components may include a processor 1010a, a memory 1020a, an input device 1030a, an output device 1040a, a location module 1050a, a transceiver 1070a, a camera 1080, and an asset tag reader 1090.

The medical equipment 230 in FIG. 1 may be an AED. However, this is an example only and the medical equipment 230 may include equipment other than AEDs such as public safety equipment, emergency equipment and/or hospital equipment (for example, but not limited to external defibrillators, ventilation equipment, drug delivery equipment, physiological sensors, fire extinguishers, oxygen tanks, drug overdose kits (e.g., NARCAN® kits), first aid kits, trauma kits, tourniquet equipment, eye wash equipment, etc.). The medical equipment 230 may include an asset tag (e.g., the barcode 235 and/or the radio frequency identification (RFID) tag 236) and/or a status indicator 237. The medical equipment 230 may further include one or more of the components shown in FIG. 30B and described in detail below in regard to FIG. 30B. These components may include a processor 1010b, a memory 1020b, an input device 1030b, an output device 1040b, a location module 1050b, and a transceiver 1070b.

The medical equipment database 280, the medical equipment registration system 260, the responder database 214, the responder registration system 210, and the management system 270 are described below and shown in FIG. 1 as separate entities for clarity. However, one or more of these entities may be combined into a single entity. For example, the registration systems 210 and 260 may be implemented as functions performed by the management system 270. As a further example, the management system 270 may include one or more of the databases 214 and 280.

The user 110 may be one or more of a medical equipment owner, manager, distributor, user, administrator, and manufacturer and/or may be a potential responder to an emergency event. Although shown in FIG. 1 as a single user for simplicity, the user 110 may represent one or more users. For example, one or more first users may register medical equipment and one or more second users may register as potential responders.

One or more users 110 may each establish one or more of an equipment management account with the management system 270, an equipment registration account with the equipment registration system 260, and a responder registration account with the responder registration system 210. In various implementations, the equipment management account and the equipment registration account may be separate accounts, may be combined as a single account, and/or may be linked accounts. One or more equipment owners, distributers, or other provider or administrator of the medical equipment may have access to one or both of these accounts.

The owner, distributor, or other provider or administrator of the medical equipment may purchase a subscription or otherwise secure access to the management system 270. Such access may be via the management system account. Once the user 110 has established the responder registration account, the user 110 may be a registered responder. The management system 270 may interact with the registered responder via the computing device 220 that is associated with the registered responder via registration information stored in the responder database. Additionally, potential responders may register themselves with the management system via the responder registration system 210 and secure access to this system via a responder account.

The management system 270 may provide and/or administer a software application 225. The software application 225 is a downloadable software application configured to operate on the mobile computing device 220. In an implementation, the software application 225 may be downloadable or web-access software configured to operate on the remote computing device 240. The mobile computing device 220 and/or the remote computing device 240 may download the software application 225 and/or access an associated website via a wired and/or wireless communicative coupling to the network(s) 250. The software application 225 may be compatible with various mobile device operating systems (e.g., iOS, Android, etc.). The management system 270 may receive and track data captured by the user interfaces provided by the software application 225 and/or location information for the mobile computing device 220 provisioned with the software application 225. In this way, the management system 270 may provide equipment management services and/or responder location and notification services via the software application 225. In an implementation, the software application 225 may be web-access software accessible via the network(s) 250.

Figure 2A:
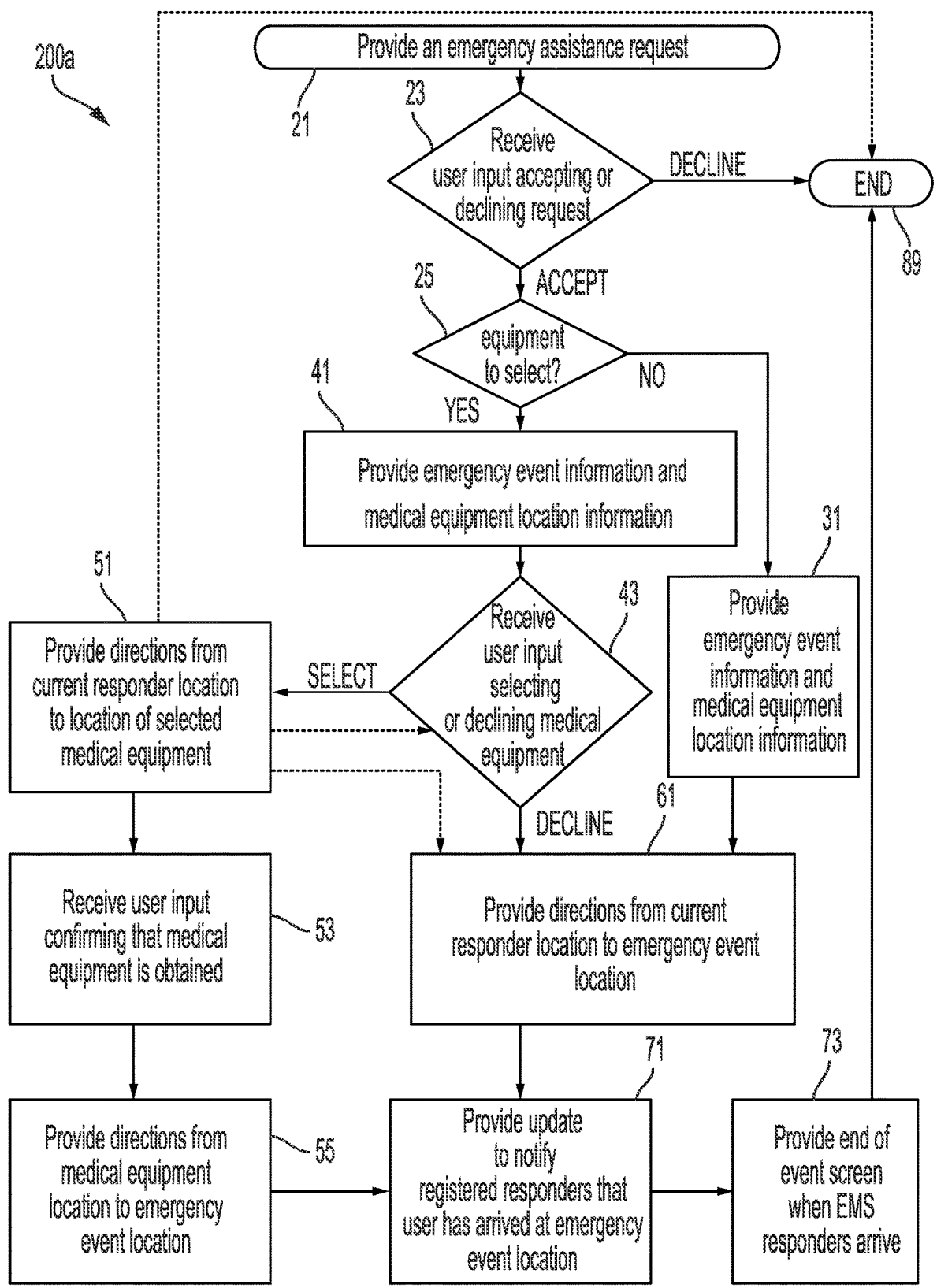
FIGS. 2A-2C show block diagrams of examples of an automated method for providing responders and equipment to an emergency event.

Referring to FIG. 2A, a block diagram of a computer-implemented method for providing responders and equipment to an emergency event is shown. The stages of the method 200a are described below with reference to user interface examples shown in FIGS. 3-10. A processor of the computing device 220 (e.g., the processor 1010a shown in FIG. 30A) may execute functions of the software application 225 to control an output device (e.g., the output device 1040a shown in FIG. 30A) and/or an input device (e.g., the input device 1030a shown in FIG. 30A) to provide information to and capture information from the registered responder 110. In an implementation, as illustrated for example in FIGS. 3-10, the software application 225 may provide and receive information via a graphical user interface (GUI) on a display screen. The display screen may be a touchscreen configured to function as both an input and an output device. Alternatively, or additionally, the software application 225 may provide and receive all or a portion of the information described with regard to FIGS. 2A-10 via other input and/or output devices which may include, for example, but not limited to, one or more of audio and/or haptic devices, a camera, a radio receiver and/or transmitter, etc.

At the stage 21, the method 200a includes providing an emergency assistance request (e.g., an emergency alert) to one or more computing devices. For example, the computing device 220 associated with the registered responder 110 may receive the emergency assistance request from the management system 270 via the network(s) 250. The management system 270 may provide the emergency assistance request in response to receiving emergency event information 150 from an emergency dispatch service 125. In an implementation, the emergency dispatch service 125 may be a computer-aided dispatch (CAD).

In an exemplary scenario, a victim, bystander, or other observer of or witness to an emergency event may notify the emergency dispatch service (e.g., an emergency dispatch office or other a public safety answering point accessible via a "9-1-1" call). The emergency dispatch service 125 may push out emergency event information 150 to one or more emergency medical services (EMS) organizations or agencies (e.g., EMS 130 as shown in FIG. 1). The emergency event information 150 may include a code that indicates a type of emergency (e.g., a physical condition of an emergency victim such as cardiac arrest, drug overdose, chemical exposure, trauma, bleeding, breathing difficulty, etc.) and a location of the emergency event. The emergency event information 150 may further include victim information (e.g., demographic information such as age, gender, physical description information, etc.).

The emergency dispatch service 125 may concurrently and automatically send the emergency event information 150 to the management system 270. The emergency event information 150 includes at least a location of the emergency event and may include further information about the emergency event (e.g., the type of event, equipment needed, etc.). The emergency dispatch service 125 may time-stamp the emergency event information 150 and the time of transmission, the time of receipt by the EMS agency 130 and the time of receipt by the management system 270 may all be the time indicated by the time-stamp.

In order to identify registered responders in a vicinity of the emergency event, the management system 270 may push the emergency event information to one or more computing devices (e.g., the computing device 220) associated with registered responders in the responder database 214 and that include the application 225. For example, the computing devices may be cellular telephones and the responder database 214 may include a cellular telephone number for each registered responder. In an implementation, the management system 270 may send the emergency assistance request to all of the computing devices in the responder database 214. Alternatively, the management system 270 may filter the responder registration information to identify a set of computing devices from all of the computing devices in the responder database 214. The filtering may identify the set of computing devices as including those computing devices currently located within a vicinity of the emergency event. Alternatively, the filtering may identify the set of computing devices as including computing devices expected to be within the vicinity of the emergency event based on registration information. For example, the registration information may include location schedule that identifies when the responder expects to be located at various locations such as work, home, etc. The registration information may indicate days and/or times at which the responder indicates that they are at particular locations. In an implementation, the management system 270 may accept and store responder unavailability information for the expected locations and/or may accept and store temporary location information. For example, if the responder is traveling or otherwise relocated for a period of time, the responder can provide this information to the management system 270.

Upon receipt of the emergency event information, the application 225 may compare the location of the computing device (e.g., as determined via one or more of the SPS satellites 290, the outdoor radio transmitters 296, and/or the indoor radio transmitters 295) with the emergency event location. For each computing device, if the comparison indicates that the computing device is in a vicinity of the emergency event, then the application 225 identifies that computing device to the management system 270 (e.g., notifies the system 270 that the particular computing device is in the vicinity of the emergency event and sends a location response to the management system 270.

In various implementations, the geographic area considered to be in a vicinity of the emergency event may be determined in a variety of ways. For example, the vicinity of the emergency event may be an area of a pre-determined radius centered on the emergency event. This pre-determined radius may be, for example, 50 meters, 100 meters, 200 meters, 300 meters, 400 meters, or 500 meters. Such a pre-determined distance may be determined based on a distance that a person on foot at an average walking speed of 3-7 kph could reasonably be expected to traverse within a time period of 2-4 minutes or in less than 5 minutes, or less than 10 minutes. In an implementation, the management system 270 may determine the vicinity of the emergency event based on the type of emergency event and/or a number of emergency events within an area. For a cardiac arrest, arrival of a responder at the victim within a time frame of 2-4 minutes may be crucial as survival rates for cardiac arrest may drop by 10% for every minute of time without CPR following the cardiac arrest. However, an emergency response for an emergency event other than cardiac arrest may be viable after a longer period of time than for a cardiac arrest. Therefore, the pre-determined distance may be greater than that for a cardiac arrest. As another example, the management system 270 may select a longer pre-determined distance for a mass casualty event than an event involving a single victim in order to access a larger pool of responders. As a further example, the vicinity of the emergency event may depend on a mode of transport of the responder. For instance, the responder may walk or drive to the emergency event. An estimated travel time for driving may be shorter than that for walking. In this case, the geographic area in the vicinity of the emergency event for a driving responder may be larger than that for a walking responder. In an implementation, the software application 225 may include a user-determined setting indicating the mode of transport of the registered responder and/or a user preference for a qualifying distance from the emergency event. As an example, a registered responder in an urban setting may select walking and a registered responder in a rural setting may select driving. In an implementation, the geographic area considered to be in the vicinity of the emergency event may vary based on a population density, for example, based on an area being urban, suburban, rural, etc. In a further implementation, the management system 270 may receive and/or store a location of the EMS agency responding to the emergency event. The management system 270 may request that registered responders located within a distance of the emergency event that is less than the distance from the EMS agency receive the emergency assistance request.

The location response may include the current location of the computing device which is also the current location of the registered responder associated with the computing device. Thus, the location response includes responder location information. The management system 270 may then provide the emergency assistance request to one or more computing devices identified as being located in the vicinity of the emergency event. In an implementation, the management system 270 may only send the emergency assistance request to this set of computing devices and may not send the emergency assistance request to computing devices that are not in this set and therefore not identified as being in the vicinity of the emergency event.

As an example not limiting of the disclosure, suppose the management system 270 sends the emergency event information 150 to a pool of one hundred phones, each associated with a registered responder. Further, suppose that the pre-determined distance is an area centered on the emergency event with a 200 meter radius and that ten of these phones are located within this area. Then, in this example, these ten phones and the associated registered responders are within the vicinity of the emergency event and may receive the emergency assistance request at the stage 21. The other ninety phones are not within the vicinity of the emergency event and may not receive the emergency assistance request at the stage 21.

In an implementation, the software application 225 may receive a user-input location of the computing device 220, for example, if SPS satellite signals and/or radio transmitter signals are unavailable and/or too weak for use in location determination. The software application 225 may provide the location of the computing device 220 to the management system 270 and/or may store the location locally on the computing device 220 (e.g., in the memory 1020a). The software application 225 may store an indication that the location for the computing device 220 is the user-input location.

At least for the purposes of this disclosure, the computing device 220 is assumed to be in the possession of or readily accessed by the associated registered responder. Therefore, the location of the registered responder 110 may be assumed to be the same as and interchangeable with the location of the associated computing device 220. Thus, providing and/ or receiving a computing device location may be equivalent to providing and/or receiving a registered responder location.

Figure 3:
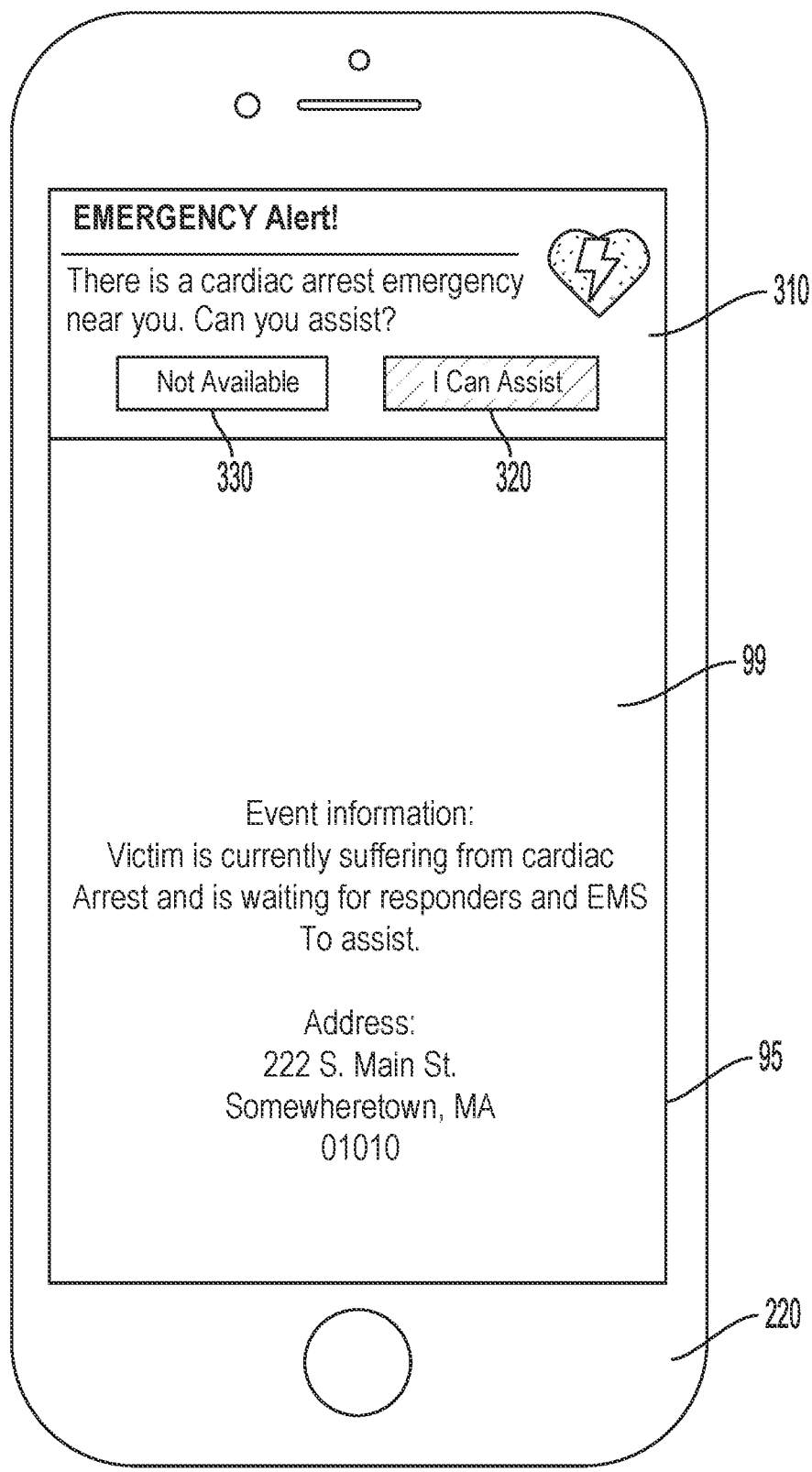
FIG. 3 shows an example of a user interface for an emergency assistance request.

Referring to FIG. 3, an example of an emergency assistance request user interface is shown. In response to the receipt of the emergency assistance request, the software application 225 may provide the emergency assistance request 310 at the user interface 99. As described above, the software application 225 may provide the user interface 99 on a display screen 95 of the computing device 220. The emergency assistance request 310 may include touchscreen buttons configured to capture user responses to the emergency assistance request 310. For example, emergency assistance request may include an accept button 320 and a decline button 330.

Referring again to FIG. 2A, at the stage 23, the method 200a includes receiving a user input that accepts or declines the emergency assistance request. For example, the registered responder 110 may press the accept button 320 shown in FIG. 3 to accept the emergency assistance request or may press the decline button 330 shown in FIG. 3 to decline the emergency assistance request. The input to the accept button 320 or the decline button 330 may determine a response status of the registered responder 110. The management system 270 and/or the software application 225 may receive the user input captured via the buttons 320 or 330. The acceptance of the emergency assistance request initiates an assistance request session.

In response to the registered responder declining the emergency assistance request, the method 200a proceeds to the stage 89. At the stage 89, the software application 225 ends the assistance request session. The software application may initiate a new assistance request session upon receipt of a new emergency assistance request by the computing device 220.

In response to the registered responder accepting the emergency assistance request, the method 200a proceeds to the stage 25. At the stage 25, the method includes receiving equipment availability information. For example, based on equipment availability information in the medical equipment database 280, the management system 270 may determine if there is available medical equipment for the registered responder 110. The management system 270 may provide the equipment availability information to the software application 225.

The management system 270 may determine equipment availability based on one or more of operational status, time availability, and geographic location. The determination of the equipment availability information based on operational status and time availability is described in further detail below with regard to Table 1. In brief, the operational status may determine if the equipment is available for use because it is verified as operational or unverified as operational or if the equipment is unavailable for use because it is verified as non-operational. The time availability may determine if the equipment is available because the storage location is publicly accessible at a particular day and time or if the equipment is unavailable because the storage location is not publicly accessible at the particular day and time.

With regard to geographic location, in an implementation, the management system 270 may filter equipment registration information in the equipment database 280 to identify a set of registered medical equipment location within a vicinity of the emergency event location. The management system 270 may limit the equipment presented to the registered responder(s) to this set of equipment.

Figure 4A:
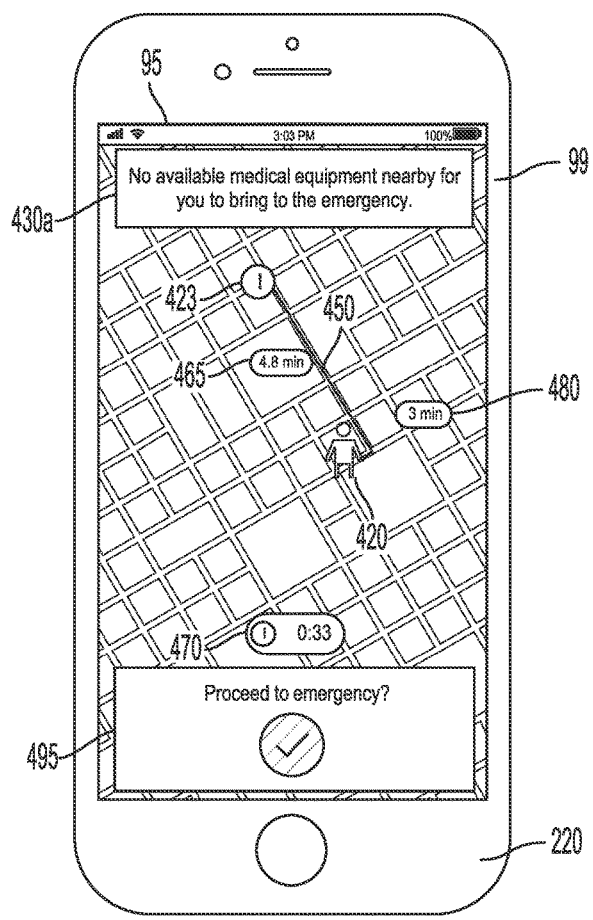
FIGS. 4A-4C show examples of an interactive map for responder navigation and equipment selection.
Figure 4B:
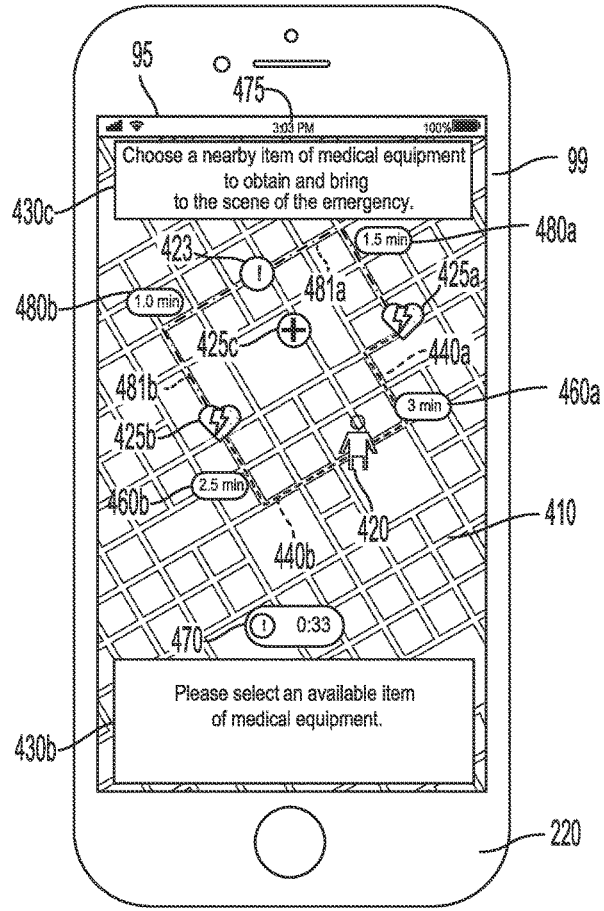
Figure 4C:
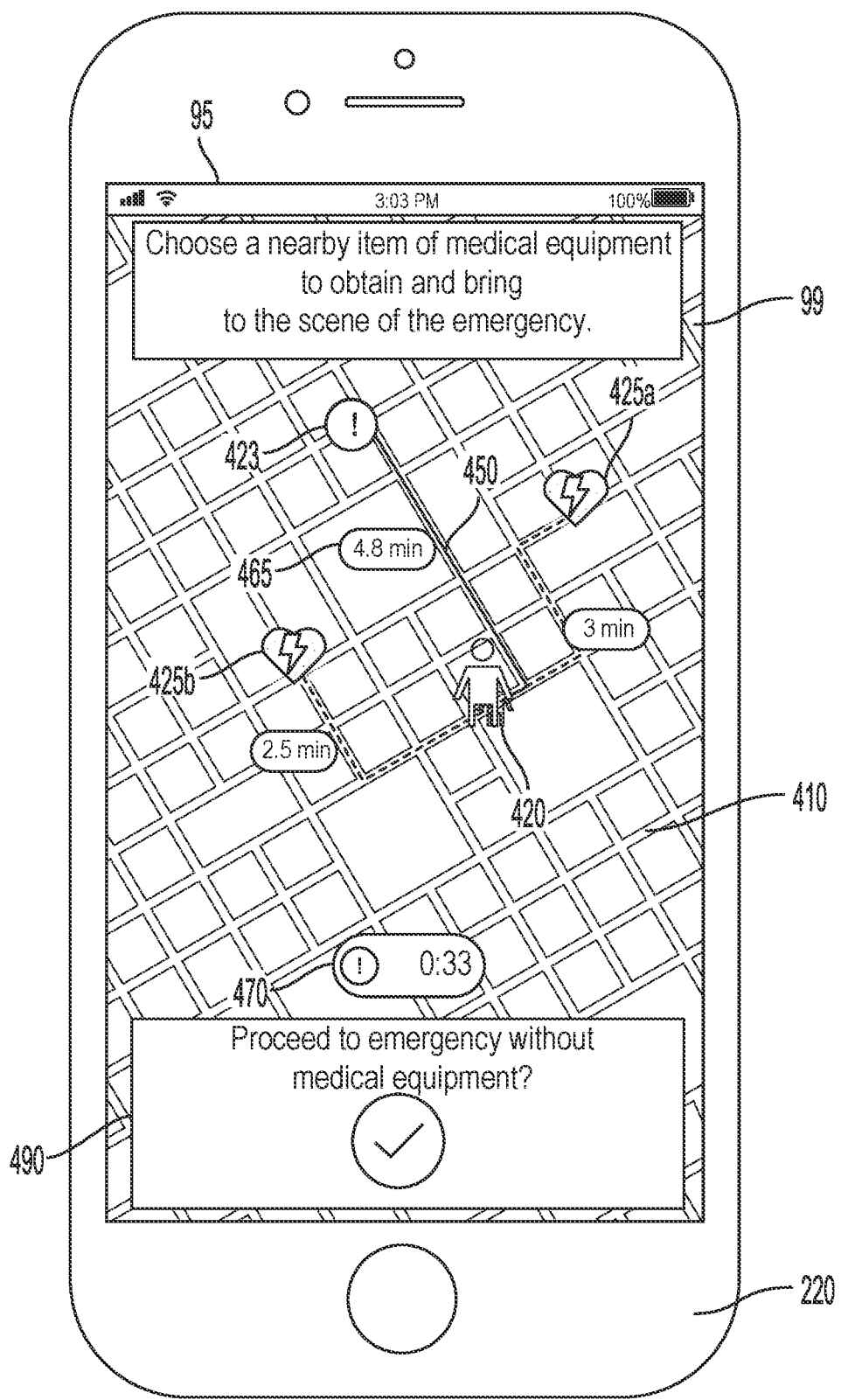

If the medical equipment is unavailable, the method 200a proceeds from the stage 25 to stage 31. If the medical equipment is available, the method 200a proceeds from the stage 25 to stage 41. As shown in FIGS. 4A, 4B, and 4C, at stage 31 and at stage 41, the software application 225 provides an interactive map that includes a location indicator 420 for the registered responder. The position of the location indicator 420 for the registered responder may correspond to a tracked location of the computing device associated with the registered responder.

In an implementation as described above, prior to the acceptance of the emergency assistance request, the management system 270 receives the locations of the computing devices associated with registered responders at discrete intervals and in response to the push of the emergency event information. In an alternative implementation, prior to the acceptance of the emergency assistance request, the management system 270 may continuously or periodically track locations of computing devices associated with registered responders and the management system 270 may determine which of these computing devices are in the vicinity of the emergency event. However, in either implementation, following the acceptance of the emergency assistance request, the registered responder 110 has entered the assistance request session for the emergency event. During the session, the management system 270 may automatically track the location of the computing device 220 in order to evaluate the navigation status of the registered responder. The management system 270 may track the location via a third-party mapping application. For example, the tracked location of the computing device may indicate that the registered responder is en route to an item of medical equipment, en route to the emergency event, arrived at (e.g., co-located with) the item of medical equipment, or arrived at (e.g., co-located with) the emergency event. When the registered responder has arrived at the item of medical equipment, the management system 270 may consider the computing device 220 to be co-located with the item of medical equipment. Similarly, when the registered responder has arrived at the emergency event, the management system 270 may consider the computing device 220 to be co-located with the emergency event. Once the registered responder 110 exits the session (e.g., at the stage 89 in FIG. 2A), the management system 270 may automatically terminate the location tracking.

Figure 9:
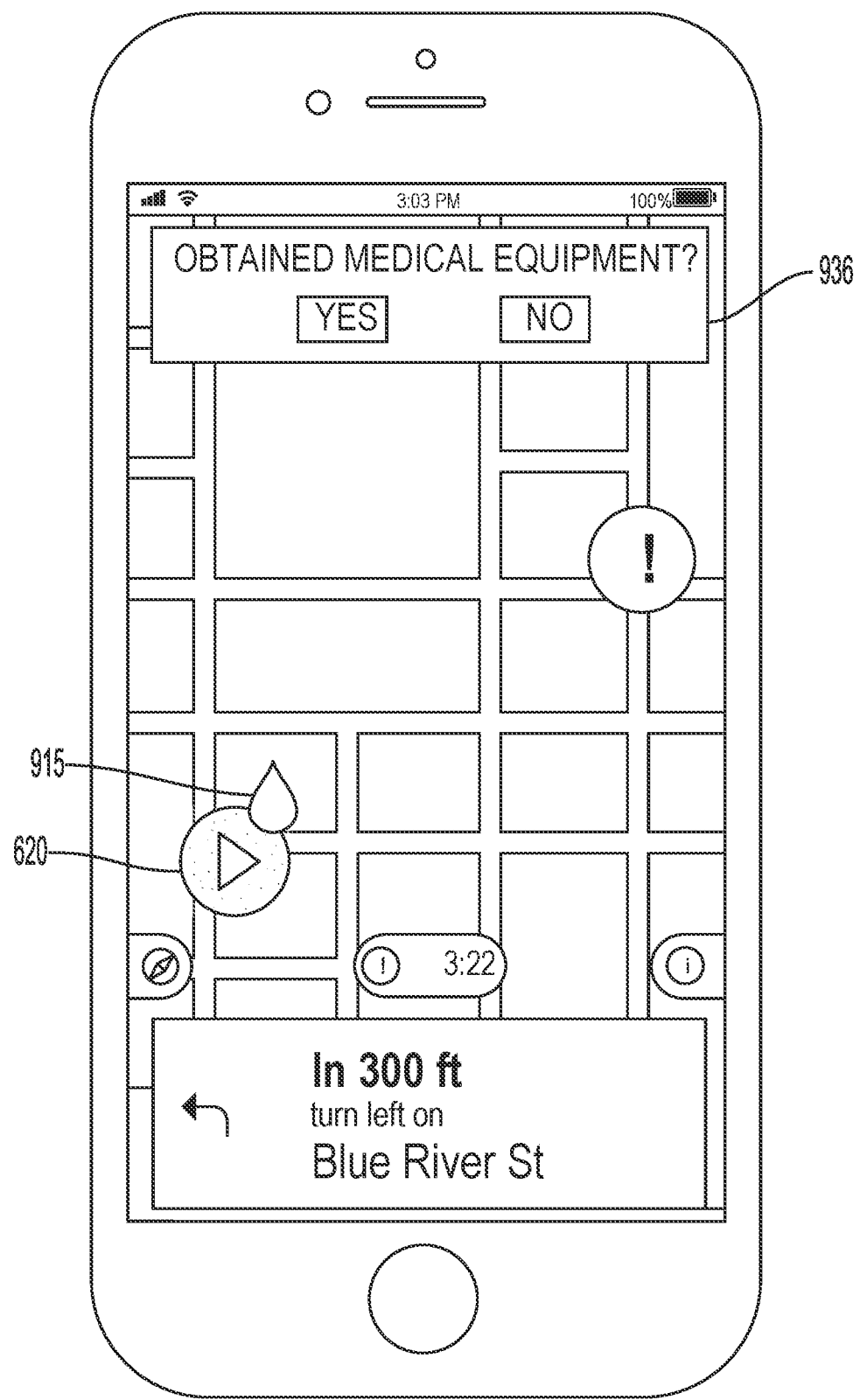
FIG. 9 shows an example of an equipment acquisition control.
Figure 11A:
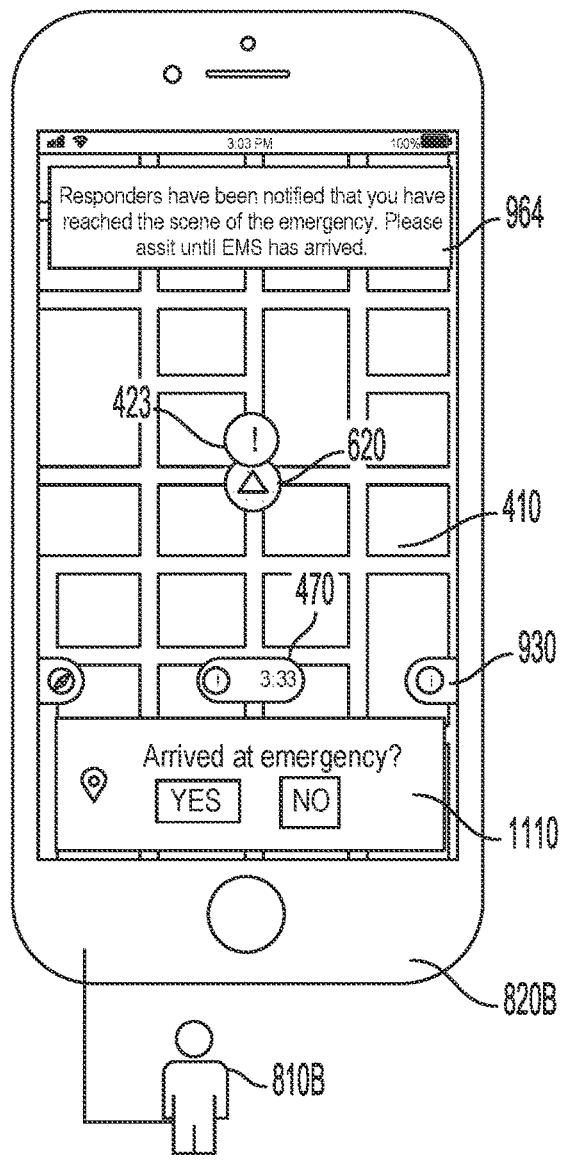
FIGS. 11A and 11B show examples of navigation and confirmation features of the software application.

In various implementations, the software application 225 may determine the navigation status of the registered responder 110 from input to a navigation control in addition to or as an alternative to tracking the location of the computing device 220. For example, as described herein, the navigation control may include one or more of an equipment decline control 490 (e.g., as shown in FIG. 4C), a proceed-to-emergency control 495 (e.g., as shown in FIG. 4A), a proceed-to-equipment control 590a (e.g., as shown in FIG. 5A), and an equipment acquisition control 936 (e.g., as shown in FIG. 9), and an arrive-at-emergency control 1110 (e.g., as shown in FIG. 11A). These controls are described in further detail with regard to the aforementioned figures. In brief, each control notifies the software application 225 of an update or change in the navigation status of the registered responder.

Referring again to FIG. 2A, at the stage 31, the software application 225 provides an interactive map 410 as shown in FIG. 4A that includes a location indicator 420 for the registered responder and a location indicator 423 for the emergency event. In an implementation, the management system 270 may provide interactive map information for display at the interactive map 410. The interactive map information may include, for example, automatically tracked locations for the mobile computing device 220, the emergency event location, and/or medical equipment location information. The software application 225 may provide the interactive map 410 at the user interface 99 on the display screen 95 of the computing device 220. The interactive map 410 may include a responder location indicator 420 at the current map location of the registered responder 110 and the emergency event location indicator 423 at the map location of the emergency event. In an implementation, the interactive map 410 may include a message 430a to notify the registered responder 110 that there is no available medical equipment to select and bring to the emergency. For example, there may not be an available AED, first aid kit, trauma kit, or another type of medical equipment. In this case, as shown, for example in FIG. 4A, the software application 225 may provide a proceed-to-emergency control 495. In an implementation, the software application 225 may determine that the navigation status of the registered responder is en route to the emergency based on the input to the proceed-to-emergency control 495 and/or based on the tracked location of the computing device 220. The proceed-to-emergency control 495 may capture a user touchscreen gesture, such as, for example, a tap, to confirm that the registered responder 110 chooses to proceed to the emergency event. The interactive map 410 with no available medical equipment may exclude the equipment location indicators 425a, 425b, and 425c shown in FIG. 4B.

In an implementation, the location indicators on the interactive map 410 may be graphic icons. As discussed below with regard to FIG. 7, the software application 225 may provide an activity log. In an implementation, the activity log may include graphic icons that may match an appearance (e.g., color, shape, etc.) of the graphic icons used as location indicators on the interactive map 410.

At the stage 41, the software application 225 provides emergency event information and medical equipment location information. For example, the software application 225 may receive the medical equipment location information from the medical equipment database 280 via the management system 270. The received medical equipment location information may include locations of medical equipment in a vicinity of the emergency event.

As shown in FIG. 4B, the software application 225 may provide the interactive map 410 that includes a location indicator 420 for the registered responder, a location indicator 423 for the emergency event, and one or more equipment location indicators 425a, 425b, and 425c for the available medical equipment. The software application 225 may provide the interactive map 410 on the user interface 99 provided on the display screen 95 of the computing device 220. The interactive map 410 may include the location indicator 420 of the current location of the registered responder 110 and the emergency event location indicator 423 at the map location of the emergency event. The interactive map 410 may further provide one or more equipment location indicators 425a and 425b on the interactive map 410 at the map locations of the medical equipment. In the example of FIG. 4B, the equipment location indicators 425a and 425b have a same icon shape. In an implementation, equipment location indicators with the same icon shape may correspond to one particular type of medical equipment. For example, the heart shaped icon shown in FIG. 4B may correspond to an AED. In an implementation, the interactive map 410 may include other indicator shapes 425c that correspond to other types of medical equipment. For example, a "+" shape of icon or icon that includes a plus-type symbol signifying first aid may correspond to a first aid kit and/or a trauma kit, a water droplet icon may correspond to an eye wash station, a hypodermic needle icon may correspond to drug administration equipment, etc. These icon shapes are examples only and not limiting of the disclosure.

In an implementation, the interactive map 410 may provide a timer 470. The timer 470 may display an elapsed time between a current time (e.g., the current time 475 provided by the computing device 220 and a time of receipt at the management system 270 of the emergency event information from the emergency dispatch service. As described above, the emergency dispatch service 125 may simultaneously provide the time-stamped emergency event information 150 to the EMS agency 130 and the management system 270. In an implementation, the software application 225 may change an appearance aspect of the timer 470 in order to indicate various intervals of response time. For example, during a time period closest to the receipt of the emergency assistance request, the timer 470 may be a first color, such as, for example, green. As an example, this first time period may be an elapsed time of 0-1 minutes, 0-2 minutes, 0-4 minutes, or 0-5 minutes. During a second and subsequent time period, the timer 470 may be a second color such as, for example, yellow. The second time period may be, for example, an elapsed time of 1-2 minutes, 2-4 minutes, 4-8 minutes, 5-10 minutes. During a third time period that may last until the arrival of the EMS personnel and/or an exit from the assistance request session, the timer 470 may be a third color such as, for example, red. The third time period may start at the end of the second time period. The duration of the any or all of the time periods may depend on the type of emergency event. In addition to or as an alternative to color variations, the software application 225 may cause the timer 470 to flash, enlarge, and/or emit one or more sounds in all or some of the time periods. In an implementation, the sounds may be characteristic of a specific time period. While three time periods are provided as examples, 2 or more time periods are within the scope of the disclosure.

In addition to the location indicators, the interactive map 410 may include routing information. The routing information may include one or more navigation paths to the available medical equipment (e.g., the navigation paths 440a and 440b) and/or one or more navigation paths to the emergency event (e.g., the navigation path 450). In an implementation, the one or more navigation paths to the available medical equipment and/or the one or more navigation paths to the emergency event may represent a shortest path based on distance and/or based on an estimated travel time.

In an implementation, the interactive map 410 may provide indicators 460a and 460b of the estimated travel time for one or more of the displayed navigation paths to the equipment (e.g., the paths 440a and 440b). In a further implementation, the management system 270 may send an equipment acquisition recommendation based on the travel time to the computing device 220 for display on the interactive map 410. For example, the software application 225 may change an appearance aspect of the equipment location indicator (e.g., the indicator 425a or 425b) and/or the navigation path (e.g., the path 440a or 440b) based on the estimated travel time and/or the equipment acquisition recommendation. For example, the equipment location indicator for the equipment associated with a shorter travel time may a different size and/or color than the equipment location indicator for the equipment associated with the longer travel time. Alternatively or additionally, the equipment location indicator for the equipment associated with the shorter travel time may flash.

In an implementation, the interactive map 410 may provide estimated travel time 480a and 480b for the navigation paths 481a and 481b from the equipment to the emergency event.

The interactive map 410 may further include messages (e.g., the messages 430b and 430c) for the registered responder 110. The messages may provide instructions and/or other information germane to responding to the emergency event. The messages may, for example, instruct the registered responder 110 to select an available item of medical equipment to obtain and bring to the medical emergency. The map icons (e.g., 425a, 425b, 425c) may indicate various types of medical equipment available (e.g., AED, first aid kit, trauma kit, or another type of medical equipment).

Referring again to FIG. 2A, the method 200a proceeds from the stage 41 to the stage 43. At the stage 43, the method 200a includes receiving user input selecting or declining the available medical equipment. Referring to FIG. 4C, in an implementation, equipment may be available for selection, however, the registered responder may select to proceed to the emergency without any equipment. In this case, the method 200a proceeds from the stage 41 to the stage 43.

At the stage 43, the registered responder 110 may provide input to decline or select a particular item of medical equipment and the management system 270 receives this user input. If the interactive map 410 displays at least one medical equipment location indicator 425a, 425b, and/or 425c and the user 110 provides a touchscreen gesture such as, for example, a tap on the emergency event location indicator 423, this may indicate the decline of medical equipment. In an implementation, as shown, for example in FIG. 4C, the software application 225 may provide an equipment decline control 490. The equipment decline control 490 may capture a user touchscreen gesture, such as, for example, a tap, to confirm that the registered responder 110 chooses to proceed to the emergency event without navigating to any of the medical equipment locations provided on the interactive map 410. In an implementation, the software application 225 may determine that the navigation status of the registered responder is en route to the emergency based on the input to the equipment decline control 490 and/or based on the tracked location of the computing device 220. If the user declines the available medical equipment then the method 200a proceeds from the stage 43 to the stage 61. At the stage 61, in response to receiving the confirmation to proceed to the emergency event, the software application 225 may display a navigation route 450 to the emergency event. In an implementation, the software application 225 may further provide a travel time estimate 465 to the emergency event. In an implementation, the navigation route 450 may be an outdoor route, an indoor route, or a combination thereof.

Alternatively, if the interactive map 410 displays at least one item of medical equipment and the user 110 provides a touchscreen gesture such as, for example, a tap on the medical equipment location indicator 425a, 425b, or 425c this may indicate the selection of the medical equipment. Referring to FIGS. 5A & 5B, examples of equipment selection features provided at the interactive map by the software application 225 are shown. In an implementation, if the user selects a particular item of medical equipment, the software application 225 may provide one or more medical equipment selection features. In an implementation, in response to the user input that selects the equipment location indicator 425a, the software application 225 may change an appearance aspect of the equipment location indicator 425a. For example, the software application 225 may render the equipment location indicator 425a in a different color than the equipment location indicator 425b. The different color may indicate the user selection of the equipment location indicator 425a. The software application 225 may change the color of the indicator 425a from a first color corresponding to "unselected" to a second color corresponding to "selected." In an implementation, in further response to the user input that selects the equipment location indicator 425a, the software application 225 may change an appearance aspect of the navigation route 440a between the user 110 and the selected equipment location indicator 425a. For example, prior to selection of the particular item of medical equipment associated with the indicator 425a, the software application 225 may represent both navigation routes 440a and 440b as dotted lines (e.g., as shown for example in FIG. 4A). Following the selection of the equipment location indicator 425a, the software application 225 may change the representation of the navigation route 440a to a solid line, as shown, for example, in FIG. 5A.

In an implementation, following a selection of the one particular item of medical equipment, the application 225 may provide a proceed-to-equipment controls 590a and 590b. The registered responder 110 may provide an input (e.g., a touch screen gesture) to the proceed-to-equipment control 590a or 590b to confirm that he/she is en route to the selected equipment. In an implementation, the proceed-to-equipment control 590a and/or 590b may indicate medical equipment in general (e.g., "Proceed to selected medical equipment?") or may indicate a specific type of medical equipment. For example, the control 590a indicates that the type of medical equipment is an AED and the control 590b indicates that the type of medical equipment is a first aid kit. In an implementation, the software application 225 may determine that the navigation status of the registered responder is en route to the equipment based on the input to the proceed-to-equipment control 590a and/or 590b and/or based on the tracked location of the computing device 220.

In an implementation, following a selection of the one particular item of medical equipment, the user 110 may select a different particular item of medical equipment. For example, the registered responder 110 may make a first selection of the equipment location indicator 425b and then make a second selection of the equipment location indicator 425c. In response to the second selection, the software application 225 may change an appearance aspect of the equipment location indicators 425b and 425c to indicate the change in selection. For example, the software application 225 may change the color of the indicator 425c from the first color corresponding to "unselected" to the second color corresponding to "selected." Concurrently, the software application 225 may change the color of the indicator 425b from the second color corresponding to "selected" to the first color corresponding to "unselected." Additionally or alternatively, the software application 225 may change the representation of the navigation route 440b from the dotted line to the solid line and change the representation of the navigation route 440a from the solid line back to the dotted line, as shown for example by comparing FIG. 5A with FIG. 5B. The user 110 may change the selection of the medical equipment one or more times. Additionally, as shown in these examples, the change in selection may also correspond to a change in the selected type of medical equipment. In this example, the user selected an AED in FIG. 5A but changed to a first aid kit in FIG. 5B.

In an implementation, the software application 225 may provide a time warning to the registered responder 110 if the time associated with the equipment selection process exceeds a pre-determined threshold in order to ensure that the registered responder 110 proceeds to the emergency event in a timely fashion. For example, the warning may advise the user 110 to finalize a selection of the medical equipment within an amount of time.

In an implementation, the software application 225 may enable the user to select multiple items of medical equipment and may provide sequential navigation instructions to the multiple items of medical equipment. In various implementations, the software application 225 may change the equipment selection process dynamically based on locations and/or medical equipment selections of various responders. For example, the software application 225 may identify two or more type of medical equipment relevant to the emergency event. The software application 225 may provide equipment location information about a first type of equipment to a first registered responder and may provide equipment location information about one or more additional types of equipment to one or more additional registered responders. The medical equipment suggested to various responders may depend on the relative locations of the responders with regard to the medical equipment and/or the emergency event. In an implementation, the software application 225 may suggest a type of equipment and/or limit the equipment location information to a particular type of equipment for the second responder in response to a selection of equipment by the first responder. For example, the emergency event may involve a drug overdose for which an AED and a drug overdose kit are appropriate. The first responder may select the AED and the software application 225 may suggest and/or limit the equipment choices for the second responder to drug overdose kits. In an implementation, the software application 225 may remove the first type of medical equipment from the interactive map 410 provided to the additional responders and/or change the appearance of the medical equipment location indicators for the additional responders and/or otherwise prevent or discourage selection of the first type of medical equipment by the additional responders.

Referring again to FIG. 2A, once the registered responder 110 selects the proceed-to-equipment control 590, the method 200a proceeds from the stage 43 to stage 51. At the stage 51, the software application 225 may provide directions to the location of the selected medical equipment along with various instructions, prompts, and/or user selectable location indicators at the interactive map 410. These are discussed below with reference to examples of navigation and information features provided by the software application 225 as shown in FIGS. 6 and 7.

Figure 6:
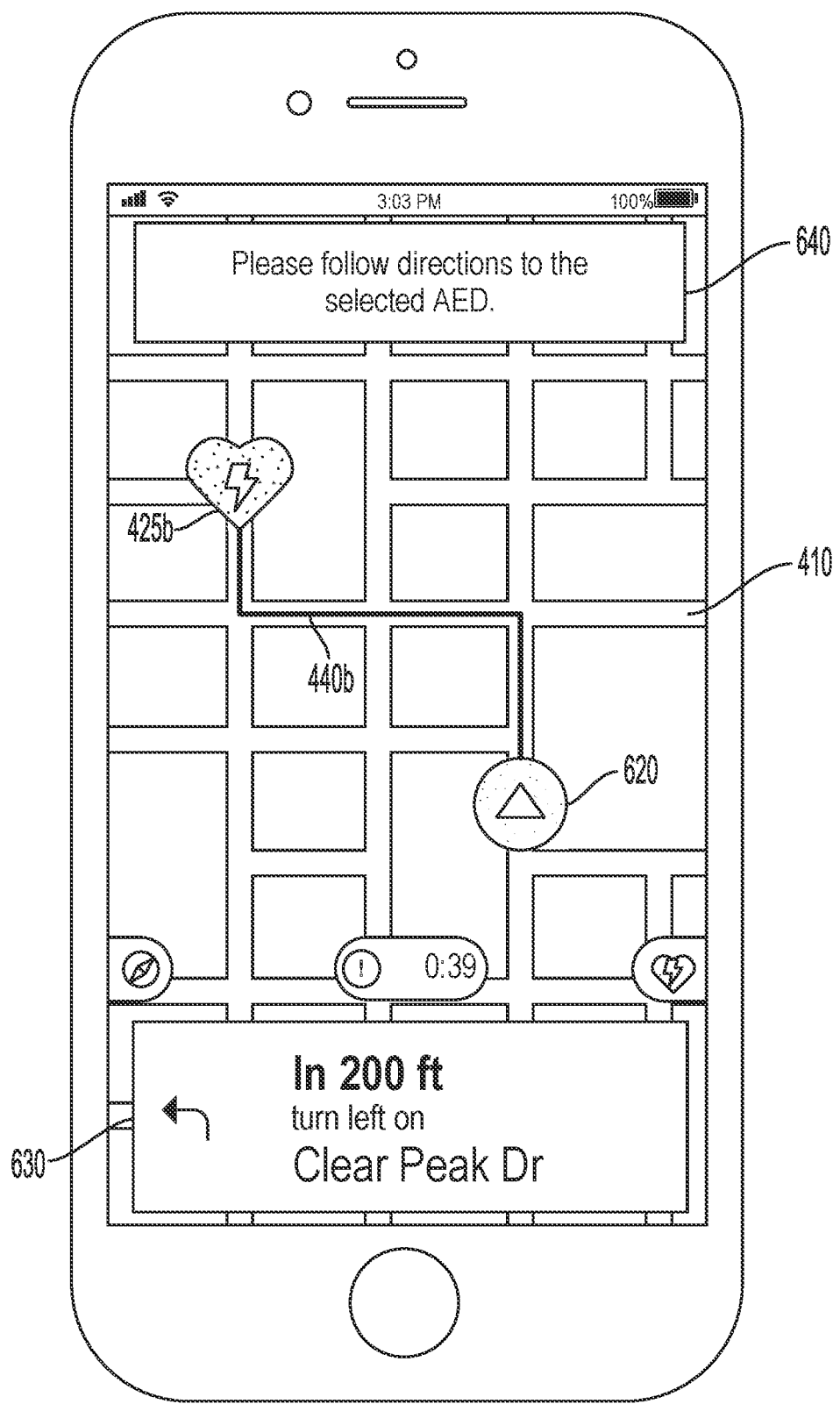
FIGS. 6 and 7 show examples of navigation and information features provided by the software application.

Referring to FIG. 6 with further reference to FIG. 2A, in an implementation, at the stage 51 the software application 225 may provide an instruction 640 for the registered responder 110 to proceed to the selected medical equipment. In an implementation, the instruction 640 may include the type of medical equipment selected, in this example an AED. The interactive map 410 may provide the responder location as a responder navigation icon 620. The responder navigation icon 620 may indicate a position of the registered responder along a navigation path towards the selected medical equipment and/or towards the emergency event. The responder navigation icon 620 may differ in appearance from the responder location indicator 420. In an implementation, the responder location indicator 420 may represent a static responder location. The static responder location may correspond to a location without navigation mode of the application 225 for the registered responder corresponding to the responder location indicator 420. In contrast, the responder navigation icon 620 may correspond to a dynamic, or evolving, responder location. The dynamic responder location may correspond to a navigation mode of the application 225. The application 225 may switch from the location without navigation mode to the navigation mode in response to a confirmation captured via one or more of the controls 490, 495, 590, 936, and 1110 as shown in FIGS. 4A, 4C, 5A, 9, and 11A. These buttons may enable the registered responder to confirm that he/she is proceeding to and/or arrived at the equipment and/or emergency event location.

The responder navigation icon 620 may move along the map navigation path 440b in approximately real-time to indicate the movement of the registered responder 110 from an initial location (e.g., the location indicator 420 in FIGS. 4A-5B) to the location of the selected medical equipment as indicated by the equipment location indicator 425b. Additionally or alternatively, at the stage 51, the software application 225 may provide a directions message 630. The directions message 630 may be one or more of a visible, audible, or haptic message.

Figure 7:
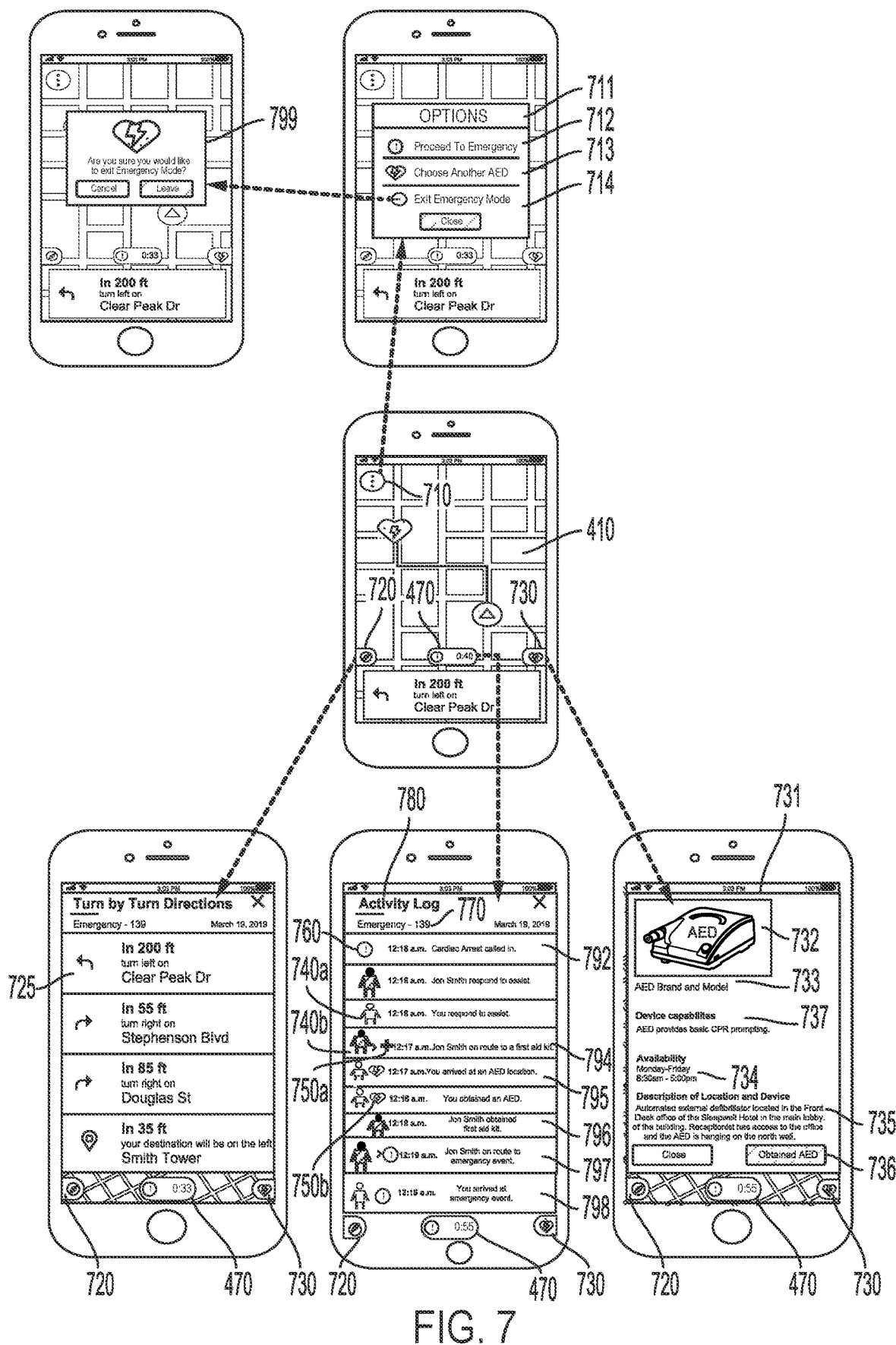

Referring to FIG. 7 with further reference to FIG. 2A, in an implementation, at the stage 51 the software application 225 may provide one or more user selectable icons at the interactive map 410. The one or more user selectable icons may include one or more of a process options icon 710, a directions icon 720, and an equipment information icon 730. In an implementation, the timer 470 may also be a user selectable icon. The user selectable icons may be configured to recognize a touchscreen gesture, such as, for example but not limited to, a tap. The software application 225 may receive the user selection based on the touchscreen gesture.

In an implementation, a user selection of the process options icon 710 may cause the software application 225 to provide an options menu 711. The options menu 711 may include, for example, one or more of an option 712 to proceed to the emergency, an option 713 to change the medical equipment selection, and an exit option 714. The user 110 may select any of these options during the stage 51, i.e., during the provision of directions to the selected medical equipment. In response to the selection from the options menu 711, the method 200a may exit the stage 51 according to one of the dotted line options shown in FIG. 2A. For example, in response to a selection of the option 712 to proceed to the emergency, the method 200a may exit the stage 51 and proceed to the stage 61. As another example, in response to a selection of the option 713 to change the medical equipment selection, the method 200a may exit the stage 51 and return to the stage 43. As a further example, in response to a selection of the exit option 714, the method 200a may exit the stage 51 and proceed to the stage 89 to terminate the assistance request session. In an implementation, referring again to FIG. 7, in response to the selection of the exit option 714, the software application 225 may provide an exit confirmation window 799. If the user 110 confirms the exit request, the software application 225 may terminate the assistance request session. If the user 110 cancels the exit request, the software application 225 may return to the interactive map 410 and continue to provide directions to the selection medical equipment and/or the emergency event.

In an implementation, a selection of the directions icon 720 may cause the software application 225 to provide the turn-by-turn directions window 725. Additionally or alternatively, a selection of the timer 470 may cause the software application 225 to provide a window that includes an activity log 780. Further, a selection of the equipment information icon 730 may cause the software application 225 to provide a window that includes equipment information 731.

One or more of the windows 725, 780, and 731 may include one or more of the timer 470, the directions icon 720, and the equipment information icon 730. Inclusion of the timer 470 with these various windows may cause the registered responder 110 to remain aware of the elapsed time from the emergency assistance request. Based on the elapsed time, the registered responder 110 may increase his/her speed in traversing the route to the medical equipment and/or the emergency event. Further, while viewing any one of the windows 725, 780, and 731, the registered responder 110 may readily switch to any other one of these windows based on the available access to the timer 470 and the icons 720 and 730. The totality of information available from the various window in FIG. 7 may enable the registered responder 110 to adjust his/her activities to improve the emergency response based on this information.

A particular emergency event may be associated with one or more registered responders and/or one or more items and/or types of medical equipment. Accordingly, the activity log 780 may include emergency event identification information 770 for the particular emergency event.

In an implementation, the activity log 780 may include general information 792 about the emergency event that is unassociated with a particular responder and item of medical equipment. This general information may include an emergency event icon 760. For example, the general information may include a time at which the emergency event was reported, a time at which EMS arrived at the emergency event, a time at which the patient was transported or patient care was terminated, etc.

In an implementation, the activity log 780 may provide one or more entries indicative of response status information. These entries may include time-stamps. The response status information may include responder navigation status (e.g., the information 794, 795, 797, and 798) of a particular responder. For example, the responder navigation status may indicate that the particular responder is en route to the medical equipment (e.g., the information 794), arrived at the medical equipment (e.g., the information 795), en route to the emergency event (e.g., the information 797), or arrived at the emergency event (e.g., the information 798). The response status information may include equipment acquisition status (e.g., the information 796). For example, the equipment acquisition status may show that a particular item of equipment has been obtained by a responder and may identify the type of equipment and/or may identify the responder that obtained the equipment. The equipment acquisition status may include a time-stamp to provide a time-stamped indication in the activity log 780 that the registered responder has acquired the selected item of registered medical equipment. The activity log 780 may include this entry in response to a selection of the equipment acquisition control 936 shown for example in FIG. 9. In an implementation, as discussed above, a multiple responders may select respective items of registered medical equipment. For example, a first registered responder may select a first item such as, for example, an external defibrillator, and a second registered responder may select a second item such as, for example, a drug overdose kit, a trauma kit, and/or first aid kit. The activity log may include a time-stamped indication of each selected item of medical equipment and the associated registered responder.

Figure 8:
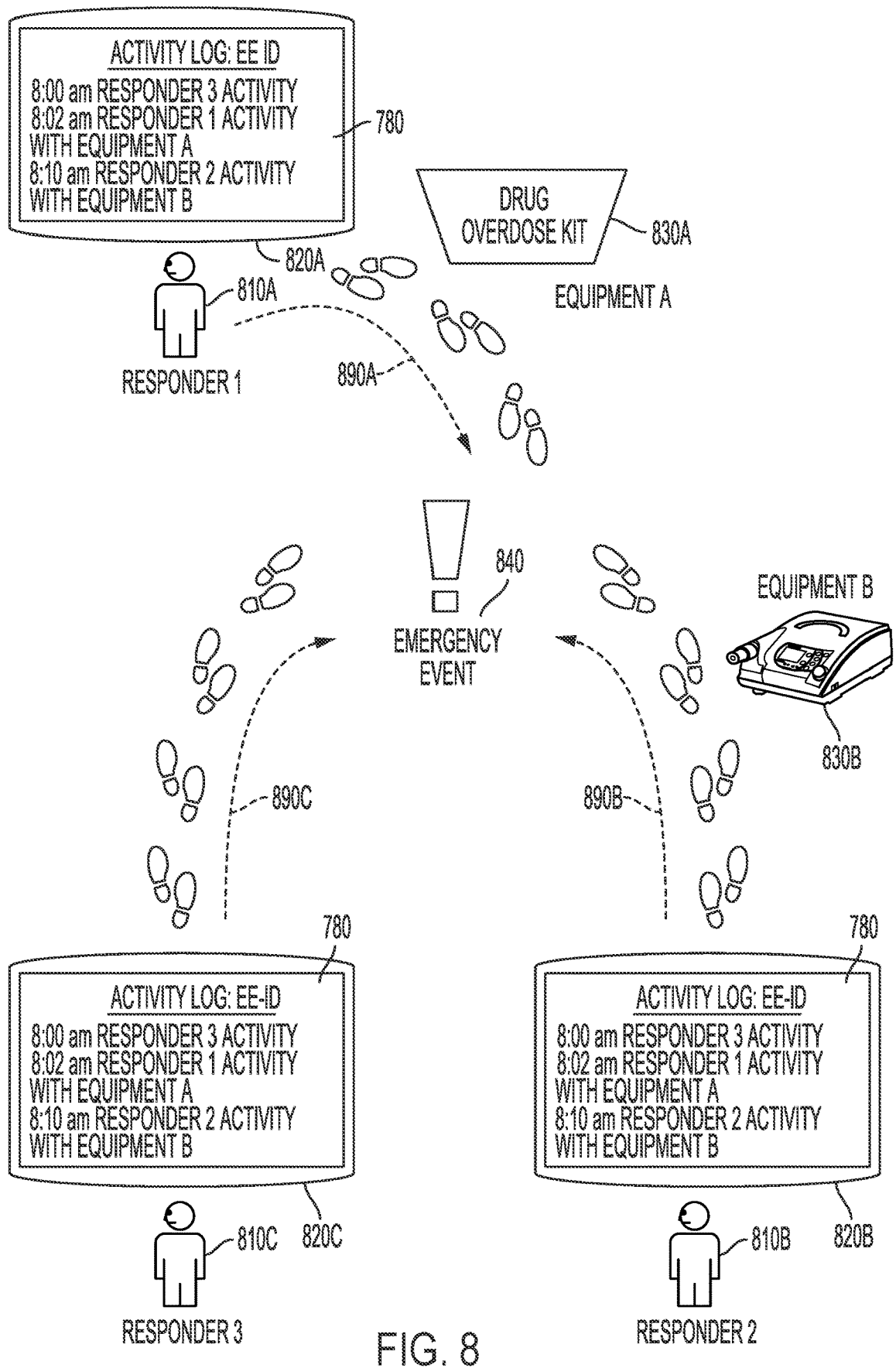
FIG. 8 shows a schematic example of activity logs for a response scenario.

Referring to FIG. 8, a schematic example of activity logs for a response scenario is shown. In an implementation, the activity log 780 may include logged information for one or more responders, one or more items of medical equipment, and/or one or more types of medical equipment. In the example of FIG. 8, three responders 810A, 810B, and 810C (e.g., responder 1, responder 2, and responder 3) are shown. Each of these three responders 810A, 810B, and 810C is associated with a respective mobile device, for example the mobile devices 820A, 820B, and 820C. These three responders are all associated with the emergency event 840. Responder A may take the navigation route 890A to the emergency event 840, responder B may take the navigation route 890B to the emergency event 840, and responder C may take the navigation route 890C to the emergency event 840. En route to the emergency event 840, responder 1 may obtain equipment A 830A and/or responder 2 may obtain equipment B 830B. Equipment A 830A is shown as a drug overdose kit and equipment B 830B is shown as an AED as examples only. In various implementations, these items of medical equipment may be other types of medical equipment and/or supplies and may be the same type and/or different types. Examples of the medical equipment and/or supplies include, but are not limited to, public safety, emergency and/or hospital equipment/supplies such as, but not limited to patient monitors, external defibrillators, ventilation equipment, drug delivery equipment, physiological sensors, fire extinguishers, oxygen tanks, drug overdose kits (e.g., NARCAN® kits), first aid kits, trauma kits, first aid supplies, tourniquet equipment, eye wash equipment/supplies, chemical exposure equipment/supplies, etc.

Each of the mobile devices 820A, 820B, and 820C may include the software application 225. The software application 225 may provide the activity log 780. The activity log 780 for the emergency event may include an identification of the emergency event (EE-ID). Further, the activity log 780 may provide information on activities of one or more of the responders involved with the emergency event 840. In the example of FIG. 8, the activity log 780 includes the activities for all of the responders 810A, 810B, and 810C. For example, when any one of these responders enters, changes, and/or confirms a status, the activity log 780 available to all of the responders associated with the emergency event 840 may automatically update to include the entered, changed, and/or confirmed status information. As another example, the software application 225 may determine a navigation status or equipment acquisition status for one or more of the responders. This status may be a current status and the software application 225 may include this determined status in the activity log 780. Further, the software application 225 may automatically update the activity log 780 in response to changes in the navigation status and/or equipment acquisition status for one or more of the registered responders. As shown, for example, in FIG. 8, the activity log 780 available on all three mobile devices 820A, 820B, and 820C show activities for the group of responders. The activity log 780 is not limited to activities of the responder associated with the mobile device on which the activity log 780 is displayed. Thus, the software application 225 may automatically provide status information for each member of a group of registered responders to each other member of the group of registered responders. The status information may include one or more of the response status (e.g., via the accept button 320 shown in FIG. 3), the navigation status (e.g., via one or more of the buttons 490, 495, 590, 936, and 1110 as shown in FIGS. 4A, 4C, 5A, 9, and 11) and/or the equipment acquisition status (e.g., via the equipment acquisition control 936 shown in FIG. 7). The equipment acquisition status may also provide a navigation status as acquisition of the emergency equipment may indicate that the registered responder has arrived at the registered medical equipment. The navigation status may further include an automatic update when the registered responder reaches the location of the emergency event as described below with regard to FIG. 10B.

In order to for the user 110 to easily associate the information in the activity log 780 with the appropriate responder, each responder icon 740a and 740b may include an appearance aspect that is different from each other of the icons. For example, each responder icon may have a different color. In an implementation, the graphic icons in the activity log may match an appearance (e.g., color, shape, etc.) of graphic icons used as location indicators on the interactive map 410. For example, the shape of the responder icons 740a and 740b may match the shape of the responder location indicator 420. The matching shape may provide continuity between windows of the software application 225 to reduce user confusion which could degrade the quality of the emergency response. Similarly, in an implementation, the emergency event icon 760 may match an appearance of the emergency event location indicator 423 and the one or more equipment icons 750a and 750b may match the shape of the equipment location indicators 425a, 425b, and 425c based on the type of medical equipment. In the example of FIG. 7, a "+" icon represents a first aid kit or trauma kit and a heart shaped icon represents an AED.

In an implementation, the interactive map 410 may include multiple emergency events and each emergency event may correspond to an associated activity log 780. In an implementation, the interactive map 410 may include multiple timer icons with each timer icon located next to an emergency event location indicator. The user 110 may tap the timer icon for the particular emergency event in order to access the associated activity log.

In an implementation, the equipment information window 731 may include one or more of photographic image 732 of the medical equipment, brand and/or model information 733, equipment availability information 734, a written description 735 of the location and/or the equipment and/or device capabilities 737. The equipment availability information 734 may be time availability that includes days and/or times that the equipment is available for procurement by the responder. The description 735 and/or the device capabilities 737 may enumerate device capabilities that may be of particular interest to the responder. For example, such capabilities may include basic CPR prompting and/or advanced CPR feedback. In an implementation, the equipment information window 731 may include an equipment acquisition control 736. The registered responder 110 may provide confirmation to the software application 225 that he/she has obtained the medical equipment via the equipment acquisition control 736. For example, the registered responder 110 may tap or press the equipment acquisition control 736. In an implementation, in response to receiving the confirmation that the registered responder 110 has obtained the medical equipment, the software application 225 may update the equipment acquisition information 794 in the activity log 780 for one or more registered responders. In an implementation, the software application 225 may determine that the navigation status of the registered responder is that the registered responder has arrived at and is co-located with the equipment based on the input to the equipment acquisition control 936 and/or based on the tracked location of the computing device 220.

In an implementation, the responder may access the equipment information window 731 via the equipment information icon 730 and/or via the equipment location indicators (e.g., the indicator 425a, 425b, 425c, 915, 1970, 1980, and/or 1990). In an implementation, selection of the equipment location indicator may automatically cause display of the information window 731. Alternatively or additionally, the responder may select an item of equipment via a first touchscreen gesture (e.g., a single tap on the location indicator) and may request the equipment information via a second touchscreen gesture (e.g., a double tap or press on the location indicator). The responder may base a decision to select the item of equipment based on this equipment information. For example, the responder may choose a brand of equipment with which the responder is familiar or has previous training or experience. As another example, the responder may choose the equipment based on the device capabilities. The device may provide basic and/or advanced prompting during use and the responder may select the device that provides a desired level of prompting. In an implementation, an appearance of the equipment location indicators on the interactive map 410 may indicate the brand and/or the device capabilities. Alternatively or additionally, the interactive map 410 may filter the equipment location indicators based on a training level or device preference provided by the responder during registration.

Referring again to FIG. 2A, at stage 53, the method 200a includes receiving user input confirming that the registered responder obtained the medical equipment previously selected at the stage 43 and for which navigation directions were provided at the stage 51. For example, the equipment information window 731 may further include an equipment acquisition control 936. The registered responder 110 may provide confirmation to the software application 225 that he/she has obtained the medical equipment via the equipment acquisition control 936. For example, the registered responder 110 may tap or press the equipment acquisition control 936. In an implementation, in response to receiving the confirmation that the registered responder 110 has obtained the medical equipment, the software application 225 may update the equipment acquisition information 794 in the activity log 780 for one or more registered responders. In an implementation, the software application 225 may determine that the navigation status of the registered responder is that the registered responder has arrived at and is co-located with the equipment based on the input to the equipment acquisition control 936 and/or based on the tracked location of the computing device 220.

In an implementation, when the location of the computing device 220 approximately matches the location of the selected medical equipment (e.g., the computing device 220 and the medical equipment 230 are co-located) and/or when the computing device 220 is within a pre-determined approach distance from the medical equipment 230 (e.g., within 1 m, 2 m, 5 m, 10 m, 25 m, 50 m, or 100 m), the software application 225 may automatically provide the equipment information window 731. Since the equipment information window 731 provides descriptions and/or images of the medical equipment and/or the storage location, this window may facilitate acquisition of the medical equipment 230 by the registered responder 110. Such facilitation may reduce the time it takes for the registered responder 110 to reach the victim with the medical equipment 230 and thereby improve a patient's chance of survival and the efficacy of the responsive care.

Referring to FIG. 9, an example of an equipment acquisition control is shown. In an implementation, in addition to or as an alternative to the equipment information window 731, the software application 225 may provide an equipment acquisition control 936 at the interactive map for the registered responder to confirm acquisition of the medical equipment. The software application 225 may provide the equipment acquisition control 936 when the registered responder is co-located with the medical equipment 230. In the example of FIG. 9, the medical equipment location indicator 915 (e.g., a drop icon that may represent eye wash or chemical wash equipment/supplies) is proximate to the responder navigation icon 620. The software application 225 may determine that the location of the computing device 220 associated with the registered responder 110 approximately matches the location of the selected medical equipment when the tracked location of the computing device 220 is within a pre-determined distance from the location of the medical equipment. For example, the software application 225 may consider the computing device 220 to be co-located with the medical equipment when the two locations are within 1, 2, 3, 5, 10, 20, or 50 meters of one another. In various implementations, the medical equipment location may be an accurate location, such as with geographic coordinates, or may be an inaccurate location such as a street address, a location description, etc. For the inaccurate location, the software application 225 may estimate or otherwise assign coordinates to the equipment location.

Figure 10A:
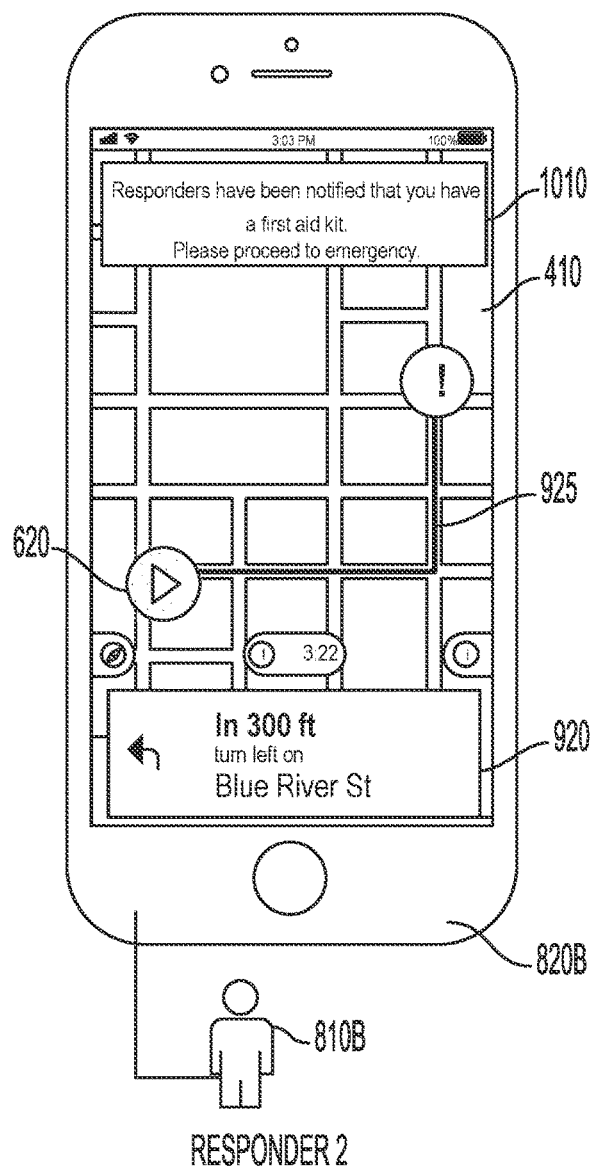
FIGS. 10A and 10B show examples of navigation and confirmation features of the software application.
Figure 10B:
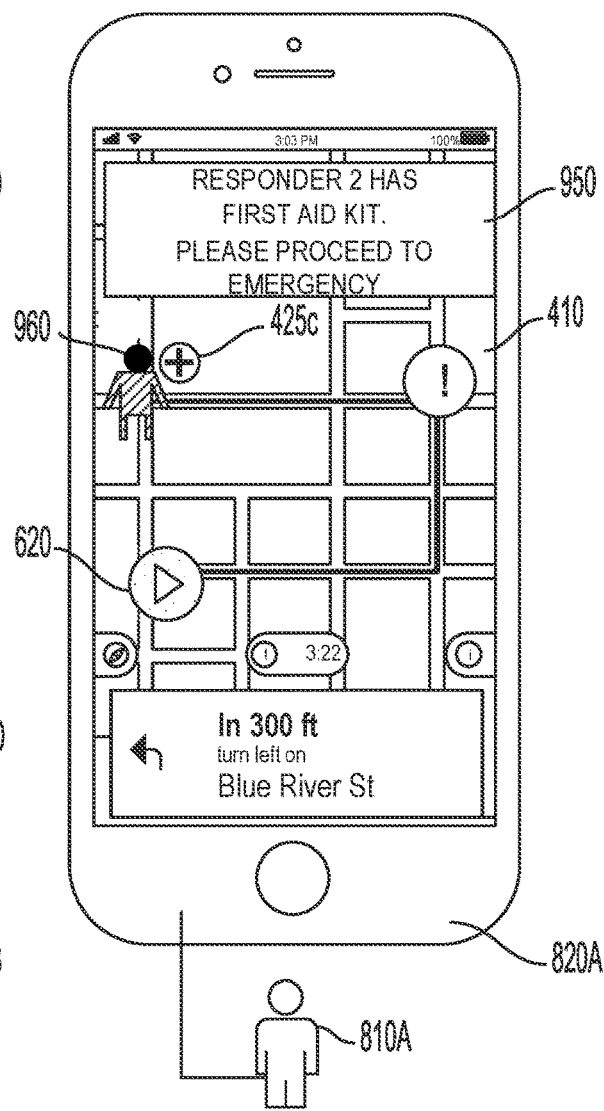

Referring to FIGS. 10A and 10B, examples of navigation and confirmation features of the software application are shown. For instance, as shown in FIG. 10A, once the software application 225 confirms acquisition of the selected equipment (e.g., via user input and/or automatically based, for example on location as described above), the software application may provide a responder notification message 1010. The responder notification message 1010 may indicate that the software application 225 has provided the equipment acquisition information to other responders associated with the emergency event. For example, the software application 225 may update the activity log 780. In an implementation, the responder notification message 1010 may indicate a type of medical equipment, in this example a first aid kit.

Referring again to FIG. 2A, with further reference to FIGS. 10A and 10B, at stage 55, the method 200a includes providing directions from the medical equipment location to the emergency event location. For example, the software application 225 may provide text directions 920 and/or a graphic representation 925 of a navigable route. In an implementation, the responder navigation icon 620 moves along the graphic representation 925 of the navigable route. The responder navigation icon 620 corresponds to a position of the responder associated with the mobile device on which the interactive map 410 is displayed. For example, if the mobile device in FIG. 10A is the device 820B in FIG. 8, then the responder navigation icon 620 corresponds to a location of the registered responder 810B (i.e., responder 2) in FIG. 8. Once responder 2 acquires the medical equipment, then the software application 225 notifies the other responders, for example, responder 1 and responder 3 in FIG. 8.

Referring to FIG. 10B, an example of the interactive map 410 for a responder receiving a notification about another responder is shown. For example, if the mobile device in FIG. 10B is the device 820A in FIG. 8, then the responder navigation icon 620 in FIG. 10B corresponds to a location of the registered responder 810A (i.e., responder 1) in FIG. 8. Once responder 2 acquires the medical equipment, then the software application notifies the other responders. FIG. 10B shows an example of an equipment acquisition message 950 that indicates that another responder has acquired the medical equipment. In an implementation, the equipment acquisition message 950 may indicate a type of medical equipment, in this example a first aid kit. For example, if the mobile device 820A in FIG. 10B corresponds to responder 1, then the equipment acquisition message 950 may indicate that responder 2 has acquired the medical equipment. In an implementation, the software application 225 may provide a responder location indicator 960. The responder location indicator 960 may correspond to a location of a registered responder unassociated with the mobile device on which the responder location indicator 960 is displayed. In this example, the responder location indicator 960 may correspond to responder 2 since responder 1 is associated with the mobile device 820A. In an implementation, the software application 225 may further display the equipment location indicator 425c that corresponds to the location of the medical equipment 830B obtained by responder 2.

Figure 11B:
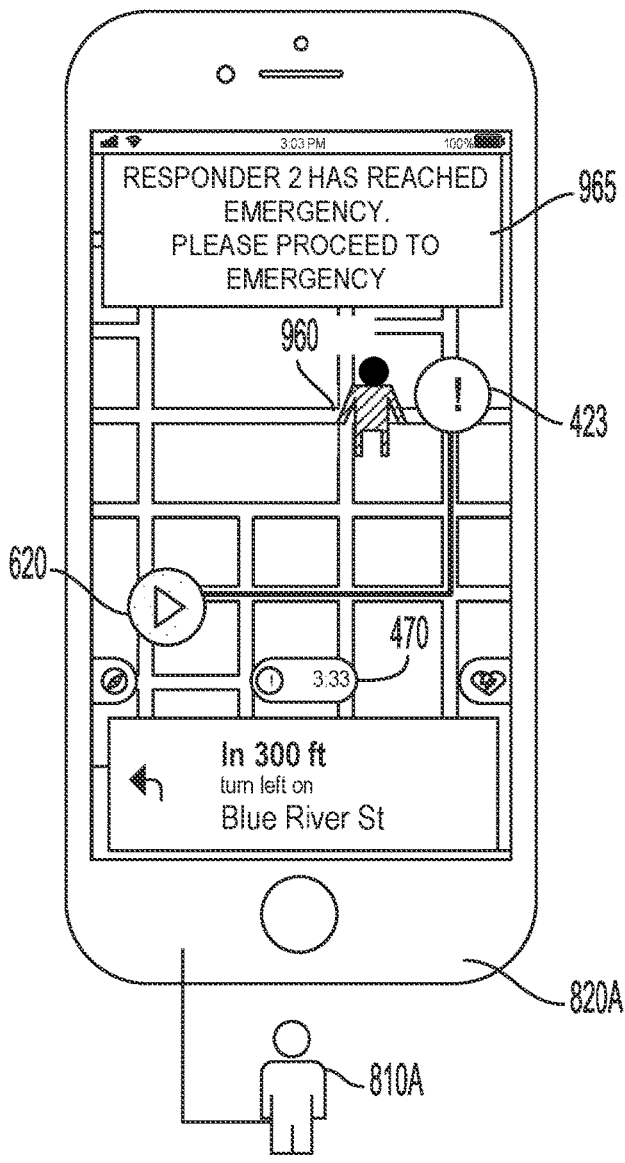

Referring again to FIG. 2A, with further reference to FIGS. 11A and 11B, at stage 71, the method 200a includes automatically providing an update that notifies one or more registered responders that at least one of the one or more registered responders has arrived at the emergency event location. The method 200a may arrive at the stage 71 either from the stage 55 (e.g., if the responder selected medical equipment at the stage 43) or from the stage 61 (e.g., if the responder declined medical equipment at the stage 43). As shown for example in FIG. 11A, when the registered responder 110 arrives at the emergency event location, the responder navigation icon 620 may be proximate to and/or overlap with the location indicator 423 for the location of the emergency event. The software application 225 may determine that the location of the computing device 220 associated with the registered responder 110 approximately matches the emergency event location when the tracked location of the mobile device is within a location measurement accuracy limit of the emergency event location. For example, the software application 225 may consider the computing device 220 to be co-located with the emergency event when the two locations are within 1, 2, 3, 5, 10, 20, or 50 meters of one another. In an implementation, the software application 225 may determine that the computing device 220 is co-located with the emergency event in response to a user input to the arrive-at-emergency control 1110 and/or based on the tracked location of the computing device 220. For example, the arrive-at-emergency control 1110 may capture a user touchscreen gesture, such as, for example, a tap, to confirm that the registered responder 110 has arrived at the emergency event.

The responder navigation icon 620 corresponds to a position of the responder associated with the mobile device on which the interactive map 410 is displayed. For example, if the mobile device in FIG. 11A is the device 820B in FIG. 8, then the responder navigation icon 620 corresponds to a location of the registered responder 810B (i.e., responder 2) in FIG. 8. Once responder 2 arrives at the emergency event, then the software application 225 notifies the other responders, for example, responder 1 and responder 3 in FIG. 8. The software application 225 may provide a notification message 964 indicating that other responders have been notified and/or providing instructions for the responder that has arrived at the emergency event.

Referring to FIG. 11B, an example of the interactive map 410 for a responder receiving a notification about another responder is shown. For example, if the mobile device in FIG. 10B is the device 820A in FIG. 8, then the responder navigation icon 620 in FIG. 11B corresponds to a location of the registered responder 810A (i.e., responder 1) in FIG. 8. Once responder 2 arrives at the emergency event, then the software application 225 notifies the other responders. FIG. 11B shows an example of a notification message 965 that indicates that another responder has arrived at the emergency event. For example, if the mobile device 820A in FIG. 11B corresponds to responder 1, then the notification message 964 may indicate that responder 2 has arrived at the emergency event. In an implementation, the software application 225 may provide a responder location indicator 960. The responder location indicator 960 may correspond to a location of a responder unassociated with the mobile device on which the responder location indicator 960 is displayed. In this example, the responder location indicator 960 may correspond to responder 2 since responder 1 is associated with the mobile device 820A. The software application 225 may display the responder location indicator 960 as proximate to and/or overlapping the location indicator 423. As shown for example in FIGS. 11A and 11B with further reference to FIG. 8, in an implementation, the timer 470 may display a same time on all the mobile devices (e.g., 820A, 820B, 820C) associated with responders (e.g., 810A, 810B, 810C) to a same emergency event 840.

Figure 12:
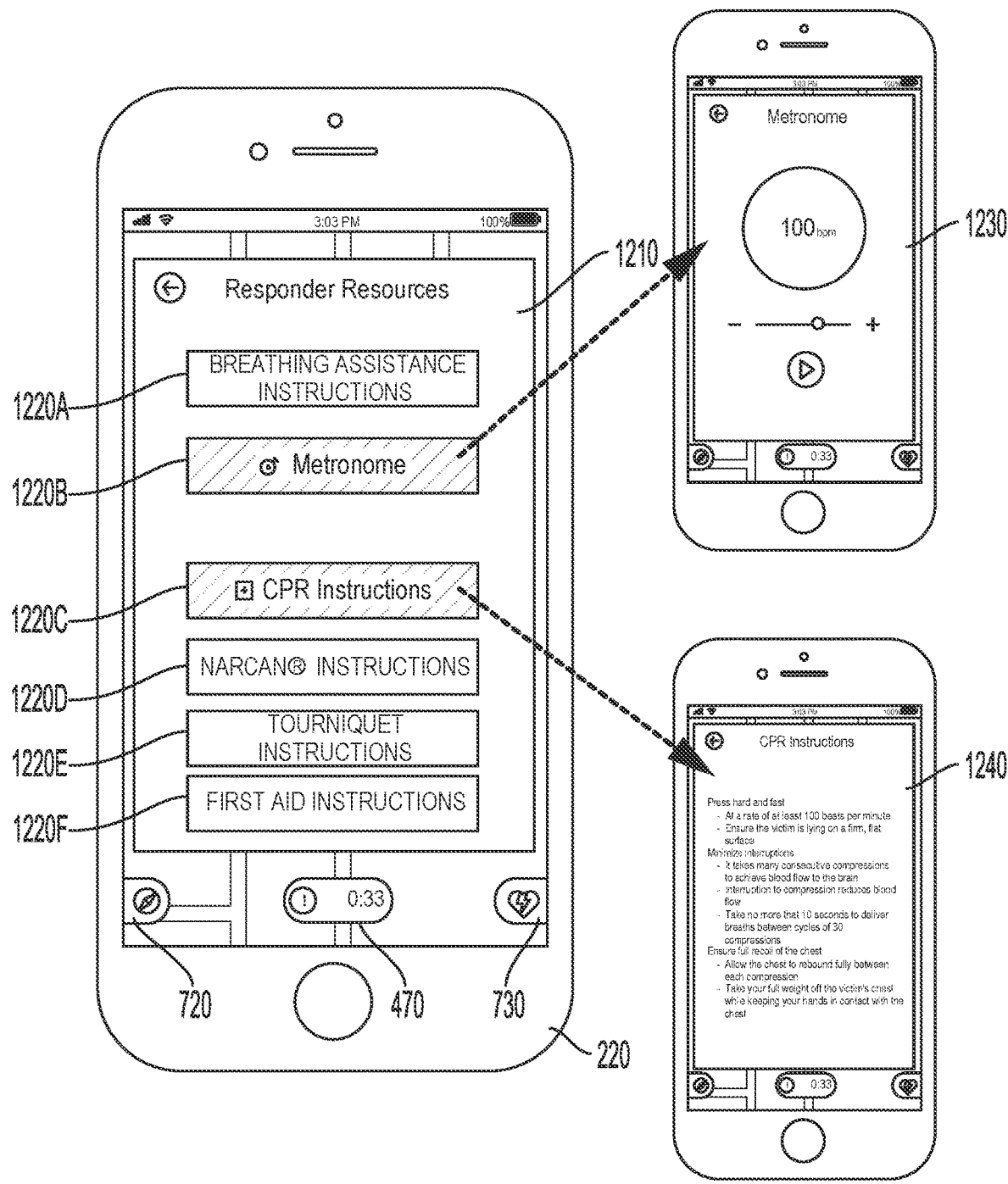
FIG. 12 shows examples of user assistance screens of the software application.

Referring to FIG. 12, examples of user assistance screens of the software application are shown. In an implementation, the registered responder 110 may select an information button 930 on the interactive map 410 as shown for example in FIG. 11A. In response to selection of the information button 930, the software application 225 may provide a responder resources window 1210. The responder resources window 1210 may have one or more user selectable options 1220A, 1220B, 1220C, 1220D, 1220E, and 1220F. Selection of one or more of these options may cause the software application 225 to provide a new window with instructions, prompts, or other information for the responder. For example, selection of the option 1220B, the metronome, may open a metronome window 1230 that may provide a metronome for chest compressions. As another example, selection of the option 1220C, the CPR instructions, may open a CPR instruction window 1240 that may instruct the user on how to perform CPR. In an implementation, the software application 225 may provide audible and/or haptic information in response to the selection of one of the options in the responder resources 1210. The software application 225 may provide the audible and/or haptic information in addition to or as an alternative to providing another window, such as CPR instruction window 1240. The responder resource window 1210 may include icons 720 and/or 730 that link to navigation and/or medical equipment information. The responder resource window 1210 may include the timer 470.

In an implementation, the software application 225 may filter the selectable options provided in the responder resources window 1210 based on the selected medical equipment. For example, referring again to FIG. 8, if responder 1 is associated with the computing device 220, then the responder resources window 1210 may only include selectable option 1220D for NARCAN® instructions since responder 1 selected a drug overdose kit 830A. Similarly, if responder 2 is associated with the computing device 220, then the responder resources window 1210 may only include selectable options 1220B and 1220C for the metronome and CPR instructions since responder 2 selected an AED 830B. In an implementation, the software application 225 may designate one or more of the selectable options in the responder resources window 1210 as default options and then provide additional options based on the type of medical equipment. For example, the responder resource window 1210 for all responders may include the CPR instruction option 1220C and, in addition, for the responder with the drug overdose kit 830A, the responder resource window 1210 may include a NARCAN® instruction option 1220D. In an implementation, the options provided in the responder resources window may be a user configurable option. For example, the registered responder 110 may register as a CPR provider only and exclude first aid from his/her skill set. In this case, the registered responder 110 may configure the software application 225 to provide only the CPR instruction and metronome options. In an implementation, the software application 225 may customize the responder resources window 1210 based on registration information provided by the registered responder 110.

Figure 13A:
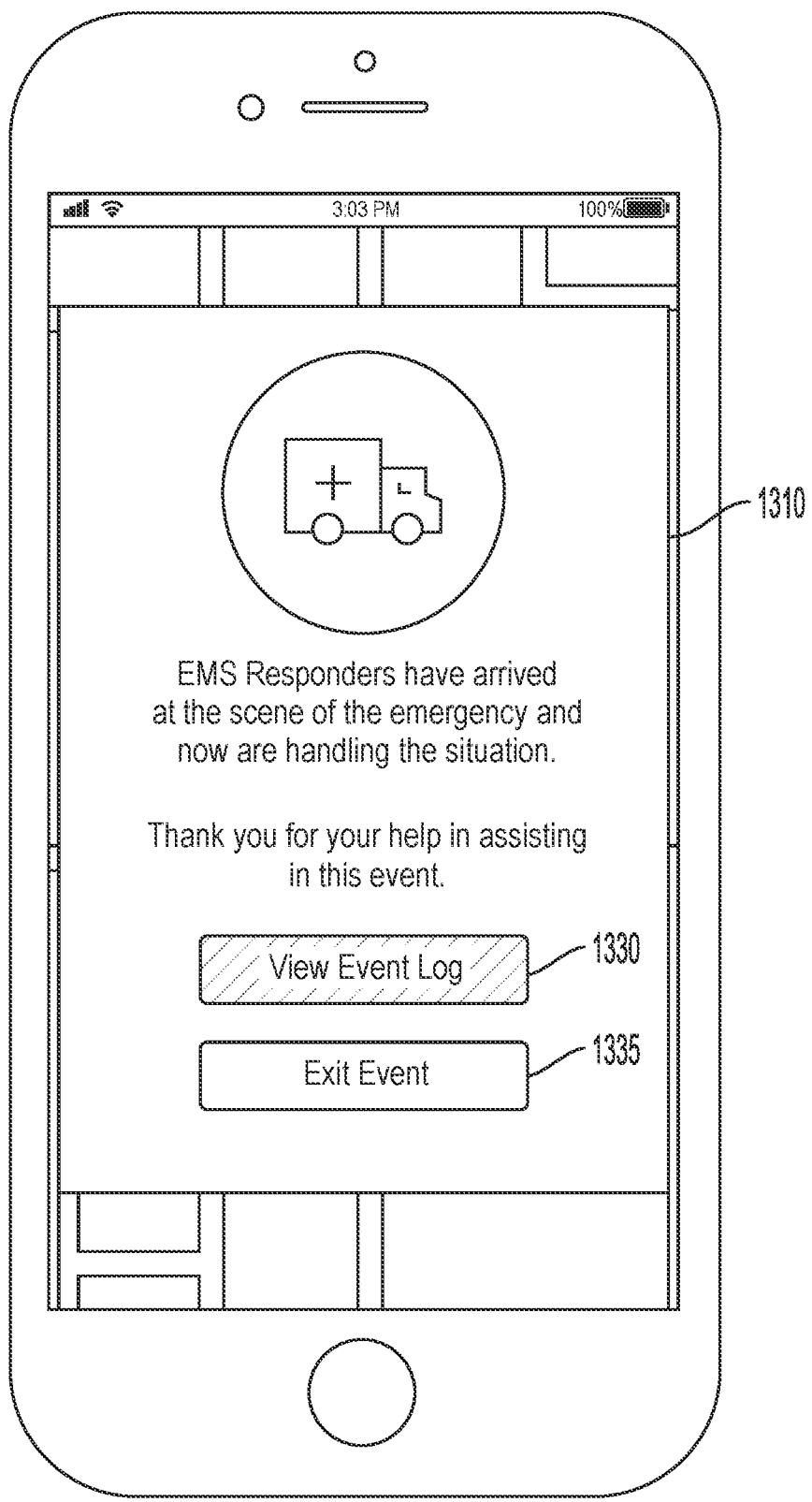
FIG. 13A shows an example of an end of event screen of the software application.

Referring again to FIG. 2A with further reference to FIG. 13A, at stage 73, the method 200a includes providing an end of event screen when EMS responders arrive at the emergency event. For example, referring to FIG. 13A, the software application 225 may provide the end of event screen 1310. In an implementation, the management system 270 may receive a notification from the emergency dispatch service 125 and/or the EMS agency 130 that EMS responders have arrived at the emergency event. In response, the management system 270 may notify one or more registered responders associated with the emergency event that the EMS responders have arrived. In an implementation, the software application 225 may provide the end of event screen 1310 to registered responders located at the emergency event along with registered responders located elsewhere, for example, still en route to the emergency event.

In an implementation, the end of event screen 1310 may provide various selectable user options such as, for example, an activity log button 1330 and/or an exit event button 1335. Selection of the activity log button 1330 may cause the software application 225 to provide the activity log 780.

In response to selection of the exit event button 1335, the method 200a proceeds to the stage 89. At the stage 89, the software application 225 ends the assistance request session. The software application may initiate a new assistance request session upon receipt of a new emergency assistance request by the computing device 220. In an implementation, the method 200a may proceed to the stage 89 due to expiration of a time limit in the absence of a user input to the end of event screen 1310. For example, the software application 225 may initialize a timer when EMS responders arrive at the emergency event (e.g., based on information received by the software application from the emergency dispatch service 125 and/or the EMS agency 130). Alternatively, the software application 225 may initialize the timer when the responder arrives on scene (e.g., based on a location of the mobile device 220). The duration of the timer may be, for example, 5-60 minutes. If the timer expires before a user ends the event with the exit event button 1335, the software application 225 may automatically end the event. Often, the scene of an emergency is chaotic and it is possible for the responder to lose track of time and/or otherwise get caught up in the events on scene and forget to end the event. With the timer, the software application 225 may automatically close the event for the particular responder. This may enable the software application 225 to provide a notification to that same responder for an additional event.

Figure 13B:
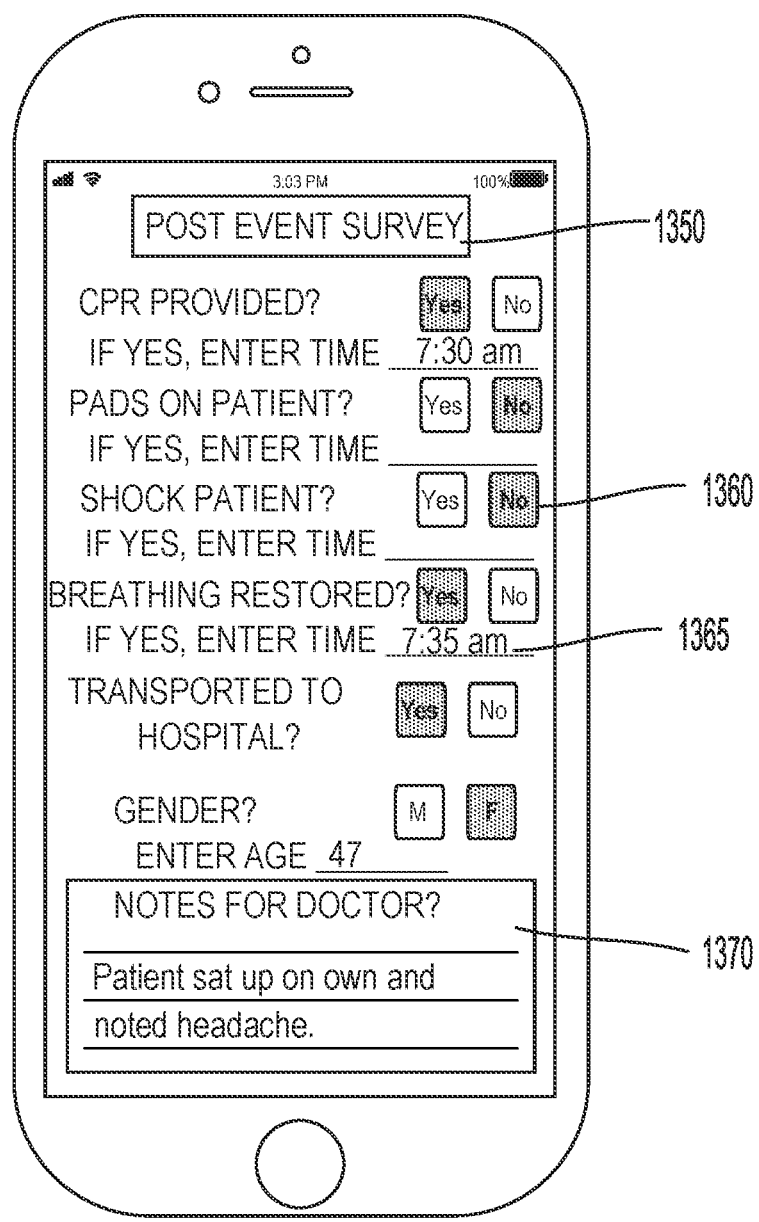
FIG. 13B shows an example of a post-event survey window of the software application.

Referring to FIG. 13B, an example of a post-event survey window of the software application is shown. In an implementation, once the registered responder exits the assistance request session, the software application 225 may provide a post-event survey window 1350. The post-event survey window 1350 may enable the registered responder to provide information about the event. For example, the survey window 1350 may provide questions with response controls 1360. The survey window 1350 may also include fillable fields 1365 for event times and/or a fillable field 1370 for notes. The survey details provided in FIG. 13B pertain to CPR as an example only and questions/details about other types of emergency or medical treatment are within the scope of the disclosure. The notes may be for a doctor, EMS worker, nurse, and/or other personnel with access to the emergency event information. In an implementation, the management system 270 may send the information provided via the survey window 1350 to the EMS agency 130 and/or to a third party (e.g., via the network 250) for review and/or insertion into a patient care record for the emergency event. In an implementation, the EMS agency 130 may link their patient care record system to at least a portion of the management system 270 to access the information provided via the survey window 1350.

Figure 2B:
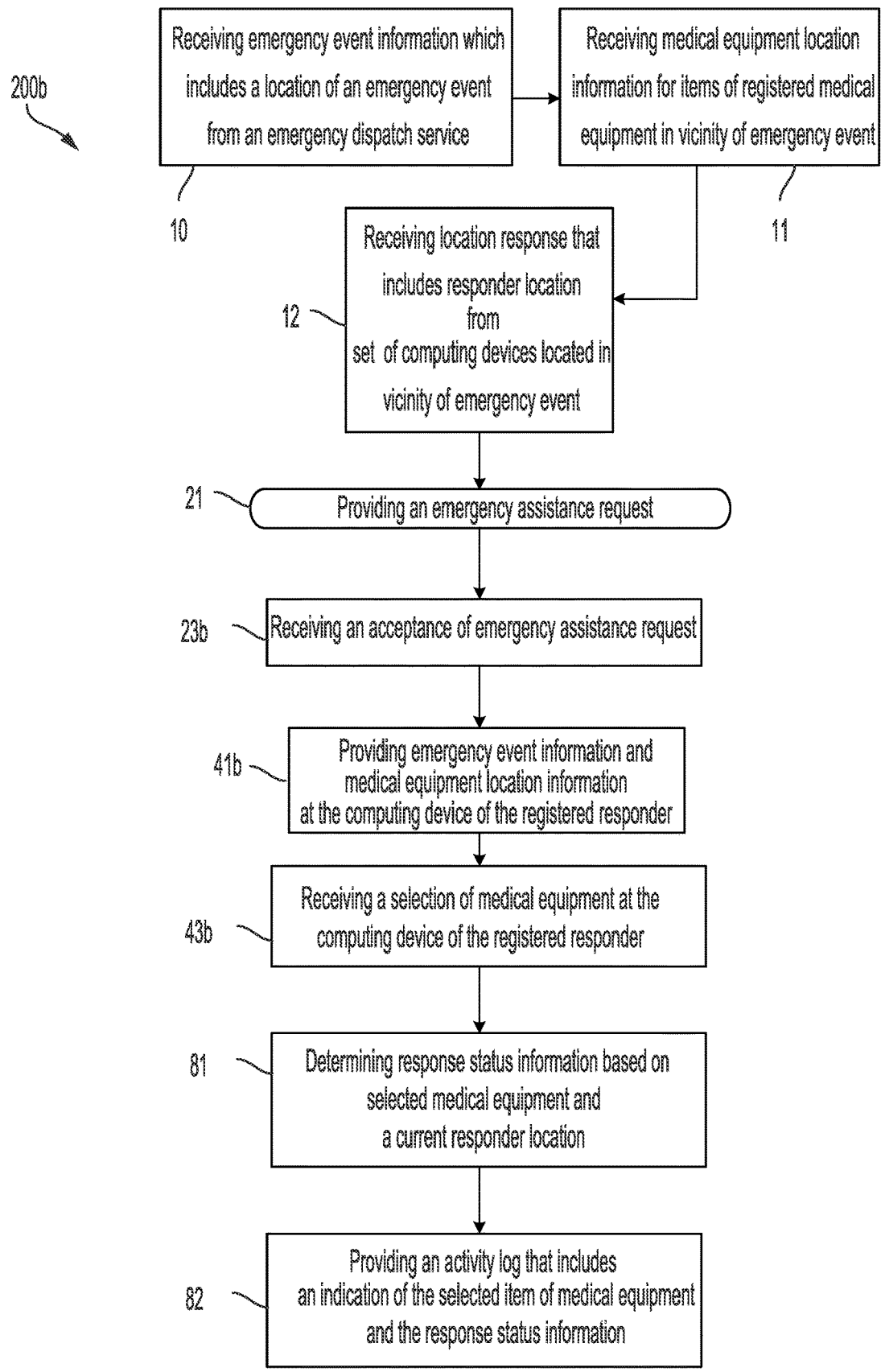

Referring to FIG. 2B, a block diagram of a computer-implemented method for providing responders and equipment to an emergency event is shown. The method 200b is, however, an example only and not limiting. The method 200b can be altered, e.g., by having stages added, removed, rearranged, combined, and/or performed concurrently.

At the stage 10, the method 200b includes receiving emergency event information which includes a location of an emergency event from an emergency dispatch service. For example, the management system 270 may receive the emergency event information 150 from the emergency dispatch service 125, as described above with regard to FIG. 2A. For example, the computing device 220 associated with the registered responder 110 may receive the emergency assistance request from the management system 270 via the network(s) 250. The management system 270 may provide the emergency assistance request in response to receiving emergency event information 150 from an emergency dispatch service 125. For example, a victim, bystander, or other observer of or witness to an emergency event may notify the emergency dispatch service (e.g., an emergency dispatch office or other a public safety answering point accessible via a "9-1-1" call). The emergency dispatch service 125 may push out emergency event information 150 to one or more emergency medical services (EMS) organizations (e.g., EMS 130 as shown in FIG. 1). The emergency event information 150 may include a code that indicates a type of emergency (e.g., a physical condition of an emergency victim such as cardiac arrest, drug overdose, chemical exposure, trauma, bleeding, breathing difficulty, etc.) and a location of the emergency event. The emergency event information 150 include may further include victim information (e.g., demographic information such as age, gender, physical description information, etc.).

The emergency dispatch service 125 may concurrently and automatically send the emergency event information 150 to the management system 270. The emergency event information 150 includes at least a location of the emergency event and may include further information about the emergency event (e.g., the type of event, equipment needed, etc.). The emergency dispatch service 125 may time-stamp the emergency event information 150 and the time of transmission, the time of receipt by the EMS agency 130 and the time of receipt by the management system 270 may all be the time indicated by the time-stamp.

At stage 11, the method 200b may include receiving medical equipment location information for items of registered medical equipment in a vicinity of the emergency event, as described above with regard to FIG. 2A. As described herein with regard to the management system 270, the management system 270 may determine medical equipment location information based on medical equipment information stored in the equipment database 280.

At stage 12, the method 200b may include receiving a location response from a group of computing devices located in the vicinity of the emergency event and associated with respective registered responders, as described above with regard to FIG. 2A. In order to identify registered responders in a vicinity of the emergency event, the management system 270 may push the emergency event information to one or more computing devices (e.g., the computing device 220) associated with registered responders in the responder database 214 and that include the application 225. For example, the computing devices may be cellular telephones and the responder database 214 may include a cellular telephone number for each registered responder. Upon receipt of the emergency event information, the application 225 may compare the location of the computing device (e.g., as determined via one or more of the SPS satellites 290, the outdoor radio transmitters 296, and/or the indoor radio transmitters 295) with the emergency event location. For each computing device, if the comparison indicates that the computing device is in a vicinity of the emergency event, then the application 225 identifies that computing device to the management system 270 as being within a pre-determined distance of the emergency event and sends a location response to the management system 270. The location response may include the current location of the computing device which is also the current location of the registered responder associated with the computing device. Thus, the location response includes responder location information. The management system 270 may then provide the emergency assistance request to the one or more computing devices identified as being located in the vicinity of the emergency event. In an implementation, the management system 270 may only send the emergency assistance request to this set of computing devices and may not send the emergency assistance request to computing devices that are not in this set and therefore not identified as being in the vicinity of the emergency event.

At the stage 21, the method 200b includes providing an emergency assistance request. The stage 21 in the method 200b is substantially as described for the stage 21 of the method 200a in FIG. 2A.

At stage 23b, the method 200b includes receiving an acceptance of the emergency assistance request. This stage is substantially as described with regard to the stage 23 of the method 200a for the case in which the registered responder accepts the request.

At stage 41b, the method 200b includes providing the emergency event information and the medical equipment location information at the computing device associated with the registered responder. This stage is substantially as described with regard to the stage 41 of the method 200a for the case in which medical equipment is available for selection at the stage 25.

At stage 43b, the method 200b includes receiving a selection of medical equipment at the computing device of the registered responder. The selection of medical equipment by the registered responder is described in detail above with regard to the stage 43 in FIG. 2A and the user interface examples in FIGS. 4B, 5A, and 5C.

At stage 81, the method 200b includes determining response status information based on selected medical equipment and a current responder location. As discussed above at least with regard to FIG. 7, the response status information may include the responder navigation status and/or the equipment acquisition status. In various implementation, the software application 225 may determine the response status information based on the tracked location of the computing device 220 and/or user selection of various controls, for example the proceed-to-emergency control 495 (e.g., as shown in FIG. 4A), the proceed-to-equipment control 590 (e.g., as shown in FIG. 5A), the equipment acquisition control 936 (e.g., as shown in FIG. 9), and the arrive-at-emergency control 1110 (e.g., as shown in FIG. 11A).

At stage 82, the method 200b includes providing an activity log that includes an indication of the selected item of medical equipment and the response status information. For example, the activity log 780 may include the response status information determined at the stage 81. The activity log 780 is discussed above in detail with regard to FIGS. 7 and 8.

Figure 2C:
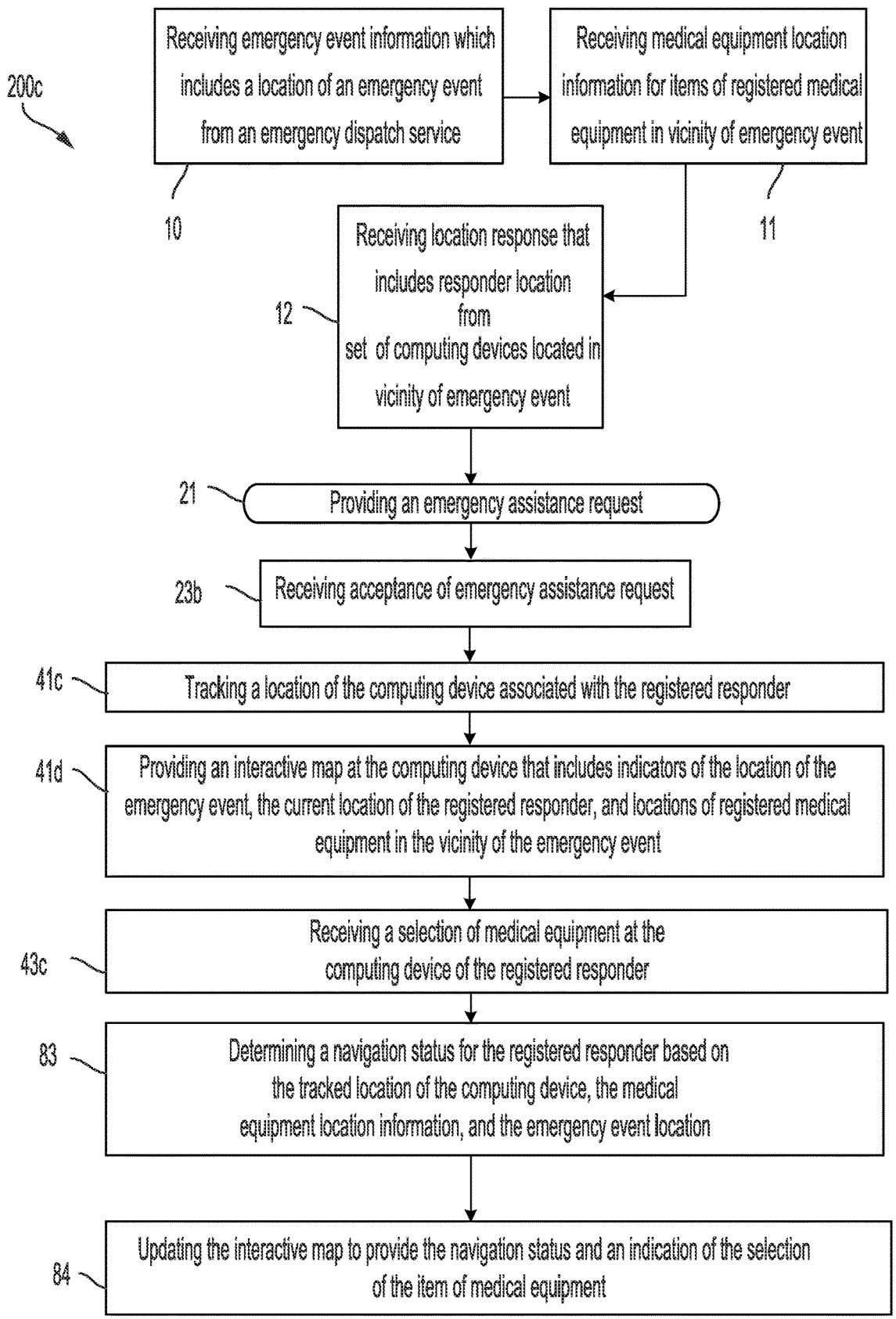

Referring to FIG. 2C, a block diagram of a computer-implemented method for providing responders and equipment to an emergency event is shown. The method 200c is, however, an example only and not limiting. The method 200c can be altered, e.g., by having stages added, removed, rearranged, combined, and/or performed concurrently. The stages 10, 11, 12, 21, and 23b are substantially as described with regard to FIG. 2B.

At stages 41c and 41d, the method 200c includes, in response to the acceptance of the emergency assistance request, tracking a location of the computing device associated with the registered responder and providing an interactive map at the computing device that includes an indicator of the location of the emergency evet, an indicator of a current location of the registered responder based on the tracked location of the computing device, and location indicators for the times of registered medical equipment located in the vicinity of the emergency event.

As discussed above, following the acceptance of the emergency assistance request, the registered responder 110 has entered the assistance request session for the emergency event. During the session, the management system 270 may automatically track the location of the computing device 220 in order to evaluate the navigation status of the registered responder. The tracking may be continuous or periodic. For example, the tracked location of the computing device may indicate that the registered responder is en route to an item of medical equipment, en route to the emergency event, arrived at (e.g., co-located with) the item of medical equipment, or arrived at (e.g., co-located with) the emergency event. Once the registered responder 110 exits the session (e.g., at the stage 89 in FIG. 2A), the management system 270 may automatically terminate the location tracking. The interactive map 410 provided at the stage 41d is described in detail above at least with regard to FIGS. 4B, 4C, 5A, and 5B.

At stage 43c, the method 200c includes receiving a selection of medical equipment at the computing device of the registered responder. The management system 270 and the software application 225 may provide equipment options to the registered responder via the interactive map 410. The software application 225 enables the registered responder to select an item of equipment. In this way, the responder may tailor the equipment selection based on their emergency response capabilities and/or credentials and/or a general comfort level with a particular type of care. Also, the responder can determine which equipment is most readily accessible based on a preferred navigation route, a mode of transport, and/or a personal knowledge of the area of the emergency event. Such information may be unavailable to a remote dispatcher, for example, or other central coordinator of an emergency response. For example, the responder may be familiar with an area surrounding a workplace and know that building scaffolding is temporarily blocking a certain sidewalk. With this knowledge, they may select an AED, for example, on a route that excludes the particular sidewalk.

At stage 83, the method 200c includes determining a navigation status for the registered responder based on the tracked location of the computing device, the medical equipment location information, and the location of the emergency event. For example, the tracked location of the computing device may indicate that the registered responder is en route to an item of medical equipment, en route to the emergency event, arrived at the item of medical equipment, or arrived at the emergency event. Further, the software application 225 may determine the navigation status of the registered responder 110 from input to a navigation control in addition to or as an alternative to tracking the location of the computing device 220. For example, as described herein, the navigation control may include one or more of an equipment decline control 490 (e.g., as shown in FIG. 4C), a proceed-to-emergency control 495 (e.g., as shown in FIG. 4A), a proceed-to-equipment control 590 (e.g., as shown in FIG. 5A), and an equipment acquisition control 936 (e.g., as shown in FIG. 9), and an arrive-at-emergency control 1110 (e.g., as shown in FIG. 11A). These controls are described in further detail with regard to the aforementioned figures. In brief, each control notifies the software application 225 of an update or change in the navigation status of the registered responder.

At stage 84, the method 200c includes updating the interactive map to provide the navigation status and an indication of the selection of the at least one item of registered equipment. For example, as discussed above, the software application 225 may update the interactive map 410 as the location of the responder changes to show the proximity of the responder to equipment and/or the emergency event. The interactive map 410 may also reflect a selection of medical equipment by the responder.

Referring again to FIG. 1 with reference to FIGS. 14-21C, method and system examples for registering responders are described below. Method and system examples for registering equipment are described below with further regard to FIG. 1 and with reference to FIGS. 22-28.

As shown in FIG. 1, the registration systems 210 and 260 may receive the responder information and medical equipment information, respectively. The responder information may include responder registration information. The medical equipment information may include medical equipment registration information. For example, the medical equipment registration information may be submitted by users that are associated with a user account in the equipment registration system 260 and/or in the management system 270. Similarly, the responder registration information may be submitted by users that are associated with a user account in the responder registration system 210 and/or in the management system 270. The registration system 260 may also receive the information regarding users and additional persons associated with the medical equipment, e.g. authorized users of the medical equipment, inspectors associated with a user account, etc. The equipment registration system 260 may store the received information in the equipment database 280. The responder registration system 210 may store the received information in the responder database 214.

In an implementation, a user 110 may access the registration system 260 and/or the registration system 210 via a remote computing device 240. The remote computing device 240 may be a computing device located remotely from the medical equipment 230 and/or an emergency scene. In contrast, the mobile computing device 220 may travel with the user 110 to a site that includes the medical equipment 230 and/or to the emergency scene. The remote computing device 240 may be personal computer, a terminal interface for a server, or a mobile computing device such as, for example, a tablet, a laptop, a wearable device, or a cellular telephone. The remote computing device 240 may be a group of communicatively coupled devices. Claimed subject matter is not limited to a particular type, category, size, etc. of computing device. The remote computing device 240 may include a processor, a memory, an input device, an output device, and a computer network interface. The computer network interface may provide a wired and/or wireless connection between the remote computing device 240 and the computer network 250. The processor, memory, input device, and output device are substantially as described below with regard to the processor 1010*a*, the memory 1020*a*, the input device 1030*a*, and the output device 1040*a*.

The user 110 may establish an equipment registration account with the equipment registration system 260. The user may provide the medical equipment registration information to the database 280 via the equipment registration account. The equipment registration account may be associated with registration login information and equipment registration information. The registration login information may include, for example, but not limited to, a user name, a password, a security code, a hardware identification code, and/or a biometric input). The registration system 260 may store the medical equipment information in the database 280. Additionally, or alternatively, the registration system 260 may update previously stored information in the database 280 based on the registration information.

Additionally or alternatively, the user 110 may establish responder registration account with the responder registration system 210. The user 110 may provide the responder registration information to the database 214 via the responder registration account. The responder registration account may be associated with registration login information and responder registration information. The registration login information may include, for example, but not limited to, a user name, a password, a security code, a hardware identification code, and/or a biometric input). The responder registration system 210 may store the responder information in the database 214. Additionally, or alternatively, the registration system 210 may update previously stored information in the database 214 based on the registration information.

The equipment database 280 is a remote database that may be a centralized repository for medical equipment information including medical equipment registration information, medical equipment management information, and/or medical equipment inspection information. The medical equipment information may be associated, in the database 280, with a particular user, inspector, physical site, etc. The medical equipment information in the database 280 may include location information for the medical equipment, as well as information regarding specific users, user accounts, inspectors, physical sites, etc. associated with the medical equipment. As a result, the medical equipment information may be sortable based on one or more of user, inspector, physical site, etc. The medical equipment information corresponds to equipment including, for example, but not limited to, public safety equipment, emergency equipment and/or hospital equipment (for example, but not limited to, external defibrillators, ventilation equipment, drug delivery equipment, physiological sensors, fire extinguishers, oxygen tanks, NARCAN® kits, first aid kits, trauma kits, tourniquet equipment, etc.).

The database 280 may service a geographic region such as a facility, a country, a state, a county, or a city. Additionally, or alternatively, the database 280 may service one or more private and/or public entities. For example, the entities may include government functions, dispatch centers, hospitals, volunteer organizations, businesses, community groups, etc.

For each item of medical equipment in the database 280, the database 280 includes medical equipment information, such as, but not limited to, one or more of an identifier of the item type (e.g., external defibrillator, ventilation equipment, drug delivery equipment, physiological sensor, fire extinguisher, oxygen tank, NARCAN® kit, first aid kit, trauma kit, tourniquet equipment, etc.), a serial number, a manufacturer, medical equipment status information, inspection information, location information, contact information, medical equipment owner information, medical equipment manager information, a medical equipment usage log, training information, and registration account information.

The medical equipment status information may include operational status information for an item of medical equipment as a whole and/or operational status information for one or more components and/or accessories. For example, the status information for an AED may include battery information and/or electrode pad information. The status information may include expiration dates, inspection dates, order information, replacement information, and/or information on upcoming dates for replacement and/or inspections of components and/or accessories. The status information may include self-test and/or diagnostic results, such as a self-testing report uploaded to the database periodically after the medical equipment performs a self-test (either automatically or upon user initiation). The operational status information may additionally or alternatively include software update and/or configuration information. As other examples, the status information for a drug delivery device may include an expiration date for the drug, the status information for a fire extinguisher may include a pressure gauge reading, and the status information for a first aid kit may include a supply inventory and/or drug expiration dates.

In an implementation, the medical equipment 230 may initiate and perform self-test and/or diagnostic functions to determine status information regarding, for example, expiration and/or functional status of components (e.g. electrodes, batteries, etc.), to confirm installation of software updates, etc. based on a predetermined and/or programmed schedule. Alternatively, or additionally, the medical equipment 230 may initiate and perform the self-test and/or diagnostic functions in response to a request from the computing device 240 and/or 220. Further, the medical equipment 230 may provide status information to the management system 270 via the computing device 240 and/or 220 and/or may receive new and/or updated software and/or configurations from the medical equipment management system via the computing device 240 and/or 220. The computing device 240 may be located remotely from the medical equipment 230 and may include the software application 225 and/or may provide information to one or more other computing devices that include the software application 225. In an implementation, the software application 225 may update or modify inspection information based on information provided by the computing device 240 and/or 220. Further, the software application 225 may provide routing, navigation, and/or location information for remotely inspected medical equipment. For example, if a remote inspection indicated that a particular item of medical equipment or components thereof was expired or malfunctioning, the software application 225 may provide location information for the particular item of medical equipment. As another example, the software application 225 may indicate that components and/or software for a particular item of medical equipment had been changed or updated and may direct an inspector to this equipment for a confirmation of the change or update.

The contact information may enable the management system 270 and/or the registration system 260 to provide reminders and/or status updates to the one or more of the medical equipment owner, inspector, manager, distributor, user, and manufacturer. The contact information may include one or more of an email address, a mailing address, a web address, a telephone number, a text message enabled mobile telephone number, etc. The management system 270 and/or the registration system 260 may provide the reminders and/or status updates via one or more of email, physical mail, voice call, text message, website update, etc.

The medical equipment information in the database 280 may include location information. The location information may include a geolocation for the medical equipment determined based on a satellite positioning system (SPS). The geolocation may include a two-dimensional location in a global coordinate system (e.g., a latitude and longitude or other earth centered coordinates). The geolocation may further include an elevation (i.e., a three-dimensional location in a global coordinate system). The elevation may be a SPS-based elevation and/or may be an elevation determined based on an indicator of elevation such as barometric pressure. In an implementation, the location information may include indoor mapping information that includes indoor locations of medical equipment. In an implementation, and as discussed in further detail below, the database 280 may designate equipment as portable and the location stored in the database 280 may be editable and/or be able to be updated.

In an implementation, the registration system 260 may receive a user-input medical equipment location provided via the website for the registration system 260. For example, the user may fill in a text field to provide the location information. The user-input medical equipment location may include a physical address of the medical equipment and/or a description of the physical location of the medical equipment. The physical address may include a street address. The registration system 260 may store the user-input medical equipment location in the database 280. In an implementation, the registration system 260 may convert the user-input medical equipment location to a geolocation. In an implementation the management system 270 may convert the user-input location for the medical equipment to an indoor location referenced to mapping information for the facility 205 in which the medical equipment is located.

In an implementation, the registration system 260 may receive the location of the medical equipment via a mapping utility. For example, the registration system 260 may provide a map of an area that includes medical equipment via a mapping utility accessed by the registration system 260. In an implementation, the mapping utility is a user interactive mapping utility. For example, the user may drag and drop a pin or other icon corresponding to the location of medical equipment 230 on a displayed map. The location of the pin may provide more accurate location information than the text field information described above. For example, the text field information may include a street address for a facility, like a hospital, that occupies and corresponds to a visible area on the map. The user may drag and drop the pin within the visible area to locate the medical equipment within the facility, for example, in a lobby of the hospital, in a parking lot, and/or in a treatment room. The mapping utility may convert the pin location to a geolocation and provide the geolocation to the registration system 260 for storage in the database 280. In an implementation, the medical equipment 230 may self-report a location to the registration system 260 based on the location information determined by the location module 1050*b* associated with the medical equipment 230.

The responder database 214 is a remote database that may be a centralized repository for responder information discussed with regard to FIGS. 15-21B. This information includes, for example, identification and contact information for responders. The contact information may be contact information for the responder and a computing device associated with the responder (e.g., a cellular telephone number, an email address, an IP address, etc.). The database 214 may include responder preferences with regard to types of emergencies, hours of availability, preferred locations, preferred equipment, etc.). The database 214 may further include user certifications, verifications of certifications, qualifications for various medical situations, and information about equipment owned and/or in the responder's possession. The database 214 may also include responder histories such as the information in the notification summary screen 2120 shown in FIG. 21C.

The database 214 may service a geographic region such as a facility, a country, a state, a county, or a city. Additionally, or alternatively, the database 214 may service one or more private and/or public entities. For example, the entities may include government functions, dispatch centers, hospitals, volunteer organizations, businesses, community groups, etc.

The registration systems 210 and 260, the management system 270 and the databases 214 and 280 may be implemented as stored data and/or stored processor executable instructions in one or more non-transient memories of one or more servers 212, 216, 262, 272, and 282. One or more processors associated with the one or more servers 212, 216, 262, 272, and 282 may execute these stored instructions and access the stored data to provide the functions of the registration systems 210 and 260, the management system 270, and the databases 214 and 280, as described above. The servers 212, 216, 262, 272, and 282 may be, for example, but not limited to, a network server, an enterprise server, a server associated with a particular website and/or application, a cloud network server, or a combination thereof. Although servers 212, 216, 262, 272, and 282 are shown in FIG. 1 as single servers for simplicity, other quantities of servers (e.g., one or more servers or a plurality of servers) could be used. The servers 212, 216, 262, 272, and 282 are computing devices including at least one processor and a memory and are configured to execute computer executable instructions. For example, the servers 212, 216, 262, 272, and 282 may be a computer system including a processor, non-transitory memory, a display, and a data input mechanism for a user.

The processor is preferably an intelligent device, e.g., a personal computer central processing unit (CPU), a microcontroller, an application specific integrated circuit (ASIC), etc. The memory may include random access memory (RAM) and read-only memory (ROM). The memory includes a non-transitory processor-readable storage medium (or media) that stores processor-readable, processor-executable software code containing one or more instructions or code for controlling the processor to perform functions described herein. The software can be loaded onto the memory by being downloaded via a network connection, uploaded from a disk, etc. In an example, the servers 212, 216, 262, 272, and 282 are comprised of multiple server units. The multiple server units may be administered by one or more enterprises.

In an implementation, the user 110 may establish an account with the management system 270. The software application 225 may enable access to the account. The account may be an equipment management account and/or a responder account. The responder account may be a separate account from the equipment management account for a collection of medical equipment but may be linked to the equipment management account. Alternatively, the responder account and the equipment management account may be the same account (e.g., a combined account).

The equipment management account may provide management access privileges. For example, the management access privileges may allow a medical equipment owner, a medical equipment coordinator for a site, a medical equipment distributor and/or manufacturer, and/or other medical equipment managers to add medical equipment or other information to the database 280 and/or otherwise edit the database 280, manage software and configuration updates, receive reports and/or other notifications for medical equipment owned and/or coordinated by an entity, and/or view, edit, or add inspection information, consumable information, repair and/or replacement information. Each management system account may correspond to one or more items of medical equipment registered in the database 280. Therefore, based on the login information and corresponding account information, the user of the software application 225 may have access to the medical equipment information stored in the database 280 for medical equipment associated with the one or more management system accounts and/or the one or more inspection accounts. The software application 225 may display, or otherwise make available to the user, the medical equipment information associated with the one or more management system accounts and/or the one or more inspection accounts.

The responder account may provide access to responder preference settings, responder histories, responder identification information, and/or responder certification information. For example, the registered responder may log in to their account to view and/or change the accessible information. The accessible information may be all or a portion of the responder information and settings discussed with regard to FIGS. 15-21B.

The user 110 of the software application 225 may obtain login information for the software application 225. The login information may include, for example, but not limited to, a user name, a password, a security code, a hardware identification code, and/or a biometric input. For example, the login information for the software application 225 may correspond to account information for one or more management system accounts and/or to account information for one or more responder accounts. The login information and/or the associated account information may identify the user as a responder, as a manager, or as both.

The software application 225 may provide a responder user interface. The responder user interface may include one or more display screens configured to enable the responder to find the location of the emergency event, find the location of medical equipment, and bring the medical equipment to the emergency event.

In an implementation, the software application 225 may be configured to receive information transmitted by the medical equipment 230. For example, the software application 225 may receive signals transmitted by the medical equipment over a wired and/or wireless connection between the medical equipment 230 and the mobile computing device 220. For a wired connection, the mobile computing device 220 may receive this information via a wired input/output port 1085a (e.g., a universal serial bus (USB) port). The medical equipment may include a complimentary wired input/output port 1085b. For a wireless connection, the mobile computing device 220 may receive this transmitted information via the transceiver 1070a. The transmitted information may include location information, identification information, a media access control (MAC) address, internet protocol (IP) address and/or other network address.

Alternatively, or additionally, the software application 225 may receive medical equipment information via the camera 1080, the asset tag reader 1090, and/or anther input device 1030a of the mobile computing device 220. For example, the medical equipment may include an asset tag (e.g., the barcode 235 and/or the radio frequency identification (RFID) tag 236) compatible with the asset tag reader 1090.

Various entities in FIG. 1 are communicatively coupled via one or more networks 250. The one or more networks 250 may include a computer network and/or a communications network. The computer network may include a mobile switching center and a packet data network (e.g., an Internet Protocol (IP) network referred to herein as the Internet). The computer network may be a portion of the communications network. The communications network may include, but is not limited to, a wireless wide area network (WWAN), a wireless local area network (WLAN), a wireless personal area network (WPAN), and so on. The WPAN may include a Bluetooth® network, for example. Wireless communication networks may include so-called next generation technologies (e.g., "4G", "5G"), such as, for example, Long Term Evolution (LTE), Advanced LTE, WiMax, Ultra Mobile Broadband (UMB), and/or the like.

Figure 14:
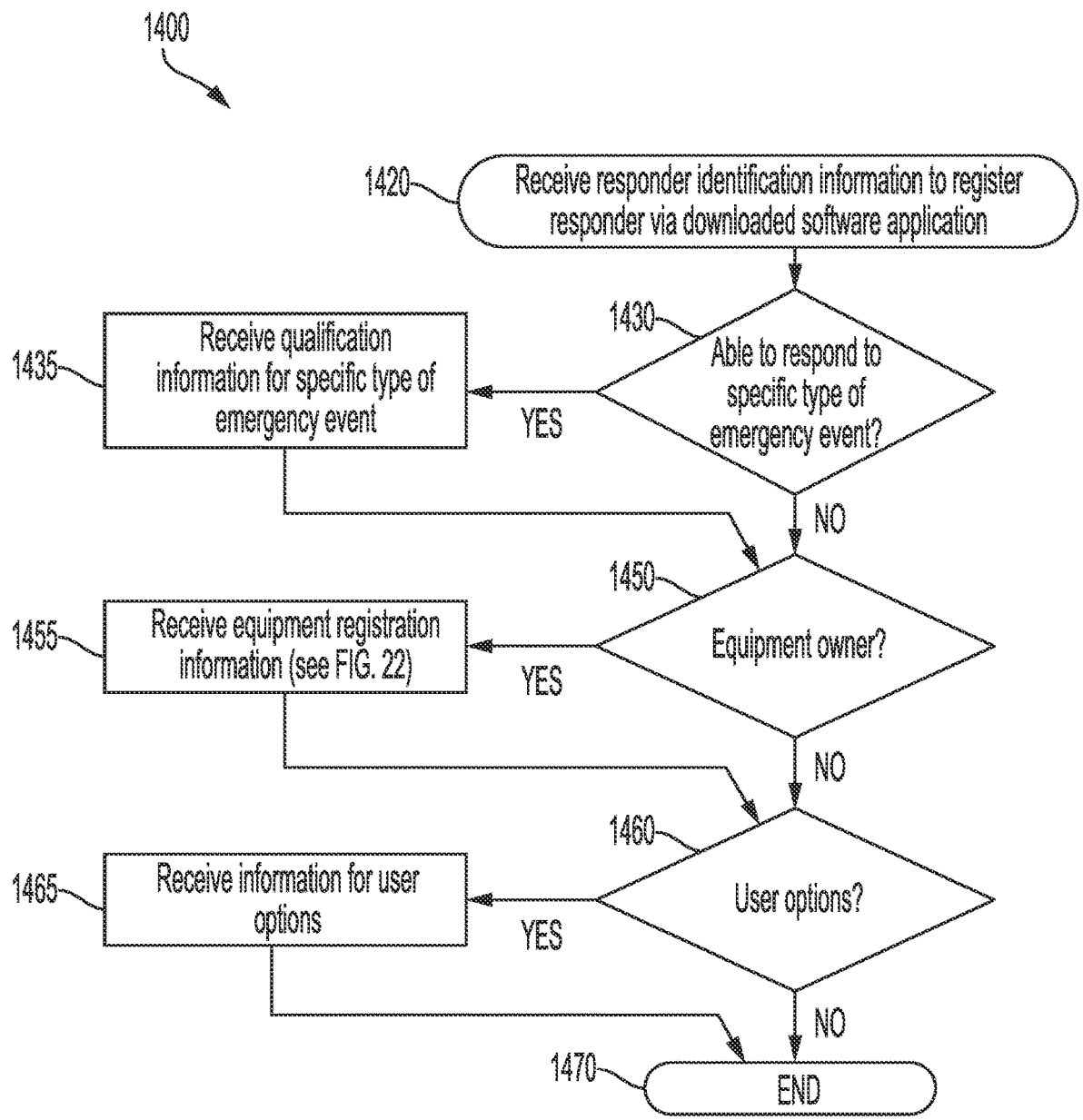
FIG. 14 shows a block diagram of a computer-implemented method for registering responders.
Figure 15:
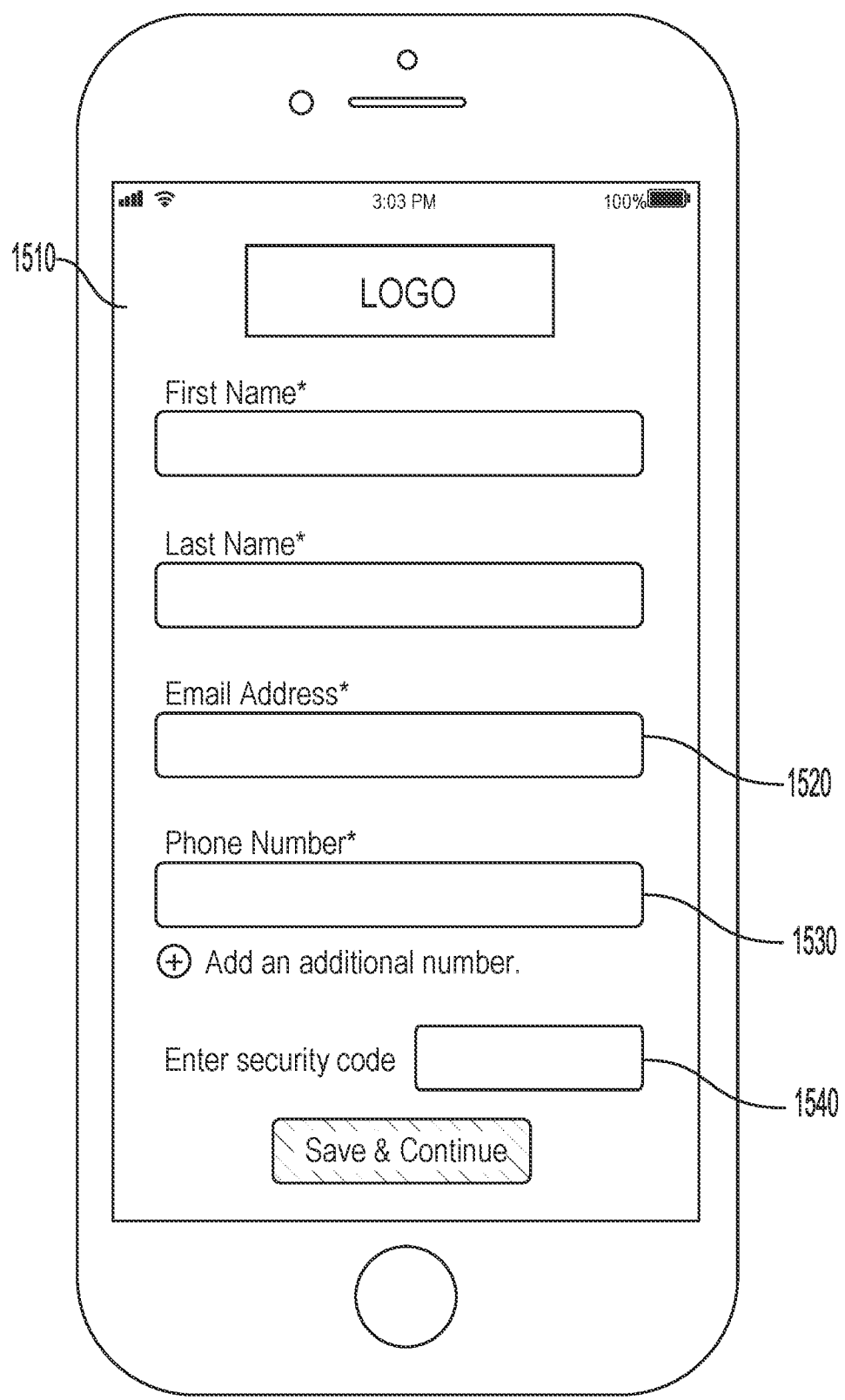
FIG. 15 shows an example of a responder registration window.
Figure 16A:
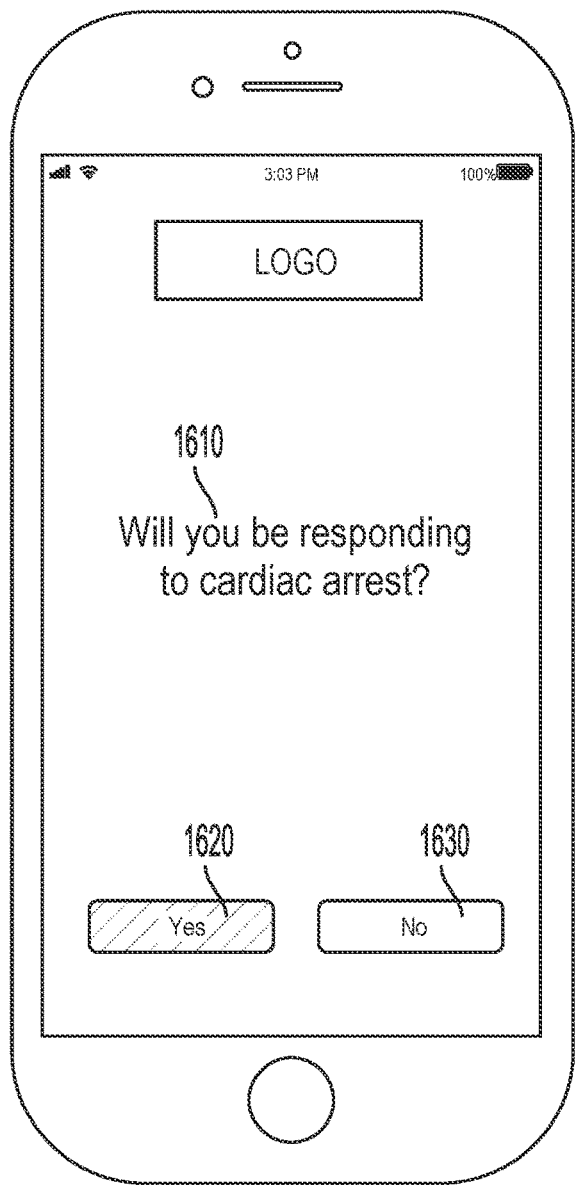
FIGS. 16A and 16B show examples of special skills queries of the software application.
Figure 16B:
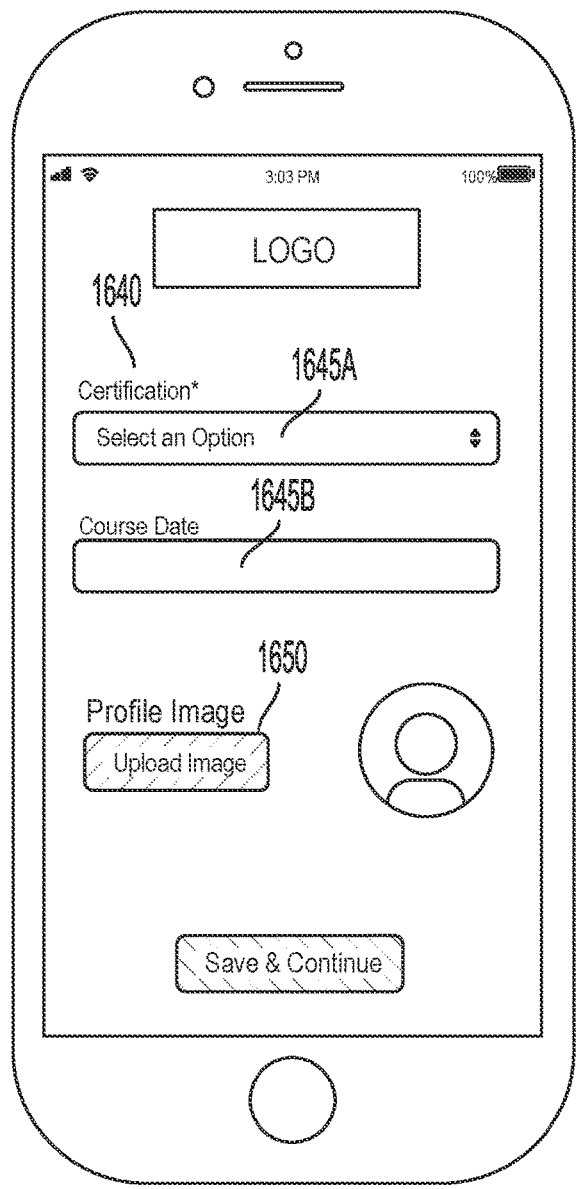

Referring to FIG. 14, a block diagram of a computer-implemented method for registering responders is shown. The method 1400 is, however, an example only and not limiting. The method 1400 can be altered, e.g., by having stages added, removed, rearranged, combined, and/or performed concurrently. The method 1400 is described with further reference to FIG. 1 and FIGS. 15-21C.

At stage 1420, the method 1400 includes receiving responder identification information to register a responder via a downloaded software application. For example, referring to FIG. 1, the user 110 may download the software application 225 to the computing device 220 and/or another computing device 240. The software application 225 may prompt the user 110 to enter registration information and may receive the entered information. For example, referring to FIG. 15, the software application 225 may provide a responder registration window 1510 that prompts the user 110 to enter information including, but not limited to, a name, an email address, and identification information for the computing device 220 associated with the user 110. The identification information for the computing device 220 may include a mobile phone number. The software application 225 may provide the registration information to the management system 270 and/or the responder registration system 210 via the network 250. The management system 270 and/or the responder registration system 210 may save the registration information in the responder database 214. In an implementation, the responder registration window 1510 may implement an authentication procedure. The software application 225 may send a security code to the email address 1520 and/or text the security code to the phone number 1530. The software application 225 may require entry of the security code in a security window 1540 to proceed with registration of the responder. This authentication procedure may prevent registration by a software application running automated tasks (e.g., prevent registration by Internet bots or web bots) and ensure that a human responder is interacting with the registration window 1510.

At stage 1430, the method 1400 may include prompting the user 110 to indicate whether he/she is able to respond to a specific type of emergency event. For example, referring to FIG. 16A, the software application 225 may provide a special skills query 1610 along with a "yes" response button 1620 and a "no" response button 1630. In this example, the special skills query 1610 asks the user 110 to indicate if they can respond to a cardiac arrest. In other examples, the special skills query 1610 may ask the user 110 if they can respond to a drug overdose, a trauma, a hemorrhage, a chemical exposure, etc. In an implementation, the skills query 1610 may include one or more specific types of events.

If the user 110 provides a "yes" response at the stage 1430, the method 1400 proceeds to stage 1435. The stage 1435 includes receiving qualification information for the specific type of emergency event. As shown, for example in FIG. 16B, for each type of event that the user 110 provides a "yes" response via the "yes" button 1620, the software application 225 may provide a certification window 1640 at the stage 1435. The certification window 1640 may provide one or more entry fields 1645A and 1645B configured to capture input from the user 110 regarding certification credentials as a responder to a particular type of emergency event and/or further personal identification information such as a photograph. The certification window 1640 and/or another window provided by the software application 225 may provide an image upload control 1650 configured to enable the user 110 to upload a personal image. The software application 225 may provide the special skills, certification, and/or personal image information to the management system 270 and/or the responder registration system 210 via the network 250. The management system 270 and/or the responder registration system 210 may receive the information and save the information in the responder database 214. In an implementation, the responder registration system 210 may provide a responder's name, certification information, and/or other responder information to the emergency dispatch service 125 (e.g., the CAD). The emergency dispatch service 125 may provide an authorization for registration of the responder based on one or more dispatch records or other criteria. Alternatively, the emergency dispatch service 125 may disapprove the potential responder based on one or more dispatch records or other criteria. The responder registration system 210 may deny registration for the disapproved responder or may limit the disapproved responder to particular types or locations of emergency events based on disapproval details.

Following the stage 1435 or if the user provides a "no" response at the stage 1430, the method proceeds to stage 1450. At the stage 1450, the method 1400 may include prompting the user 110 to indicate whether he/she owns one or more items of medical equipment. For example, referring to FIG. 17A, the software application 225 may provide an equipment ownership query 1710 along with a "yes" response button 1720 and a "no" response button 1730. In an implementation, the equipment ownership query 1710 may include one or more types medical equipment such as, for example, public safety equipment, emergency equipment and/or hospital equipment (for example, but not limited to external defibrillators, ventilation equipment, drug delivery equipment, physiological sensors, fire extinguishers, oxygen tanks, drug overdose kits (e.g., NARCAN® kits), first aid kits, trauma kits, tourniquet equipment, eye wash equipment, etc.). In an implementation, the equipment ownership query 1710 may include multiple queries and associated response buttons on one screen or window for multiple types of medical equipment. Alternatively, the equipment ownership query 1710 may correspond to multiple screens and/or windows and the software application 225 may successively display the query for the various types of medical equipment. In an implementation, the equipment ownership query 1710 may include multiple selectable equipment item windows 1740, as shown for example in FIG. 17B. As an example, the user 110 may click on or tap or provide another touchscreen gesture to one or more of the windows 1740 to select the equipment. For each selected window, the software application 225 may provide an equipment registration window. The user may also select the "no equipment" window 1750 to exit from the equipment ownership query.

If the user 110 provides a "yes" response at the stage 1450 and/or selects one or more windows 1740, the method 1400 proceeds to stage 1455. The stage 1455 includes receiving equipment registration information. The stage 1455 is described in further detail below with regard to FIGS. 22-28.

Following the stage 1455 or if the user provides a "no" response at the stage 1450, the method proceeds to stage 1460. At the stage 1460, the method 1400 may include providing the user 110 with a menu of one or more user options in a user options window described below with regard to FIG. 18. If the user selects an option from the menu, the method 1400 proceeds to the stage 1465 and receives the selection of the user option and/or information associated with the selected user option. Following the selection of the user option and/or if the user declines to select any options, the method 1400 proceeds to the stage 1470.

Figure 18:
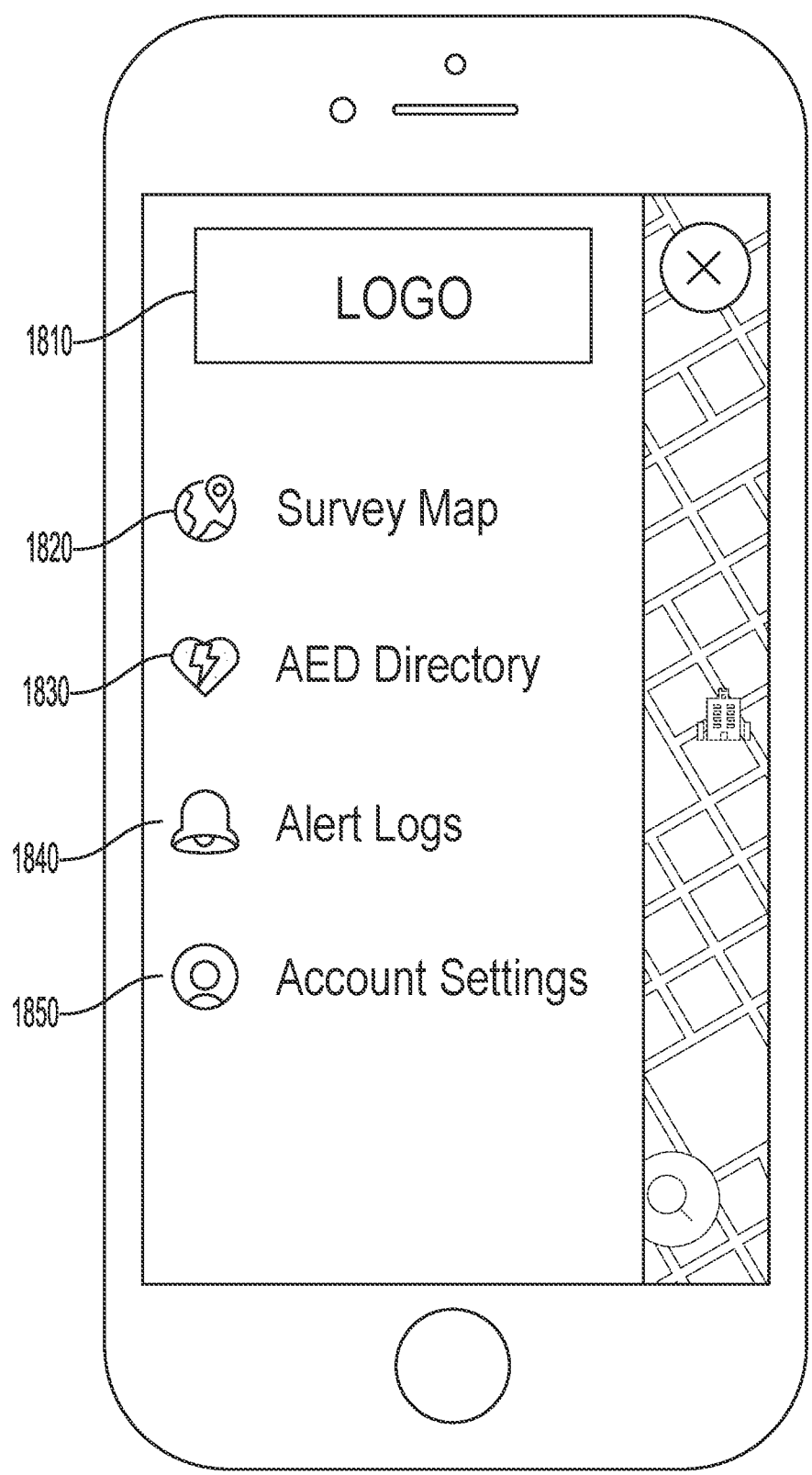
FIG. 18 shows an example of a user options window of the software application.

At stage 1470, the registration process is complete and the user 110 is a registered responder. In an implementation, the registered responder may log in to the application 225 subsequent to registration and access one or more of the stages of the method 1400 in order to change, delete, or otherwise edit the registration information and/or the user options Referring to FIG. 18, the software application 225 may provide the user options window 1810. The user options window 1810 may include one or more selectable user options. For example, the user options may include a survey mapping option 1820, an equipment directory option 1830, an alert log option 1840, and an account settings option 1850. The user options shown in FIG. 18 are examples only and other user options are consistent with the disclosure. The user 110 may click on or tap or provide another touchscreen gesture at one of the user options to select the option. In response to the selection, the software application 225 may provide one or more windows with information and/or user selection controls related to the selected option. Examples of these windows are described below with regard to FIGS. 19-21C.

Figure 19:
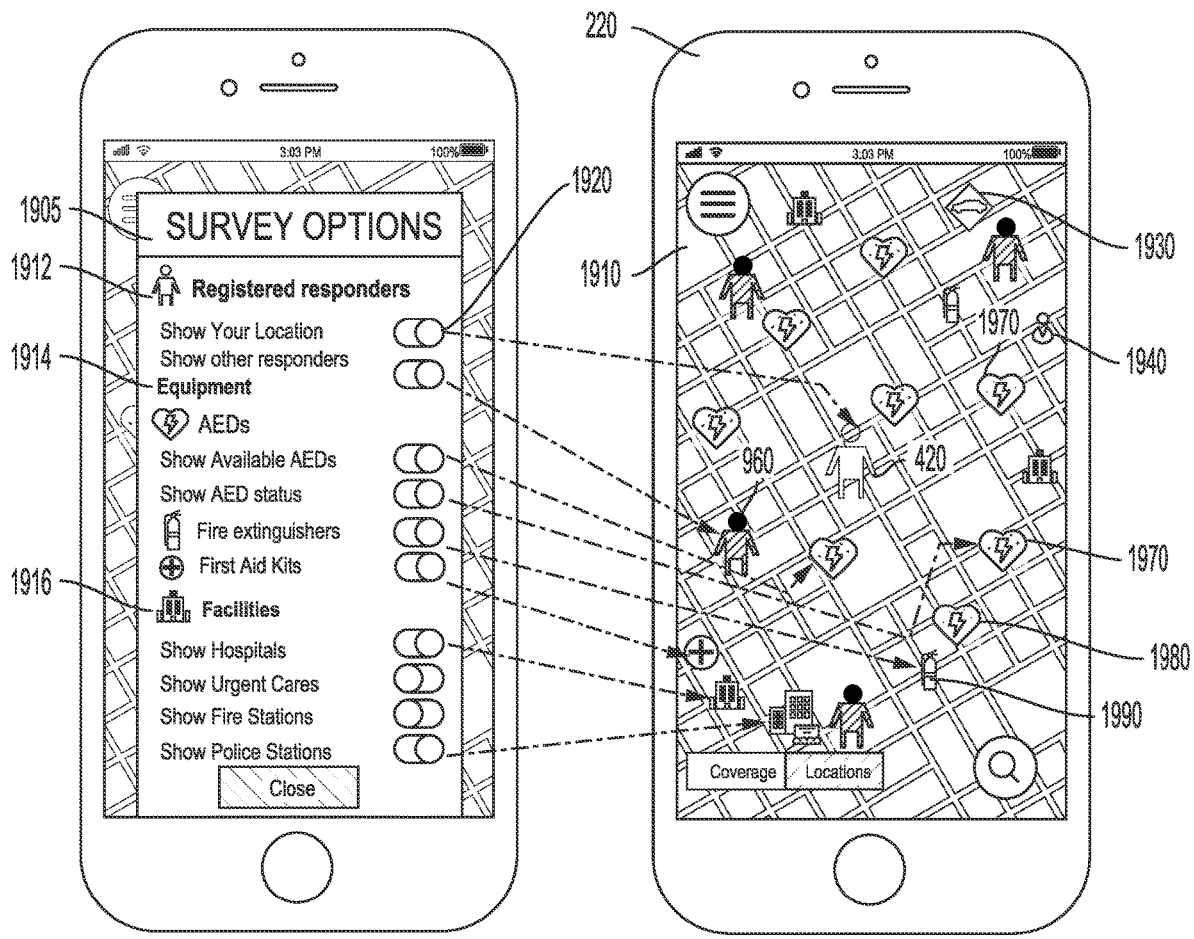
FIG. 19 shows examples of user selectable mapping options and a survey map.

Referring to FIG. 19, in response to a selection of the survey mapping option 1820, the software application 225 may provide one or more of the user selectable mapping options 1905. The user selectable mapping options 1905 may apply to the interactive map 410 and/or to a survey map 1910. In an implementation, the registered responder 110 may access the survey map 1910 during and/or outside of the assistance request session in a survey mode of the software application 225. As such, the survey map 1910 may not include the emergency event location indicator 423 as this map may be viewed in the absence of an emergency event. However, the interactive map 410 and the emergency assistance user interfaces provided via the interactive map 410 (e.g., the interfaces described with regard to FIGS. 3-13B) may only be available during the assistance request session. In some examples, the interactive map 410 always includes the emergency event location indicator 423 since this map is accessed during the assistance request session. In an implementation, the survey map 1910 may be configured to capture user input, for example, via touch screen gestures.

The user selectable mapping options 1905 may include responder options 1912, medical equipment options 1914, and/or facility options 1916. Each option may correspond to a slider button 1920 and/or a set of yes/no buttons and/or some other selectable user button configured to capture a preference of the user 110. The software application 225 may include selected items on the survey map 1910 and/or the interactive map 410. Similarly, the software application 225 may exclude unselected items from the survey map 1910 and/or the interactive map 410. For example, in FIG. 19, the facility options 1916 of "urgent cares" and "fire stations" are shown as unselected and are not represented on the survey map 1910. Conversely, the facility options 1916 of "hospitals" and "police stations" are shown as selected and are represented on the survey map 1910. The example of FIG. 19 includes hospitals, urgent cares, fire stations, and police stations as illustrative examples of facilities. However, these illustrative examples are not limiting of the disclosure and the software application 225 may include one or more other types of facilities in addition to or as an alternative to those shown in FIG. 19.

As illustrated in FIG. 19, for each selected item in the options 1905, the survey map 1910 may include a representative location indicator for the selected item. The representative location indicators may have different appearance aspects, such as shape, size, and/or color, in order to distinguish the items represented by the location indicators from one another. For example, the location indicators 1970 and 1980 may represent AED locations and the location indicator 1990 may represent a fire extinguisher location. The example of FIG. 19 includes AEDs and fire extinguishers as illustrative examples of equipment. However, these illustrative examples are not limiting of the disclosure and the software application 225 may include one or more other types of equipment in addition to or as an alternative to AEDs and/or fire extinguishers.

In an implementation, the software application 225 may select and/or modify an appearance aspect of the equipment location indicators 1970, 1980, and 1990 such as shape, size, and/or color in order to differentiate amongst various equipment statuses. The equipment database 280 may store the equipment status information and may obtain this information via the registration system 260 and/or the management system 270. Similarly, the software application 225 may modify an appearance aspect such as shape, size, and/or color of the equipment location indicators for the interactive map 410 (e.g., the indicators 425a, 425b, 425c, and/or 915 shown for example in FIGS. 4A, 7, and 9) in order to differentiate amongst various equipment statuses. In an implementation, the equipment location indicators may be graphic icons and the activity log 780 may include the same graphic icons with the modified appearance aspect based on status.

As an example, the equipment status may be a time availability of the equipment. The time availability refers to times of day that the equipment is available based on, for example, times at which a building or other structure that houses the medical equipment provides access to the equipment. As discussed below with regard to FIG. 24, an equipment registration process may prompt the user for time availability information. In an implementation, unavailable equipment may be gray and available equipment may be another color or a different shade of gray. Alternatively or additionally, unavailable equipment may have a smaller icon than available equipment.

As another example, the equipment status may be an operational status of the equipment. The operational status of the equipment may include or refer to an operational status of equipment components. For example, as discussed below with regard to FIG. 26 and in FIG. 27, the equipment registration process may prompt the user for one or more of inspection information 2610 (e.g., an inspection frequency or interval such as daily, weekly, monthly, biannually, annually, etc.), an installation date 2640, and consumables information 2740. The consumables information 2740 may refer to information about equipment components and may include one or more of expiration date and installation date information. Based on the operational status of the equipment and/or the equipment components/consumables, the management system 270 may determine various statuses of the equipment. Each status may correspond to an appearance feature of the location indicators 1970 and 1980.

In an implementation, the equipment status may be a combination of time availability and operational status. For example, the icon for an operational item of equipment that is unavailable based on time may have a different appearance from the icon for the operational item of equipment that is available based on time. In an implementation, the icon may include multiple features that indicate status. For example, an operational item of equipment may exhibit a color indicative of being operational but include a line through it or a letter code or "u" or "unavailable" indicating that the item of equipment is not available at a particular time.

Table 1 below provides examples of appearance features based on status. These appearance features are examples only and not limiting of the disclosure. As discussed above, the statuses referred to in Table 1 may determine whether the equipment is available based on time availability and/or based on operational status.

TABLE 1

| STATUS | APPEARANCE FEATURE |
| --- | --- |
| AVAILABLE BASED ON TIME | ICON INCLUDED ON MAP WITH A COLOR OTHER THAN GRAY |
| UNAVAILABLE BASED ON TIME | ICON EXCLUDED FROM MAP OR ICON INCLUDED ON MAP WITH A GRAY COLOR |
| VERIFIED AS OPERATIONAL | ICON INCLUDED ON MAP WITH A GREEN COLOR |
| UNVERIFIED AS OPERATIONAL | ICON INCLUDED ON MAP WITH A YELLOW COLOR |
| VERIFIED AS NON-OPERATIONAL | ICON EXCLUDED FROM MAP OR ICON INCLUDED ON MAP WITH A RED COLOR |

In the example of Table 1, "verified as operational" may indicate a verified operable condition of the equipment. For example, the database 280 may include a verification that inspection of the medical equipment 230 has occurred according to the inspection schedule provided at registration (e.g., the inspection information 2610) and/or within a pre-determined amount of time such as within the last month, the last three months, the last six months, the last year, the last two years, the last five years, etc. Additionally, "verified as operational" may indicate that none of the equipment and the components/consumables are past the registered expiration date and/or within an expiration period determined by the management system 270 based on an installation date. "Unverified as operational" may indicate an unverified operable condition of the equipment. For example, the database 280 may include information that inspection of the medical equipment 230 has not occurred since a previously documented inspection and/or installation according to the inspection schedule and/or within the pre-determined amount of time. Alternatively, "unverified as operational" may indicate that the medical equipment database 280 does not include any inspection verification information since the previously documented inspection and/or installation. Additionally, "unverified as operational" may indicate that none of the equipment and the components/consumables are past the registered expiration date and/or within an expiration period determined by the management system 270 based on an installation date. Therefore, "unverified as operational" may indicate that the medical equipment is expected to be operational but that the operational status is not confirmed by the management system 270. A further status of "verified as non-operational" may indicate a verified inoperable condition of the medical equipment. For example, the medical equipment database 280 may include information that inspection of the medical equipment 230 has occurred since a previously documented inspection and/or installation and that the inspection found the equipment to be non-operational. Additionally or alternatively, the status of "verified as non-operational may indicate that the medical equipment database 280 includes information that the equipment and/or the components/consumables are past the registered expiration date and/or within an expiration period determined by the management system 270 based on an installation date.

As shown in FIG. 19, in an implementation, the user may select to show location indicators for unavailable and/or non-operational equipment on the survey map 1910 and/or the interactive map 410. Conversely, the user may select to hide location indicators for unavailable and/or non-operational equipment. Additionally or alternatively, the user may select to show the equipment status. For example, map 410 and/or 1910 may hide icons for unavailable equipment and non-operational equipment and may show icons for available equipment and operational equipment with different colors of the icon corresponding to operational statuses of "verified" and "unverified" as described with regard to Table 1. In an implementation, the management system 270 may determine the map properties with regard to which location indicators to include and/or may provide a default setting that is adjustable by the user.

In an implementation, the software application 225 may further include location indicators 1930 for dispatched vehicles such as EMS, police, and/or fire vehicles on the survey map 1910 and/or the interactive map 410 and/or may include location indicators 1940 for dispatched responders. The dispatched responders may be those responders managed by the EMS agency 130 shown in FIG. 1 in contrast to the registered responders managed by the management system 270 as shown in FIG. 1. In an implementation, the emergency event information 150 may include location information for locations of EMS responders and/or vehicles. The software application 225 may include icons for the EMS responders and/or vehicles on the survey map 1910 and/or the interactive map 410 based on this information. In an implementation, during the assistance request session, the software application 225 may include icons for dispatched EMS responders and/or vehicles on the interactive map 410.

The responder options may determine which responders are represented on the survey map 1910 and/or the interactive map 410. For example, the software application 225 may provide one or more responder location indicators 960, 420, and 1940 that correspond to different responders. The responder location indicator 420 may correspond to the location of the registered responder associated with the computing device 220. The responder location indicator 960 may correspond to the location of another registered responder not associated with the computing device 220. In this example, the location indicator 420 is a first color and the location indicator 960 is a second color. Referring again to FIG. 8, the interactive map 410 and/or the survey map 1910 displayed on the mobile device 820A may include the location indicator 420 with the first color at the location of responder 1 and may include the location indicators 960 with the second color at the locations of responders 2 and 3. Similarly, the interactive map 410 and/or the survey map 1910 displayed on the mobile device 820B may include the location indicator 420 with the first color at the location of responder 2 and may include the location indicators 960 with the second color at the locations of responders 1 and 3. Further, the interactive map 410 and/or the survey map 1910 displayed on the mobile device 820C may include the location indicator 420 with the first color at the location of responder 3 and may include the location indicators 960 with the second color at the locations of responders 1 and 2.

In an implementation, each registered responder may select whether to include other responders and/or dispatched responders on the interactive map 410 and/or the survey map 1910. In an implementation, the management system 270 may determine whether to include other responders and/or dispatched responders on the interactive map 410 and/or the survey map 1910. The management system 270 may determine a default setting for responder representations on the interactive map 410 and/or the survey map 1910. The default setting may be adjustable by the user.

Figure 20:
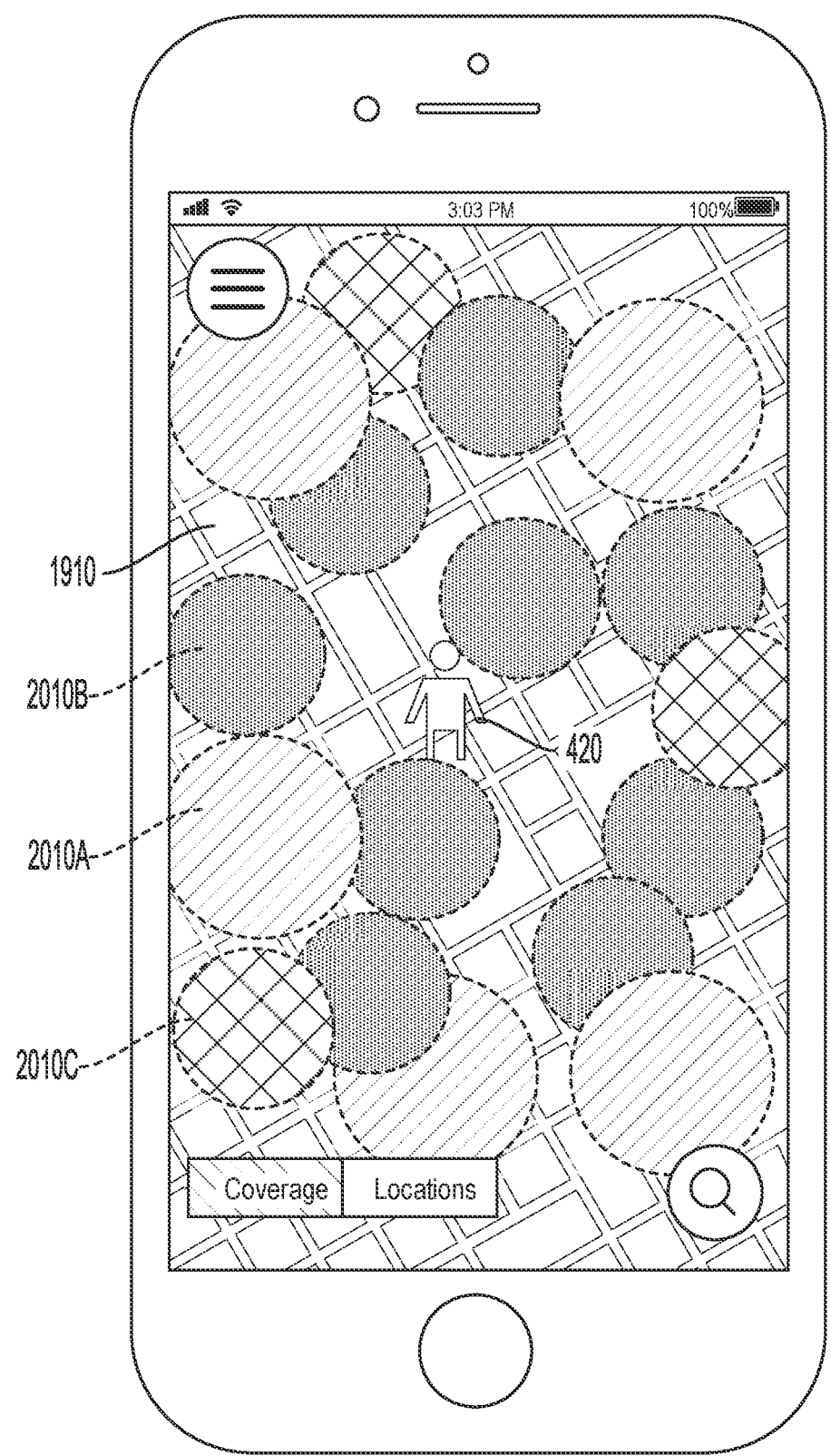
FIG. 20 shows an example of a survey map with location bubble icons.

In an implementation, referring to FIG. 20, the management system 270 may provide the survey map 1910 with location bubble icons 2010A, 2010B, and/or 2010C. The location bubble icons 2010A, 2010B, and 2010C may indicate location estimates for other responders, medical equipment, and facilities, respectively. The location bubble icons may provide a location estimate based on a pre-determined radius from a location stored in the database 280 and/or 214. Using an estimate in place of a more precise location may help prevent theft of medical equipment, protect responder privacy and/or safety, and/or protect various facilities. The management system 270 may selectively toggle between location bubbles and more precise location representations.

Figures 21A, 21B:
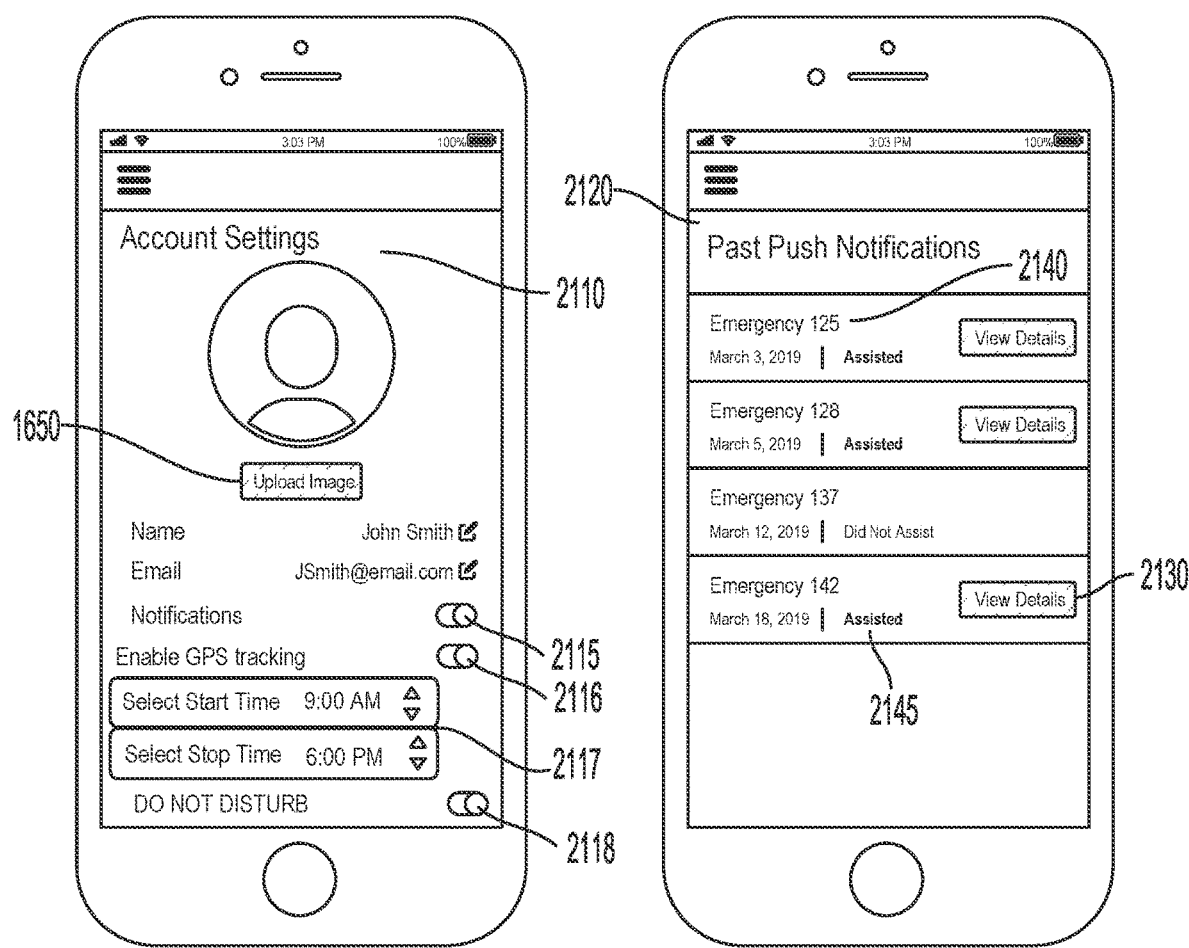
FIGS. 21A, 21B, and 21C show examples of responder registration account option user interfaces.
Figure 21C:
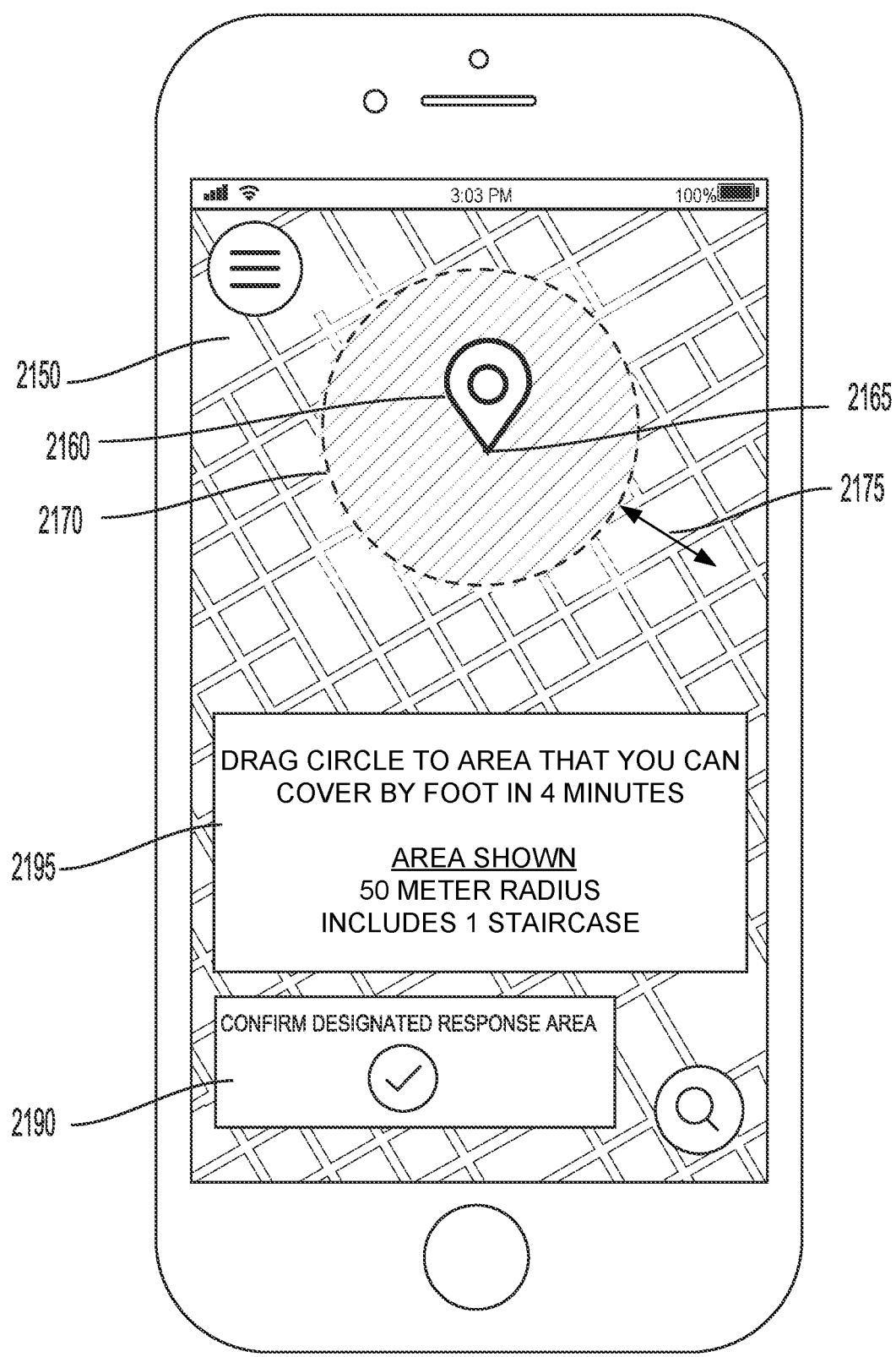
Figure 22:
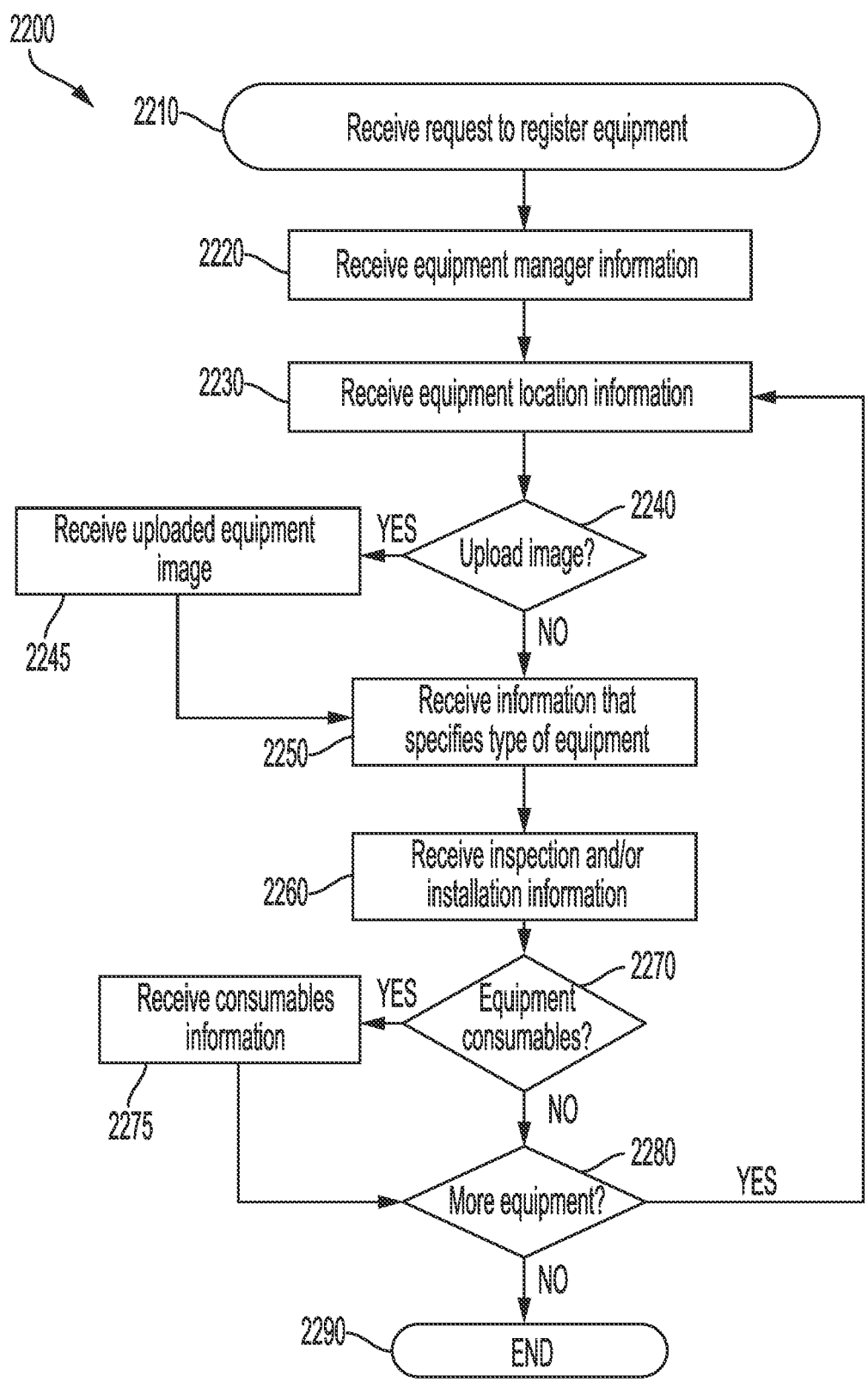
FIG. 22 shows a block diagram of a computer-implemented method for registering equipment.
Figure 23A:
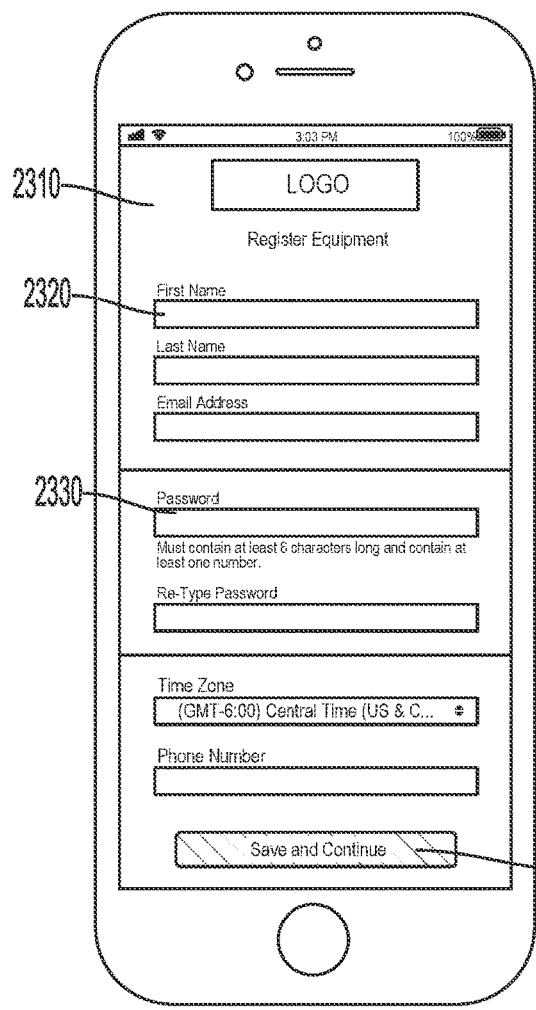
FIGS. 23A and 23B show examples of equipment registration windows of the software application.
Figure 23B:
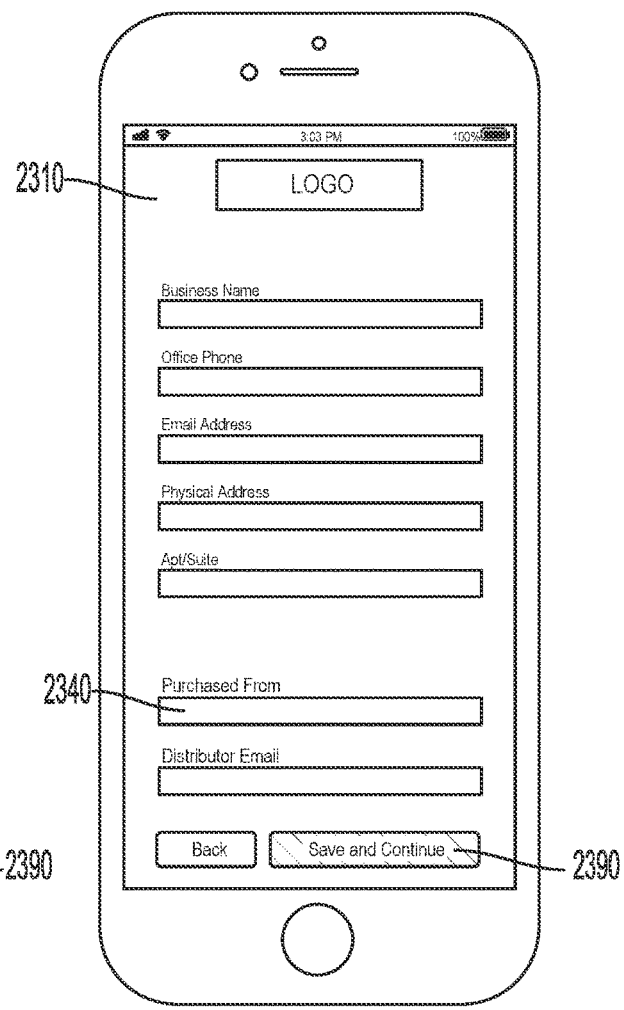

Referring to FIGS. 21A, 21B, and 21C, examples of responder registration account option user interfaces are shown. In an implementation, the account settings available at registration are also available to the user as long as the software application 225 is installed on the computing device 220 and the user may log in to their account and adjust settings as needed. FIG. 21A shows a schematic diagram of an account settings interface 2110 that may include the image upload control 1650. The image upload control 1650 may enable the registered responder to upload a photograph. The account settings interface 2110 may also include user selectable permission settings such as, for example, a notifications control 2115 and/or a GPS tracking control 2116. The notifications control 2115 may enable the user to view a notifications summary screen 2120 as shown for example in FIG. 21B. The notifications summary screen 2120 may include a list of events for which the management system 270 provided the emergency assistance request to the computing device associated with the registered responder. For each request, the summary screen 2120 may include an emergency event identifier 2140, an indication 2145 of whether or not the registered responder participated in the event and/or a view details control 2130. The view details control 2130 may enable the registered responder to view all or a portion of emergency event information acquired by the management system 270 via the software application 225 and/or via the emergency dispatch service 125. The GPS tracking control 2116 may enable or disable GPS tracking of the computing device 220 associated with the responder 110. The start/stop control 2117 may enable the user to designate an availability window. The "do not disturb" control 2118 may enable the user to opt out of receiving emergency notifications. For example, the user may opt out during a vacation, a work event, a personal event, etc. To allow or disallow, automatic tracking, the user may enable or disable a user selected tracking permission setting. The responder database may store this setting and the management system 270 may retrieve this setting from the responder database.

FIG. 21C shows a schematic diagram of an account settings interface 2150 that may enable selection of designated response area for the responder. In an implementation, during the registration process, the application 225 may enable a user registering as a potential responder to designate a particular geographic area as a designated response area 2170 for the user. The designated response area for the user is an area within which the potential responder can reach an item of medical equipment and/or a victim within a pre-determined amount of time. In an implementation, the designated response area may be approximately centered on a starting location of the responder at a time of the request for assistance with the emergency event. The user may drop a pin 2160 at a starting location 2165 or the software application 225 may drop the pin 2160 at a current GPS location of the responder. The starting location 2165 may be a home, office, or expected location. In an implementation, the responder may designate multiple starting locations and/or designated response areas. In a further implementation, the responder may change the starting location 2165 and/or the designated response area 2170 due to travel of the responder to a new location. The designated response area may depend on a mode of transport of the responder. For example, the designated response area may be an area with an approximate radius of 50-1000 meters. Such a pre-determined distance may be determined based on a distance that a person on foot at an average walking speed of 3-7 kph could reasonably be expected to traverse within a time period of 2-4 minutes or in less than 5 minutes, or less than 10 minutes.

In an implementation, the application 225 may suggest the designated response area 2170 based on the type of emergency event. For a cardiac arrest, arrival of a responder at the victim within a time frame of 2-4 minutes may be crucial as survival rates for cardiac arrest may drop by 10% for every minute of time without CPR following the cardiac arrest. However, an emergency response for an emergency event other than cardiac arrest may be viable after a longer period of time than for a cardiac arrest. Therefore, the designated response area 2170 may be bigger than that for a cardiac arrest.

The designated response area 2170 may depend on a mode of transport of the responder. For instance, the responder may walk or drive to the emergency event. An estimated travel time for driving may be shorter than that for walking. In this case, the designated response area 2170 for a driving responder may be larger than that for a walking responder. In an implementation, the software application 225 may include a user-determined setting indicating the mode of transport of the registered responder and/or a user preference for a designated response area radius. As an example, a registered responder in an urban setting may select walking and a registered responder in a rural setting may select driving.

In an implementation, the application 225 may suggest a radius or other distance associated with the designated response area. For example, the application 225 may provide a map with the suggested area indicated on the map and centered at the base location for the responder. The suggested area may vary based on a population density, for example, based on an area being urban, suburban, rural, etc. The application 225 may further provide a description 2195 of the task to be performed by the responder within the suggested area, an approximate size of the area, and obstacles within the area such as staircases, street crossings, etc. As part of registration, the user may confirm 2190 the designated response area or modify the suggested radius as indicated by the arrow 2175. In an implementation, the application 225 may use an interior map to determine the designated response area. For example, if the responder lives in a high-rise apartment or office building, the designated response area may be limited to the building and/or the building and an outside area immediately adjacent to the building due to the length of travel within a high-rise Referring to FIG. 22, a block diagram of a computer-implemented method for registering equipment is shown. The method 2200 is, however, an example only and not limiting. The method 2200 can be altered, e.g., by having stages added, removed, rearranged, combined, and/or performed concurrently. The method 2200 is described with further reference to FIG. 1 and FIGS. 23-28.

Figure 17A:
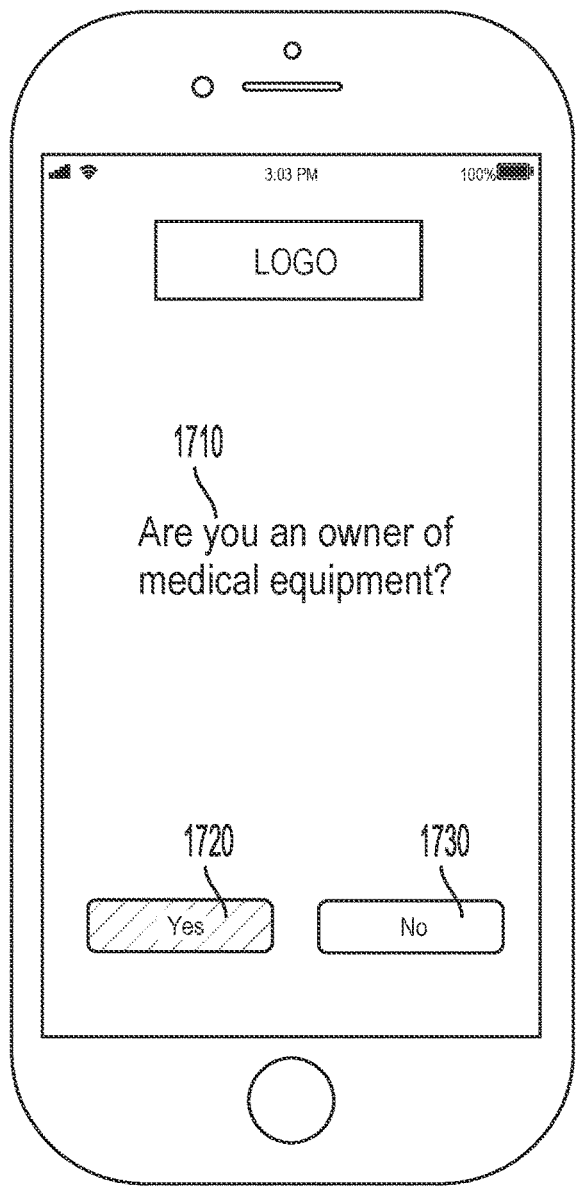
FIGS. 17A and 17B show examples of equipment registration queries of the software application
Figure 17B:
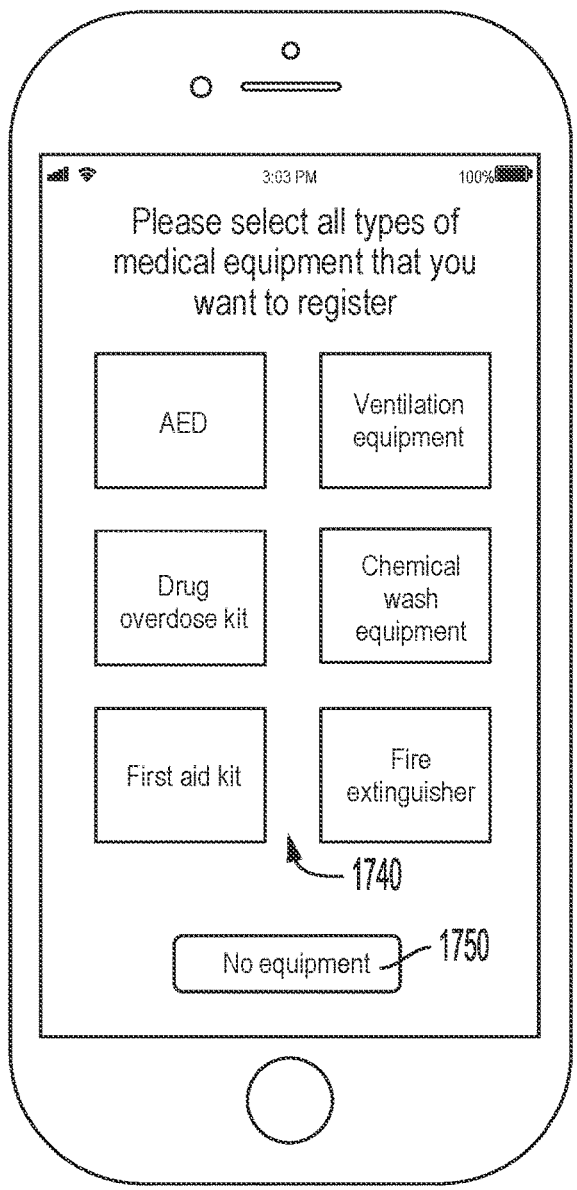

At stage 2210, the method 2200 includes receiving a request to register equipment. For example, as shown in FIGS. 17A and 17B and described above with regard to the stage 1455 of the method 1400, the registered responder may opt to register one or more items of medical equipment. As another example, an equipment owner may register equipment via the software application 225 separately from a responder registration process via an equipment registration interface 2310 as shown, for example, in FIGS. 23A and 23B.

At stage 2220, the method 2200 includes receiving equipment manager information. As shown, for example, in FIGS. 23A and 23B, the equipment owner or administrator may provide contact information 2320, account information 2330, and/or equipment source information 2340. The contact information 2320 may include one or more of name, email address, telephone number, time zone, business name, business phone, business email, and/or physical address. Each user interface presented in the equipment registration process may include a save control 2390. Selection of the save control 2390 may cause the software application 225 to save the information locally on the computing device 220 or 240 and/or may cause the management system 270 and/or the equipment registration system 260 to receive and store the registration information in the medical equipment database 280.

At stage 2230, the method 2200 includes receiving equipment location information. As shown for example, in FIG. 23B, the business name, phone, email, and/or address may correspond to a business location at which the medical equipment is stored. Alternatively, the business items in FIG. 23B may be part of the contact information for the owner/administrator. In an implementation, the stage 2230 may include designating the equipment location as public, private, or mobile.

Figure 24:
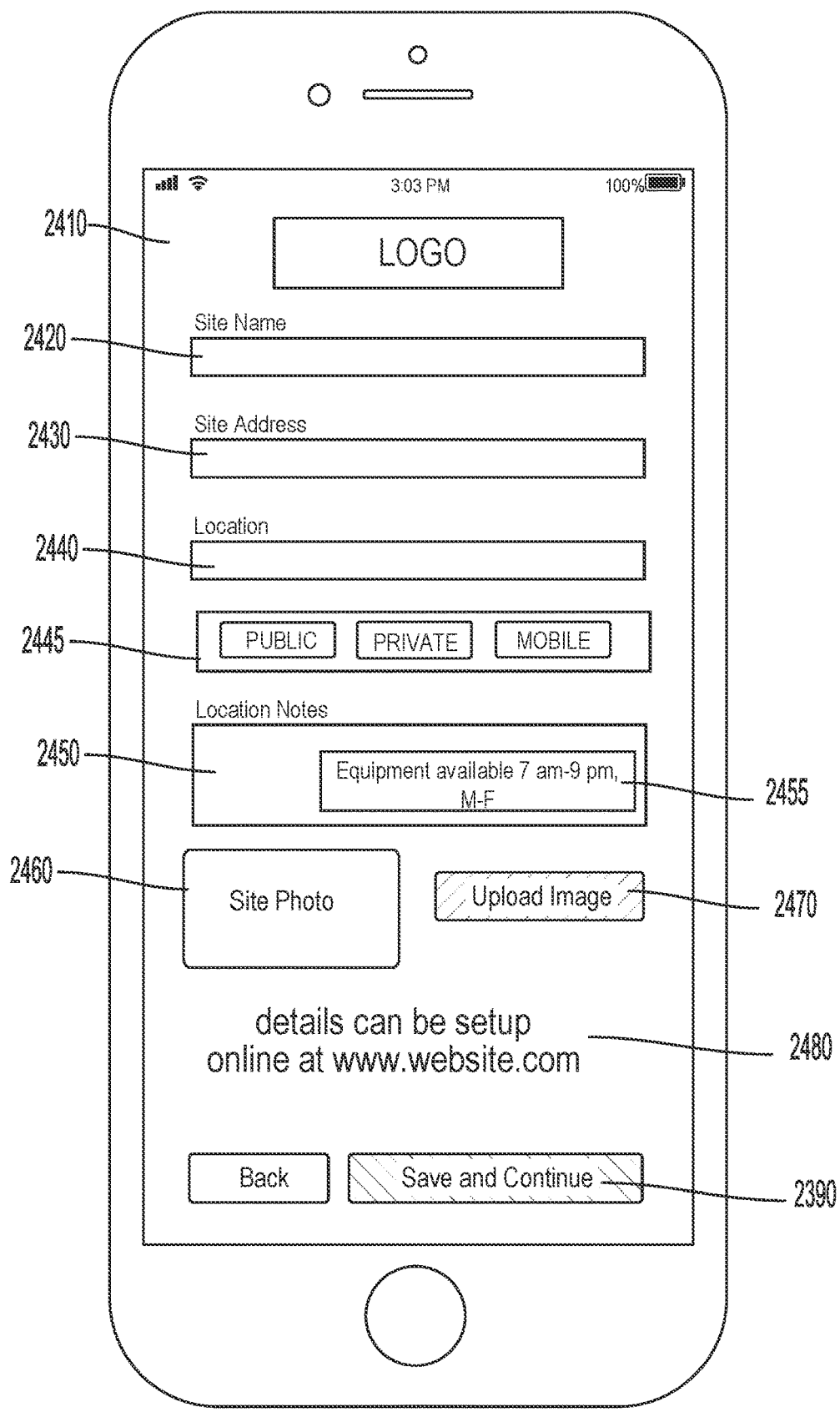
FIG. 24 shows an example of an equipment registration window of the software application.
Figure 25:
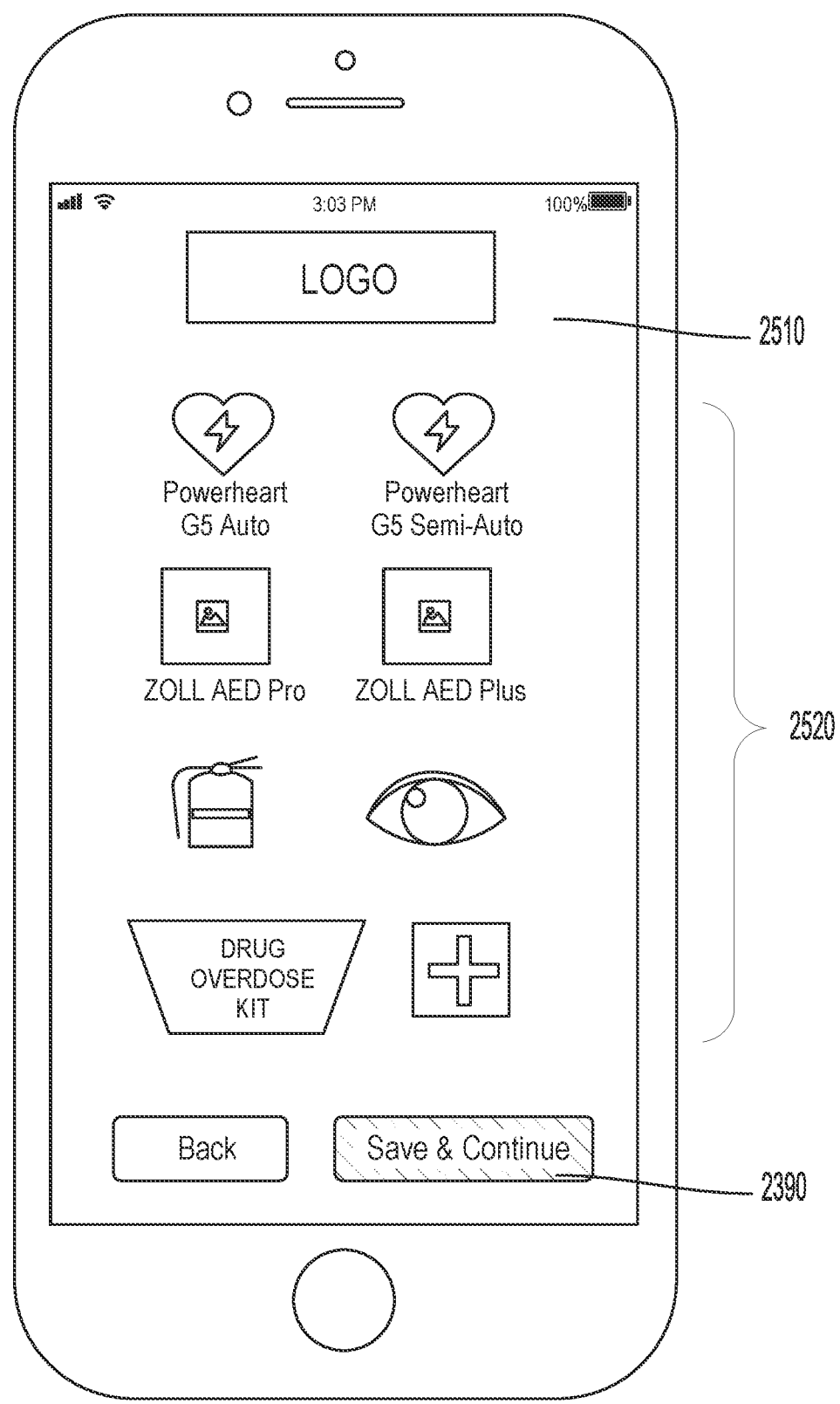
FIG. 25 shows an example of an equipment registration window of the software application.

Referring to FIG. 24, the software application 225 may provide an equipment storage location user interface 2410. The interface 2410 may enable the owner/administrator to provide a site name 2420, for example, a name of a building or location such as "Post Office," "Acme Pharmacy," "Smartville Elementary School," "Sleepytime Hotel," etc. The interface 2410 may further enable the owner/administrator to provide a street address 2430 for the site, an equipment storage location 2440, and/or storage location notes 2450. For example, the storage location 2440 may refer to a physical location within the site such as "main lobby," "front counter," "Flyfast Airlines Baggage Claim," etc. The software application 225 and/or the management system 270 may determine and store a geolocation referenced to global coordinates and determined from the user input location.

The location notes 2450 may include any special instructions such as "receptionist has key to storage area." The storage location notes 2450 may also include time availability information 2455. The interface 2410 may refer the user to a website (e.g., instructions 2480) accessible via the computing device 220 and/or the computing device 240. The user may access the software application 225 and/or the equipment registration interfaces via the website.

The equipment location designation option 2445 may enable the owner/administrator to designate the equipment location as public, private, or mobile. A public designation indicates that the general public may have access to the equipment storage location with possible time limitations. For example, a storage location at an airport, a shopping center, or a library may have a public designation. A private designation may indicate that the access to the equipment storage location may be limited to persons associated with a particular location. For example, a storage location in a school may limit access to students, teachers, administrators, and/or other school personnel because the doors of a school are generally locked and there are security limitations on who may enter the building. A government facility, military facility, or private club may be other examples of private designations. A mobile designation may indicate that the storage location is mobile, for example in a vehicle such as an ambulance, a fire truck, a police car, a tow truck, etc. As a further example, equipment and/or medications on a hospital crash cart may be moved around a hospital routinely and, therefore, the storage location might change within the hospital.

At stage 2240, the user may opt to upload an image of the equipment. For example, the interface 2410 may include a storage location photograph 2460 and/or an equipment image control 2470. The control 2470 may enable the user to upload the photograph 2460. If the user opts to upload the image then the method 2200 proceeds to stage 2245 and includes receiving the uploaded equipment image. For example, the management system 270 and/or the equipment registration system 260 may store the uploaded image in the medical equipment database 280.

Figure 26:
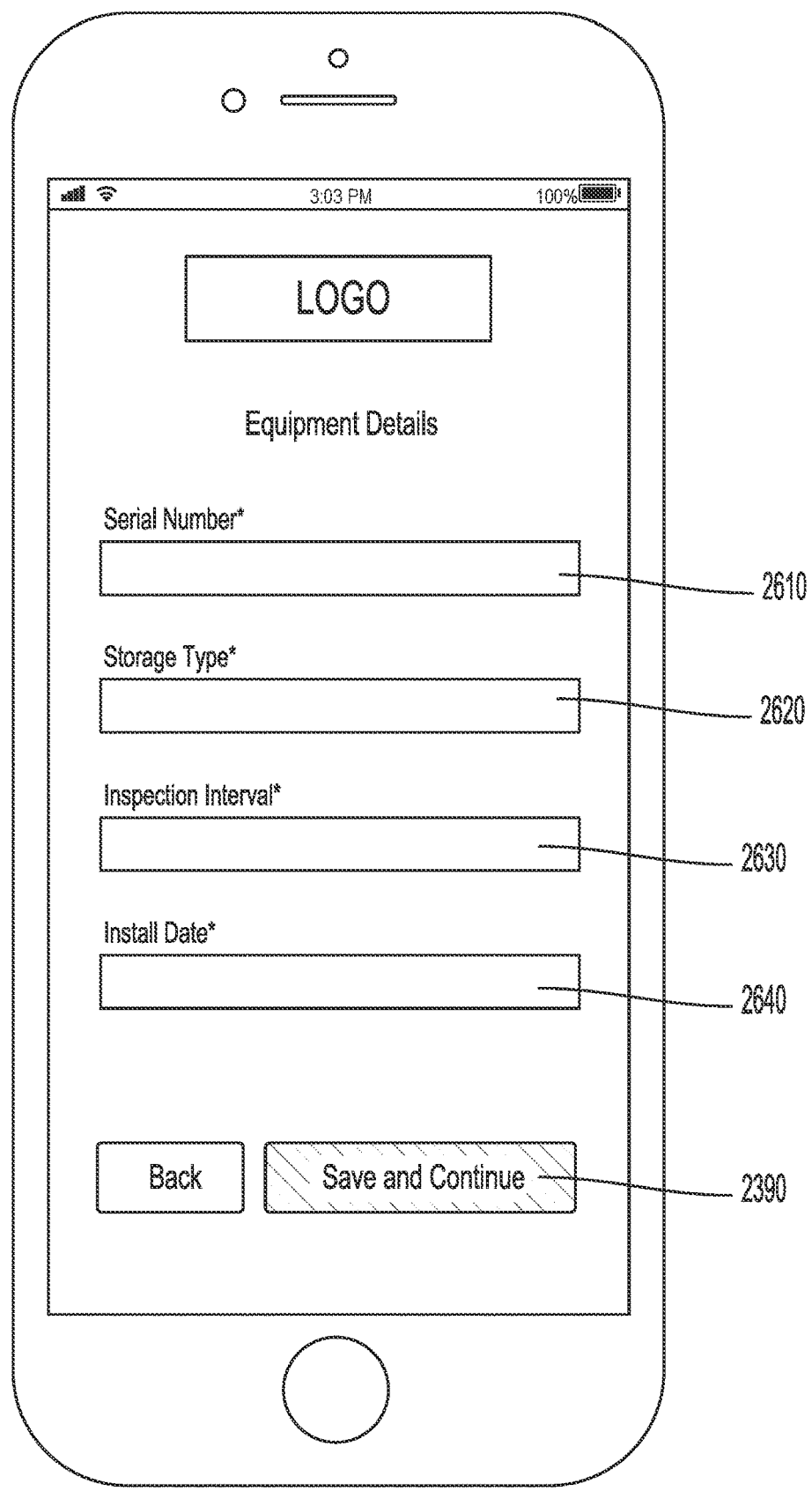
FIG. 26 shows an example of an equipment registration window of the software application.
Figure 27:
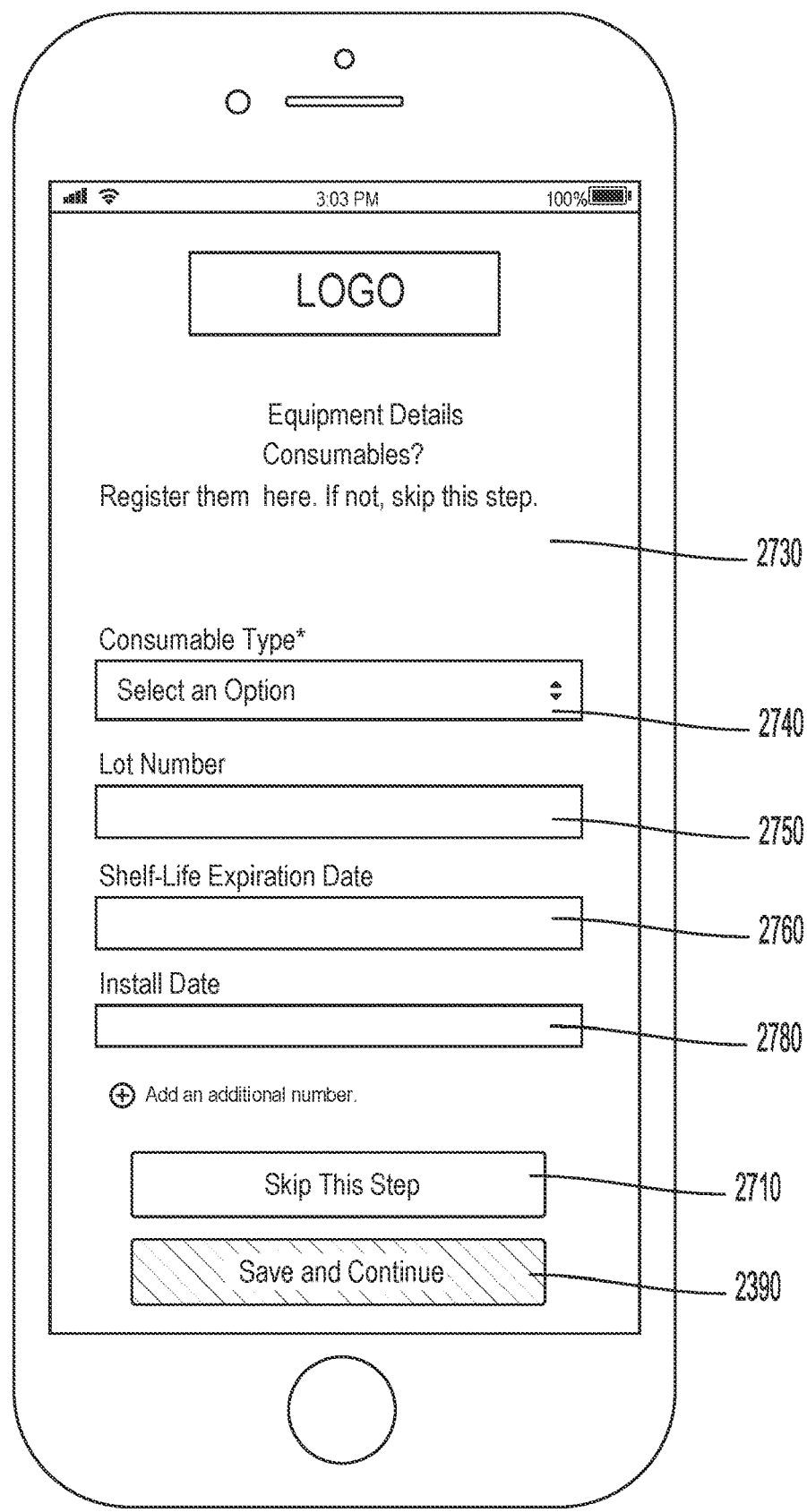
FIG. 27 shows an example of an equipment registration window of the software application.

At stage 2250, the method 2200 includes receiving information that specifies a type of medical equipment. For example, the software application 225 may provide an equipment selection interface 2510. The interface 2510 may include selectable controls 2520 (e.g., icons) and/or text indicative of various types and/or specific models of medical equipment. The interface 2510 may capture a user selection via a touch gesture, a mouse click, audio input, etc. Along with the type of equipment, the software application 225 may further prompt the user to provide identification information such as, for example, a serial number 2610 as shown in FIG. 26. In an implementation, the software application 225 may prompt the user to enter a storage type 2620 (e.g., cabinet, carrying case, backpack, docking station, clamshell, pelican case, cooler, etc.).

At stage 2260, the method 2200 includes receiving inspection and/or installation information for the medical equipment. For example, as shown in FIG. 26, the software application 225 may prompt the user to enter an inspection interval 2630 and/or an installation date 2640 for the medical equipment. The inspection interval 2630 may indicate a frequency of inspections expected for the medical equipment, such as, for example, once per hour, once per day, once per week, once per month, once per 2 months, once per six months, once per year, once per power on, once per emergency call, once per work shift, etc. In an implementation, the management system 270 may determine a lifetime and/or expiration date for the equipment and/or equipment components based on the installation date 2640. In an implementation, as described above with regard to FIG. 19, the management system 270 may determine equipment operational status based at least in part on the inspection interval and/or the installation date.

At stage 2270, the method 2200 includes receiving an indication from the user as to whether or not the equipment includes consumables. Consumables may be any parts, components, supplies etc. associated with the medical equipment 230 that may have a limited lifetime after which they are no longer effective or usable (e.g., an expiration date). In an implementation, the consumables are stored with the medical equipment 230. If the user does not need to register consumables then they may select a skip option 2710 and the method proceeds to the stage 2290. If the user does want to register consumables, then the method proceeds to the stage 2275.

At stage 2275, the user may enter consumables information at a consumables interface 2730. The consumables information may include manufacturer identification information 2750, expiration information 2760, and/or installation date information 2780. Further, the consumables information may include an identification 2740 of a type of consumable. For example, consumable types may include battery, defibrillation pads, medications, chemical solutions, sensors, electrodes, adhesives, fire extinguishing chemicals, propellants, mechanical components, light and/or heat sensitive components, single use components, etc. In an implementation, as described above with regard to FIG. 19, the management system 270 may determine equipment operational status based at least in part on the consumables information 2750, 2760, and/or 2780.

At stage 2280, the method 2200 includes prompting the user to indicate whether or not they wish to register more items of equipment. In an implementation, the software application may provide a registration continuation screen 2805 as shown for example in FIG. 28A. If yes, then the method 2200 returns to the stage 2230. If no, then the method 2200 ends at stage 2290 and the user exits the equipment registration process.

Figure 28A:
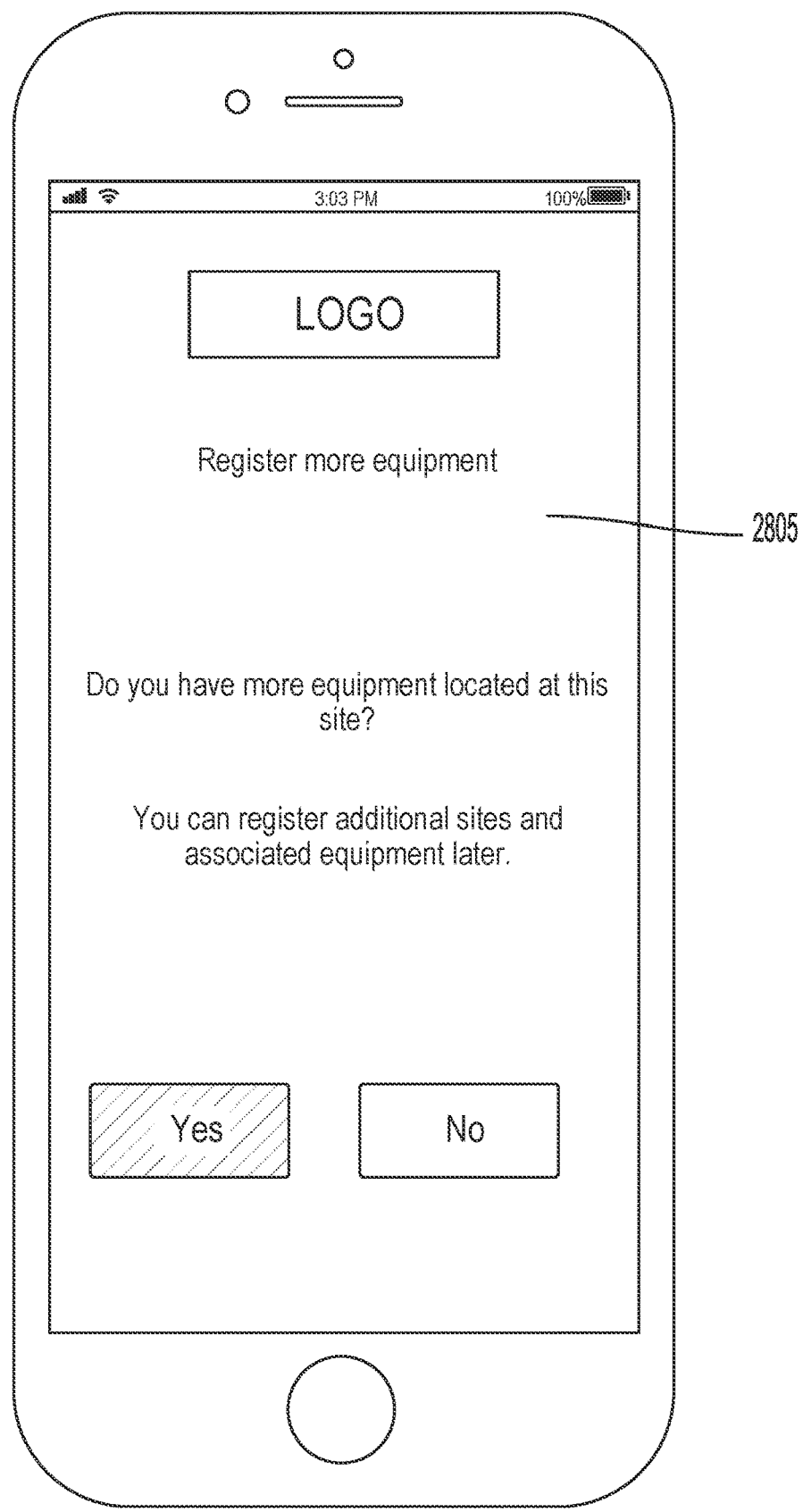
FIG. 28A shows an example of an equipment registration window of the software application.
Figure 28B:
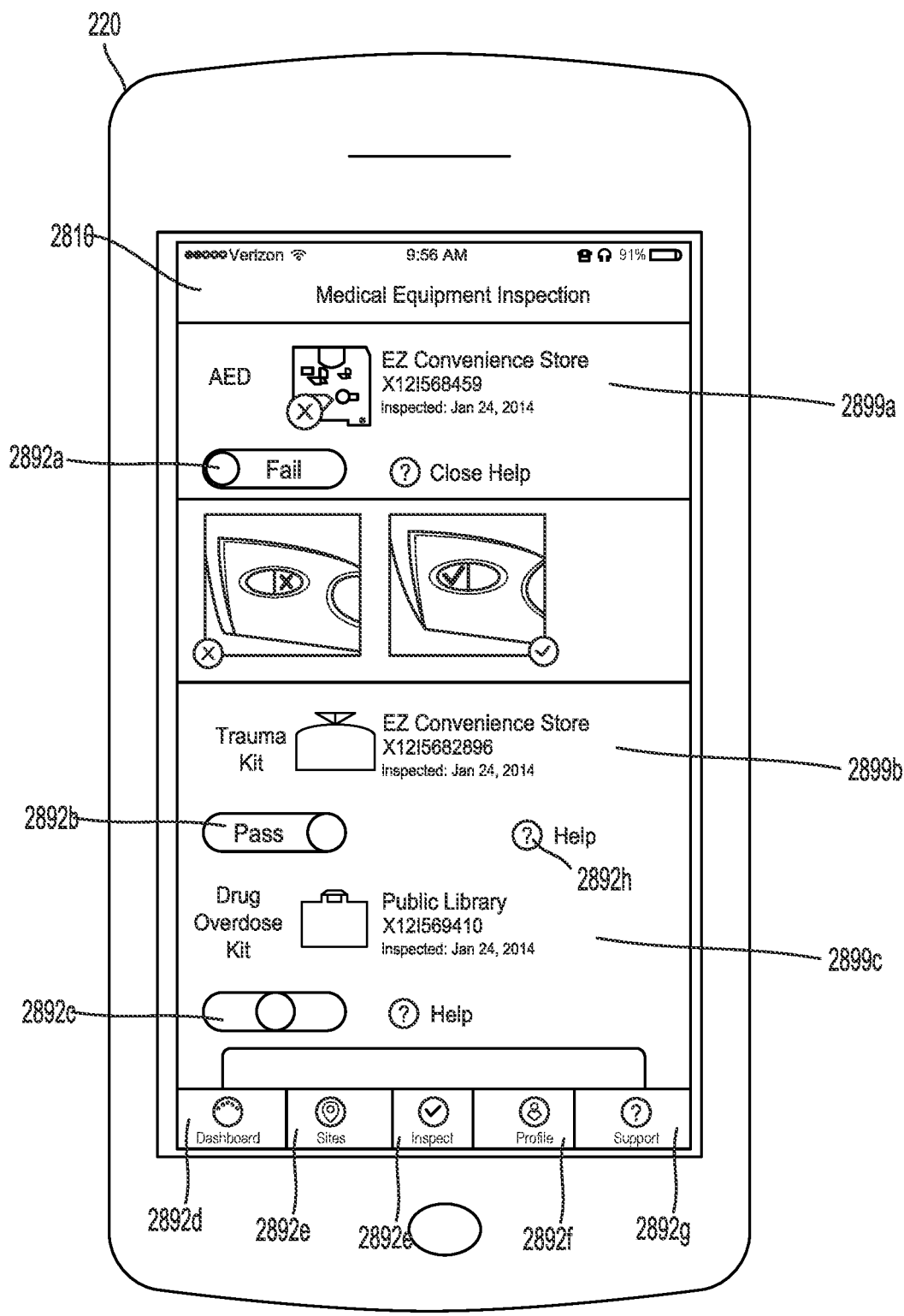
FIG. 28B shows an example of an equipment inspection screen of the software application.

Referring to FIG. 28B, in an implementation, the software application 225 may include a medical equipment inspection user interface, for example, the inspection user interface 2810 shown in FIG. 28B. Via the inspection user interface, the software application 225 may capture inspection information that is input to the user interface for the medical equipment. The inspection user interface 2810 is an example of an inspection information entry screen. For example, the inspection user interface 2810 may include multiple user inputs, e.g., 2892*a*, 2892*b*, 2892*c*, 2892*d*, 2892*e*, 2892*f*, 2892*g*, and 2892*h*. In this example, the user inputs 2892*a*-2892*c* enable input of inspection information that is received by the software application 225 and the management system 270. In an implementation, the management system 270 may store the inspection information in the equipment database 280. Inclusion of the inspection user interface 2810 in the software application 225 may enable crowd-sourced inspections of publicly accessible medical equipment. The registered responders may provide the equipment inspection information via the software application 225. The user inputs 2892*d*-2892*h* enable input of user selections of various functions of the software application 225. For example, the inspection interface 2810 may provide medical equipment information 2899*a*, 2899*b*, and 2899*c* for various types and locations of medical equipment. The AED, trauma kit, and drug overdose kit are examples only and not limiting of the disclosure. For example, the medical equipment may include public safety equipment and/or supplies, emergency equipment and/or supplies, and/or hospital equipment and/or supplies. The medical equipment information 2899*a*, 2899*b*, and 2899*c* may indicate one or more of the type of medical equipment, the location of the equipment, a serial number, brand, and/or model of the equipment, and a date of last inspection. Via the inspection user interface 2810 of the software application 225, the registered responder may select the medical equipment for inspection. For example, the user may tap on an item of medical equipment to select that item of medical equipment for inspection via the survey map 1910 as shown in FIG. 19. On the user interface 2810, the user may provide a status of the selected medical equipment and/or components thereof (e.g., battery, electrodes, drugs, sensors, consumables, etc.) via the user input 2892*a*, and/or order replacement parts or repairs. For example, as shown in FIG. 28A, the AED at the EZ Convenience store has a "fail" status for the inspection and the trauma kit at the same location has a "pass" status of the inspection. Further, the date of the inspection is shown.

In addition to, or as an alternative to, capturing inspection information provided to the user interface 2810, the software application 225 and/or the management system 270 may be configured to capture information transmitted by the medical equipment 230. For example, the software application 225 may receive signals transmitted by the medical equipment over a wired and/or wireless connection (e.g., the network(s) 250) between the medical equipment 230 and the computing device 220. As another example, the management system 270 may receive signals transmitted by the medical equipment over a wired and/or wireless connection (e.g., the network(s) 250) between the medical equipment 230 and the management system server 272. The information transmitted by the medical equipment 230 may include location information, identification information, a media access control (MAC) address, and/or an internet protocol (IP) address and/or other network address.

In an implementation, the medical device information (i.e., the information transmitted by the medical equipment 230 and received by the software application 225 and/or the management system 270) may include status and/or inspection information. The medical device information may include status and/or inspection information for an item of medical equipment as a whole and/or status and/or inspection information for one or more components and/or accessories. The medical device information may include expiration dates, inspection dates, order information, replacement information, and/or information on upcoming dates for replacement and/or inspections of components and/or accessories. The status information may include self-test and/or diagnostic results, such as a self-testing report transmitted automatically and periodically (e.g., daily, weekly, monthly, or at another administrator specified interval). The medical equipment may perform a self-test either automatically or upon user initiation. The medical device information may additionally or alternatively include software update and/or configuration information. In an implementation, the medical device information may be specific to the particular type of medical device. For example, the medical device information for an AED may include battery information, electrode pad information, and/or information for other consumable components. The medical device information for a drug delivery device may include a drug expiration date. The medical device information for a fire extinguisher may include inspection information such as a pressure gauge reading. The medical device information for a first aid or trauma kit may include battery information, supply inventory, expiration dates for drugs and/or other consumables, and/or inspection information. The supply inventory may include inventory for one or more of tourniquets, airway kit, dressings, chest seals, bandages, gauze, splints, compresses, adhesive tape, face shields, aspirin and/or other analgesics, allergy medications, glucose, blankets, chargers, biohazard markers, shears, gloves, user manual, eye pads, burn cream, antibiotics including antibiotic ointments, antiseptic wipes, tweezers, hand sanitizer, eye wash, and/or a first aid guide.

Figure 30A:
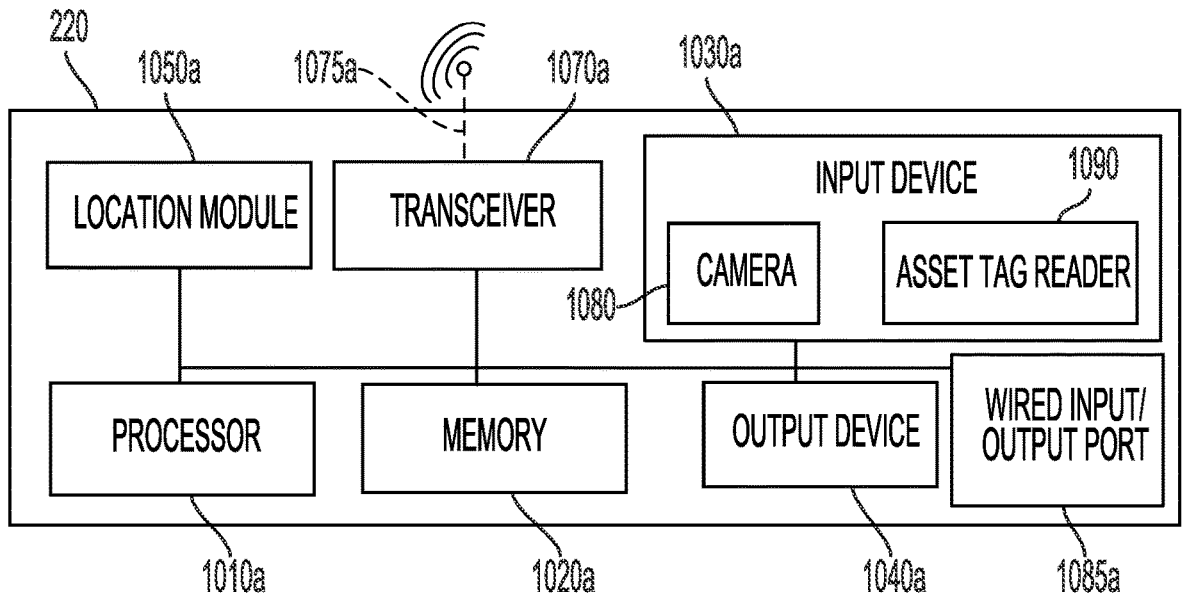
FIG. 30A shows a schematic diagram of an example of computing device components.

Alternatively, or additionally, the software application 225 may capture medical equipment information via the input device 1030a (e.g., via the camera 1080, the asset tag reader 1090, and/or another component of or type of input device 1030a of the computing device 220 as shown in FIG. 30A). For example, the medical equipment may include an asset tag (e.g., a barcode and/or radio frequency identification (RFID) tag) compatible with the asset tag reader 1090.

The systems and methods described herein may enable otherwise independent personnel to provide a coordinated, efficient, and speedy response to an emergency event. In particular, the time from an occurrence of an emergency event to arrival of the lay responders and therapeutic intervention can be significantly reduced and additional lives saved. For instance, as the American Heart Association has stated, every minute of delay in therapy for the cardiac arrest victim results in a 10% decrease in survival.

In some cases, the system 270 may manage multiple responders. For example, one responder may acquire the AED and/or other medical equipment and two other responders may proceed directly to the victim. The system 270 may instruct the first of these two responders to arrive at the victim to start chest compressions and may instruct the second of these two responders to arrive to start ventilation. The responder acquiring the medical equipment may arrive after the other two have started treatment.

The systems and methods described herein may enable a coordination of response between persons registered as responders with the management system 270 and other emergency services and personnel including, but not limited to, EMS agencies. In some cases, an EMS agency may be available to provide professional responders and/or medical equipment and/or supplies even if they are not officially dispatched to the emergency event. For example, these professional responders may enable location tracking of an associated computing device and/or vehicle. The management system 270 may tie in to existing emergency vehicle navigation, dispatch, and tracking systems to receive location information for these vehicles and personnel. In an implementation, the management system 270 may display this information to the registered responders via the software application 225. As another example, the medical equipment and/or supplies of the EMS agency may be registered with the management system 270 as non-publicly accessible medical equipment available via the EMS agency.

In an implementation, one or more of the estimated travel times to equipment and/or to the emergency event (e.g., the travel times shown on the interactive map 410 by the indicators 460a and 460b) may include an interior travel time. The interior travel time may be a time between when a responder enters a facility or area in which the registered medical equipment is stored and when the responder arrives at the storage location within the facility or area. The management system 270 may access an indoor map and/or indoor mapping information for the facility or area to determine the interior travel time. Although referred to as an "interior" travel time and an "indoor" map, the facility or area may be outdoors, indoors, or a combination thereof. This map may include three-dimensional location information (e.g., latitude, longitude, and altitude). The three-dimensional location information may include global coordinates (e.g., latitude, longitude, and altitude) and/or descriptive information (e.g., a location on a floor of a building which may include a descriptor such as office, lobby, breakroom, corridor, courtyard, etc. and an indication of which floor of a building, such as, "equipment is located on the third floor of the building in Office Number 52 in the north-east corner). For example, the facility or area may be a multi-story building and the medical equipment may be stored on the second floor. The interior travel time may indicate the time to traverse the distance from the entryway of the building to the second floor location and then to return to the entryway of the building. The software application 225 may provide one or more interior route options for the registered responder (e.g., using stairs, elevator, various hallways, various entryways, etc.) and may adjust the interior travel time dynamically based on the route of the responder. The software application 225 may provide a recommended interior route having a shortest travel time compared to other interior routes. In an implementation, the facility or area may have one or more items of registered medical equipment and these items may be of different types. The software application 225 may recommend particular item(s) based on the type of emergency event and/or skills or proficiencies of the registered responder and/or equipment available to and/or recommended by an EMS agency responding to the emergency event. In an implementation, the software application 225 may display the interior travel time in response to a touch screen gesture at the location indicator for the medical equipment and/or at the indicators of the estimated travel time on the interactive map 410.

The systems and methods described herein may include and enable the capability of the management system to provide suggested and/or recommended navigation routes for responders from a current location to an equipment location and/or an emergency event location. The management system may track responder locations and may determine the navigation routes based on the tracked responder location. For example, the management system 270 may provide the interactive map 410 to the computing device 220 associated with the responder 110. Further, the management system 270 may provide the interactive map 410 to multiple computing devices associated with multiple responders. In an implementation, each responder may view their own navigation activities along with the activities of other responders on their own computing device. The interactive map 410 may include an indicator of the emergency event location along with one or more location indicators for registered medical equipment. The management system 270 may limit the location indicators to those associated with and/or representing registered medical equipment in the vicinity of the emergency event. The management system 270 may track the locations of one or more computing devices associated with registered responders and provide the tracked locations to one or more of the responders via the interactive map. For at least one or for each tracked responder, the management system 270 may determine one or more first navigation routes between the current location of the tracked responder and the registered medical equipment locations. Further, the management system 270 may determine an estimated travel time for at least one or each of the one or more first navigation routes. Additionally, the management system 270 may determine one or more second navigation routes between the registered medical equipment locations and the emergency event location. Further, the management system 270 may determine an estimated travel time for at least one or each of the one or more second navigation routes. In an implementation, the management system 270 may limit the registered medical equipment for which routes are determined based on one or more of the estimated travel times, the type of medical equipment, the type of emergency event, and/or the training and/or proficiency of the registered responder. Further, based the one or more of the estimated travel times, the type of medical equipment, the type of emergency event, and/or the training and/or proficiency of the registered responder, the management system 270 may recommend at least one item of registered medical equipment for at least one or each registered responder. The management system 270 may provide a recommendation of the first navigable route and/or the second navigable route to/from the recommended registered medical equipment. The management system 270 may determine the recommendation based at least in part on the estimated travel times for the various first navigable routes and second navigable routes. The management system 270 may update the recommendations of routes and/or registered medical equipment based on the tracked location of the registered responder. The types of registered medical equipment may include one or more of a patient monitor, an external defibrillator, an automated external defibrillator, ventilation equipment, drug delivery equipment, a physiological sensor, a fire extinguisher, an oxygen tank, a drug overdose kit, a first aid kit, a trauma kit, tourniquet equipment, eye wash equipment, an epinephrine auto-injector, and chemical exposure equipment. In an implementation the management system 270 may change an appearance of one or more map indicators (e.g., icons, text, graphics, etc.) in order to indicate the recommendation. For example, the appearance (e.g., shape, size, color, flashing/steady display, etc.) of the location indicator for the recommended item of registered medical equipment may be different than for other items of medical equipment represented on the interactive map 410. Further, the management system 270 may change an appearance (e.g., shape, size, color, flashing/steady display, etc.) of the recommended navigable route compared to the other navigable routes provided on the interactive map 410. The recommended navigable route may be a route to/from the registered equipment and/or to the emergency event. In an implementation, the responder may separately and/or sequentially select the first navigable route to the medical equipment and the second navigable route to the emergency event. In an implementation, the responder may indicate a selection of a particular navigable route via the interactive map 410. For example, the responder may tap on the particular navigable route to indicate the selection. In response, the management system 270 may further change the appearance of the selected navigable route to an appearance that is different from the appearance of unselected routes, non-recommended routes, and/or recommended routes. In an implementation, the management system 270 may dynamically change the selected navigable route to reflect the tracked location of the responder and/or may dynamically offer alternative routes based on the tracked location and/or events occurring along the routes (e.g., traffic and/or other impediments to vehicular and/or foot traffic). In an implementation, the responder may provide confirmation of acquisition of the registered medical equipment via the software application 225 and/or the interactive map 410. For example, the responder 110 may tap on a location indicator for the equipment and/or respond to a prompt to confirm that he/she has acquired an item of registered medical equipment. In an implementation, the management system 270 may determine the navigable routes between the equipment and the emergency event and/or the recommendations of the navigable routes in response to and/or based on the confirmation of acquisition of the registered medical equipment. In various implementations, the management system 270 may determine the estimated travel times based on a mode of transport of the responder. The management system 270 may use a default mode of transport and/or may prompt the responder to indicate the mode of transport and use the indicated mode of transport. The mode of transport may be, for example, but not limited to, walking or running or vehicular (e.g., driving, biking, public transportation, ambulance, fire truck, etc.). The management system 270 may estimate the travel times using an assumed, estimated, and/or default speed associated with the mode of transport. In limiting the displayed items of registered medical equipment to those in a vicinity of the emergency event, the management system 270 may define the vicinity of the emergency event as an area including locations less than or equal to a particular distance from the emergency event. In an implementation, the management system 270 may determine the vicinity of the emergency event based on the speed associated with the mode of transport. Thus the vicinity of the emergency event may be an area including locations from which the responder can reach the emergency event location within a particular amount of time. For example, the area may include locations that are 1 minute, 2 minutes, 3-5 minutes, 3-10 minutes, 10-30 minutes, 1-60 minutes, etc. away from the emergency event based on a walking speed, running speed, or vehicular speed. The time may depend on the type of emergency event, the skills of the responder, the type of medical equipment provided by the responder, the locations of professional responders or other medical personnel, the number of victims, the number of responders, the locations of medical equipment, etc. In an implementation, the management system 270 may indicate an order of medical equipment based on proximity and/or travel time to the emergency event. The management system 270 may indicate the order as a list and/or via appearances of interactive map icons and/or via text and/or graphics provided by the software application 225. The ordering may depend on the travel time to the medical equipment and/or to the emergency event. In an implementation, the estimated travel times to the equipment and/or from the equipment to the emergency event may include time needed for a responder to locate the equipment within a storage location, e.g., an interior travel time. For example, if the medical equipment is located inside of a building, it will take the responder a certain amount of time to reach the equipment once they enter the building and then additional time to exit from the building. Thus, the management system 270 may estimate the amount of time to reach the equipment once the responder enters the facility and/or the equipment database may include a pre-determined time for use by the management system 270 in determining estimated travel times. In an implementation, the management system 270 may access an interior map of the storage location and estimate or determine the interior travel time based on the interior map. Although referred to as an "interior" map, the storage location may be indoors, outdoors, or a combination thereof. For example, the storage location may include a courtyard, balcony, and/or rooftop area and/or may be a facility such as a stadium, airport, shopping center, etc. that may include indoor and/or outdoor areas. The interior map may be a three-dimensional map that includes multiple floors or stories and may include stairways and/or elevators. The navigable routes determined by the management system 270 may be indoor routes, outdoor routes, and/or combinations thereof. The routes shown on the interactive map may provide a graphic representation of turn-by-turn directions for the responder and/or the software application 225 may provide these directions in a list or other text and/or audible format. In an implementation, the management system 270 may provide a directions control and provide the turn-by-turn directions in response to a user selection of the directions control.

The systems and methods described herein may include and enable management, by the management system 270, of a variety of types of medical equipment. As a result, the management system 270 and the software application 225 may enable response to a variety of types of emergency events by responders with various training and degrees of proficiency. In an implementation, the management system 270 and the software application 225 may tailor the responder selection and/or equipment selection to the type or category of emergency event. Further, the management system 270 and/or the software application 225 may tailor the equipment selection and/or equipment acquisition recommendation to the skills and/or proficiencies of the responders. The management system 270 may use the software application 225 to coordinate multiple responders for a single emergency event. Such coordination may include assignments of registered equipment to specific responders and/or designating some responders to acquire medical equipment and other responders to proceed to the emergency event without acquiring medical equipment. In an implementation, the management system 270 may provide the emergency assistance request to one or more computing devices 220 via the software application 225. The emergency assistance request may include the location of the emergency event and an emergency response category. For example, the emergency response category may include trauma, drug overdose, cardiac arrest, respiratory distress, or a combination thereof. The emergency event may include one or more victims. Thus, the emergency response category may be one or more categories for a single victim or may be one or more categories for each of multiple victims. The emergency assistance request may further include medical equipment information for one or more items of registered medical equipment. This information may include the location of the registered medical equipment along with an indication of the type of medical equipment. For example, the medical equipment may be a trauma kit, a drug overdose kit, a ventilator or combinations thereof. As further examples, the medical equipment may be a defibrillator, a patient monitor, drug delivery equipment, a physiological sensor, a fire extinguisher, an oxygen source, tourniquet equipment, eye-wash equipment, an epinephrine auto-injector, and/or chemical exposure equipment. The management system 270 may receive a selection of one or more items of registered medical equipment from the responder via the software application 225. In an implementation, the management system 270 may determine the medical equipment presented to the responder for selection based on one or more of the location of the emergency event, the emergency response category, and/or the medical equipment information. Alternatively or additionally, the responder may select the medical equipment based on one or more of the location of the emergency event, the emergency response category, and/or the medical equipment information. In response to the selection of the one or more items of registered medical equipment and/or an acceptance of the emergency assistance request, the management system 270 may track a location of a computing device 220 associated with the registered responder. The management system 270 may track locations of multiple computing devices associated with multiple registered responders for one or multiple emergency events. Based on the tracking and/or the selection of medical equipment, the management system 270 may provide navigation instructions for a route between the tracked location of the computing device and one or more of the location of the selected medical equipment and the location of the emergency event. In an implementation, the management system 270 may select responders based on responder training and/or skill proficiency for the category of emergency response. For example, the management system 270 may receive an acceptance of the emergency assistance request from multiple responders. The acceptance may designate these responders as candidates. The management system 270 may select a subset of the candidates to respond to the emergency event and/or to acquire emergency medical equipment and/or supplies. For example, the management system 270 may provide the location of the emergency event to multiple computing devices from the responder registration database. In response, the management system 270 may receive an availability indication from one or more the multiple computing devices. The availability indication is an indication that the computing device has determined itself (e.g., self-determined) to be location in a vicinity of the emergency event location. For example, the computing device 220 may have location information based on GPS, base station locations, mapping information, context information etc. from which the computing device 220 knows its geographic and/or mapped location. The computing device 220 may compare its location information to the location of the emergency event. The computing device 220 may determine itself to be within a certain distance and/or particular travel time from the emergency event. In various examples, the vicinity of the emergency event may correspond to a distance traversable by the responder within a pre-determined response time. The pre-determined response time may depend on the emergency response category. For example, some emergency situations may benefit from a faster medical response than others. The distance traversable by the responder with the pre-determined response time may depend on an assumed or indicated mode of transport (e.g., walking, running, vehicular, etc.). The management system 270 may use an assumed speed and/or a speed provided by the responder to determine the response time. The response time may indicate the amount of time it will take for the responder to reach the medical equipment and/or the emergency event from a current location of the responder. In some implementations, the response time and/or the distance traversed by the responder may include a distance from an entryway to a facility that houses the registered medical equipment to a storage location of the medical equipment within the facility. In some instances, the vicinity of the emergency event may be a distance traversable by the responder in 1-4, 1-10, 10-20, 5-60 minutes, etc. Additionally or alternatively, the vicinity may be define by a distance from the emergency event, for example, 0-400 meters, 200-800 meters, 0-1 km, 1-5 km, etc. This distance may depend on a population density of an area and/or proximity of professional responders to the emergency event. In response to receiving the availability indication from the computing device 220, the management system 270 may access and/or receive responder profile information for the responder(s) associated with the available computing device(s). In an implementation, the management system 270 may provide the emergency assistance request to one or more computing devices based on the responder profile information. For example, the responder profile information may include responder training information and/or information regarding the proficiency level of the responder for one or more types of emergency event. For example, one responder may be trained to use a drug overdose kit but not a ventilator. As other examples, the proficiency level may include one or more of basic first aid for trauma, advanced first aid for trauma, lay rescuer for adult CPR, lay rescuer for pediatric CPR, professional rescuer for adult CPR, professional rescuer for pediatric CPR, lay rescuer for defibrillation, and professional rescuer for defibrillation. In an implementation, the management system 270 may recommend one or more particular items of registered medical equipment to a particular responder based on the responder profile information. For example, the medical equipment registration database may include medical equipment information that may indicate user support information provided by the equipment. Depending on training and/or proficiency, various responders may need and/or prefer various levels of user support information. For example, the user support information for a particular item of medical equipment may include CPR prompting and/or CPR feedback. The user support information may also indicate a rescuer skill level that is appropriate for the user prompting and/or user feedback provided by the equipment. For example, one item of equipment may include prompting, instructions, and/or feedback to guide a lay responder through use while another item of equipment may only include prompting, instructions, and/or feedback to guide trained medical personnel through use.

In some examples, the system 270 may provide for more than one responder to be sent to the event. In an implementation, the system 270 may coordinate with responder management by the emergency dispatch service 125 (e.g., a CAD). In an implementation, the responder and equipment management system 270 may coordinate responders to expedite the arrival of a responder providing non-equipment-based life-saving activities. For example, the system 270 may identify one or more first responders to get one or more pieces of medical equipment such as an AED, ventilator, trauma kit, or drug overdose kit (e.g., NARCAN®). The system 270 may identify one or more second responders to proceed straight to the victim and begin life-saving activities such as cardiopulmonary resuscitation activities (e.g. chest compressions and/or ventilations) and/or first aid (e.g., compress a bleeding wound, remove an object that has fallen on a person, etc.). If the second responder, who does not have to go out of their way to find the AED or other equipment nor carry a potentially heavy set of equipment can arrive even a minute earlier than the first responder and begin high quality chest compressions, then over the course of many emergency events, potentially thousands more cardiac arrest victims could survive.

Figure 29A:
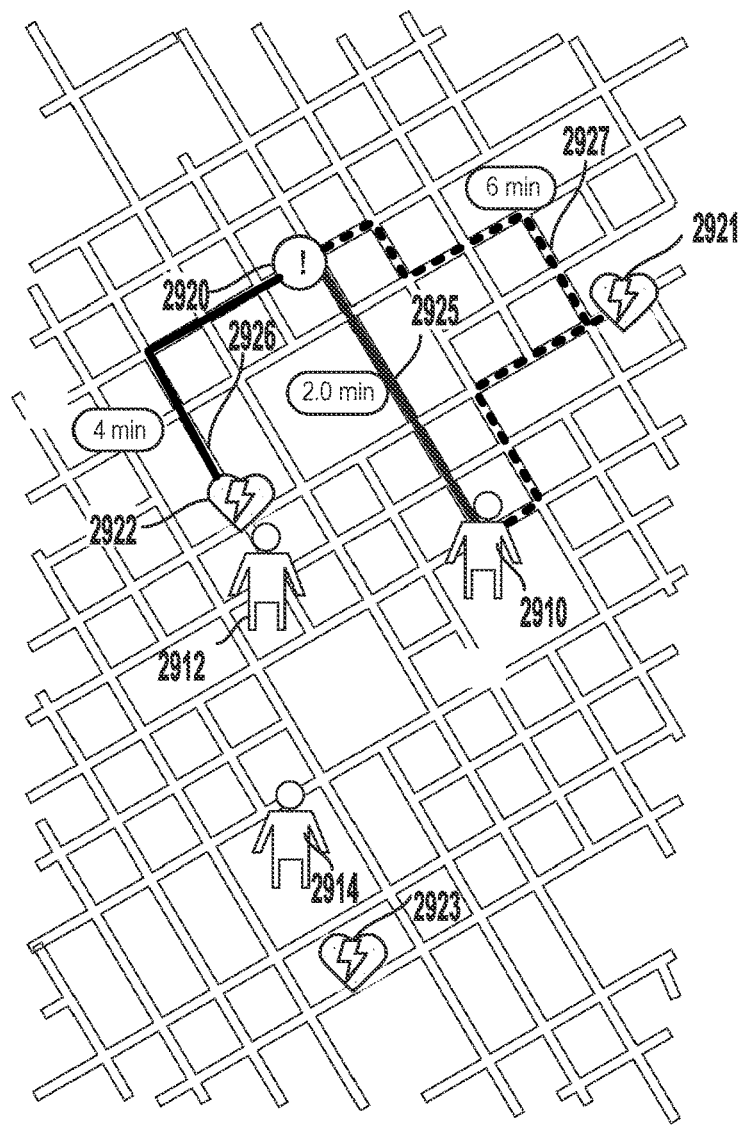
FIG. 29A shows an example of responder coordination by the medical equipment and responder management system based on time and distance.

Referring to FIG. 29A, an example of responder coordination by the medical equipment and responder management system based on time and distance is shown. In an implementation, the system 270 may coordinate (e.g., select and/or prioritize and provide instructions) to responders, for example, responders 2910, 2912, and 2914, based on transportation distance and/or response time. The system 270 may compute and/or estimate transportation or travel distance based on mapping information, responder location information (e.g., GPS, cellular triangulation, etc.), registered equipment locations, and emergency event location information from the dispatch service 125. For example, as shown in the table 2930, the system 270 may compute various travel times. The travel times, or response times, may be the time it takes a responder to travers a particular distance, for example, a distance between the current location of the responder and the emergency event, the distance between the current location of the responder (e.g., a current location of the mobile computing device associated with the responder) and the medical equipment, and the distance between the medical equipment and the emergency event. The management system 270 may further calculate a sum of the travel time between the current location of the responder and the medical equipment and the travel time from the medical equipment to the emergency event location. This sum corresponds to an estimate of the travel time from the current location of the responder to the emergency event inclusive of a medical equipment acquisition time. The medical equipment acquisition time may additionally include an estimate of the time needed to traverse an interior distance to a medical equipment storage location. If the responder needs to enter and exit a building to acquire the medical equipment and proceed to the emergency event, the interior travel time may include a time to traverse a distance between an entryway/exit to/from the building and the medical equipment storage location. These system 270 may calculate or estimate these distances based on mapping information in order to account for routing restrictions applicable to the responder. For example, the system 270 may not calculate the distance "as the crow flies" but rather the distance along a navigable route as defined by roads, sidewalks, stairwells, elevators, hallways, building entrance and exit locations, etc. The system 270 may assume a mode of transport, by foot or by vehicle, depending on user settings in the software application 225 and/or or vehicle awareness of the responder's computing device 220. Based on the mode of transport, an assumed speed of transport, and the distance, the system 270 may calculate or estimate a response time, or travel time, for the responders 2910, 2912, and 2914 within a vicinity of the emergency event 2920 to all registered medical equipment 2921, 2922, and 2923 within the vicinity of the emergency event (determination of the vicinity of the emergency event is discussed above, for example, with regard to FIG. 2A). Additionally, the system 270 may calculate or estimate the travel time from the registered medical equipment to the location of the emergency event. The system 270 may rank the responders according to increasing or decreasing travel time. The system 270 may select the responders with the fastest travel times (i.e., the smallest time interval relative to all of the responders) to the emergency event as the one or more second responders that proceed directly to the victim. In the example of table 2930, the system 270 may select responder 2910 to proceed directly to the emergency event 2920 along the route 2925 based on a calculated or estimated response time of 2 minutes (i.e., the system 270 may estimate that responder 2910 can traverse the route 2925 to the emergency event 2920 to reach the victim in 2 minutes). The system 270 may further select the one or more responders with the shortest total transit time from their current location to the medical equipment and then to the victim according to rank as the one or more first responders. In the example of table 2930, the system 270 may select responder 2912 to proceed directly to the emergency event 2920 along the route 2926 based on a calculated or estimated response time of 4 minutes with medical equipment 2922 (i.e., the system 270 may estimate that responder 2912 can traverse the route 2926 to the emergency event 2920 to reach the victim in 4 minutes). In making these selections, the system 270 may compare routes with and without medical equipment. For example, if the responder 2910 collects medical equipment 2921, the system may estimate a response time of 6 min along the route 2927. As this time exceeds the 4 min time for responder 2912 along the route 2926, the system 270 may select the responder 2912 to obtain equipment rather than the responder 2910. In an implementation, the system 270 may estimate multiple potential routes and multiple route/ responder/equipment combinations to arrive at the priority ranking in table 2930. The route evaluations may account for impediments or delays indicated by the mapping information (e.g., closed roads, closed sidewalks, traffic delays, etc.) and/or may account for availability information for the medical equipment (e.g., days and/or hours of availability and/or public, private, or mobile designations). The route evaluations may also account for the desired type of medical equipment based on the nature of the emergency event (e.g., an AED may be desired for a cardiac arrest whereas a trauma kit may be desired for laceration wound). Although the example in FIG. 29A shows two selected responders out of a group of three ranked responders, these quantities are examples only and the system 270 may select one or more first responders with one or more types of medical equipment along with one or more second responders. For example, a drug overdose may require an AED and a drug overdose kit and the system 270 may designate one responder to obtain both types of equipment or select two responders, one to obtain the AED and one to obtain the drug overdose kit. Based on the selections of the responder(s) that should acquire the medical equipment and the responder(s) that should proceed to the emergency event without acquiring medical equipment, the management system 270 may send instructions to the mobile computing devices associated with the various responders. The instructions may indicate the selection along with navigable route information based on the selection. In this manner, the system 270 may optimize the response times for the emergency event.

Figure 29B:
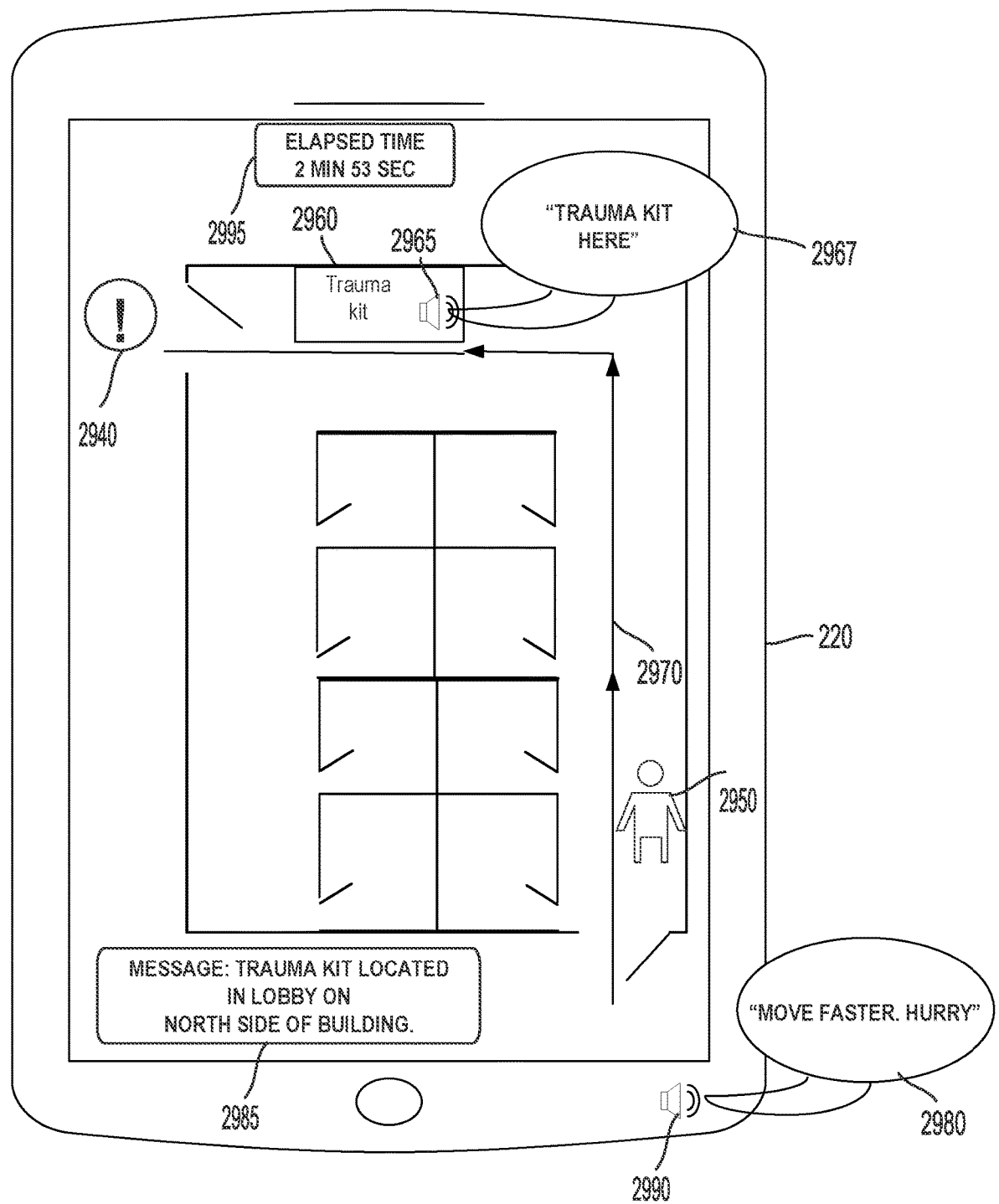
FIG. 29B shows examples of real-time responder guidance from the medical equipment and/or the software application.

Referring to FIG. 29B, examples of real-time responder guidance from the medical equipment and/or the software application are shown. In an implementation, the system 270 may track the responders in real-time and provide announcements and/or guidance. For example, as the first responder 2950 is heading to the medical equipment, shown here, for example, as a trauma kit 2960, t, the system 270 tracks their location, travel time, and distance from the emergency event 2940 and the from the medical equipment. In an implementation, the system 270 may communicate with the medical equipment 230 and cause the medical equipment 230 to activate an announcement system when the system 270 detects that the responder is within a pre-determined distance of the medical equipment 230, e.g. 10, 50, 100, or 200 yards. For example, the announcement system may include beacon light and/or an audible annunciator alarm on the medical equipment 230 or on a storage unit for the medical equipment 230. For example, trauma kit 2960 may include a speaker 2965 that may provide the audible annunciator alarm message 2967 of "TRAUMA KIT HERE" one or more times.

As the responder 2950 approaches the equipment location, the software application 225 may provide textual location detail that is location sensitive. For instance, if a trauma kit is mounted in a cabinet in the lobby on the north side of an office building, and the responder is approaching the building from a street on the south side of the building, then the software application 225 provide a location text message 2985 and/or audio message. For example, the location text message may be "trauma kit located in lobby on north side of building." Location information may shift from geo-positional (e.g. degrees/minutes/seconds and/or "turn left"/"turn right") to landmark-based (e.g. an directional text and/or audio message such as "Go to next corner of 1st Ave. and Maple St. and enter glass doors of lobby of ACME Corporation. The security guard has access to trauma kit.") The mobile device 220 may include a speaker 2990 configured to provide audio messages from the software application 225 and/or the management system 270.

In an implementation, the system 270 may track the responder's approach to the medical equipment 230 and/or the victim and if the first responder is taking too long relative to a desired response time to get to equipment 230 and/or get to the victim, the software application 225 may output either a response time warning text and/or audio message 2980. For example, the message may be "Move faster! Hurry!" In an implementation, the software application 225 may provide an indication 2995 of the elapsed time since the responder accepted the emergency assignment.

In an implementation, the system 270 may direct a responder to proceed directly to a victim without equipment based on distance and/or travel time. For example, the system 270 may identify only one responder within a vicinity of the emergency event. The system 270 may calculate or estimate a shortest response time including picking up the medical equipment 230 and getting to the victim, compare this time to a predefined threshold, and determine that the time exceeds the predefined threshold (e.g. 2, 5, 10, or 15 minutes). Additionally, the system 270 may calculate or estimate a response time of the responder going directly to the victim, compare this response time to a predefined fraction of the time acquire the medical equipment (e.g. 50%), and determine that this response time is less than the predefined fraction. In this case, the software application 225 may provide navigation instructions to that sole responder that directs them straight to the victim without getting the medical equipment to provide potentially life-saving treatment. In an implementation, the system 270 may also alert the emergency dispatch service 125 and/or the EMS agency 130 of the lack of equipment so that the dispatch and/or the agency can provide this equipment. For example, the EMS team provide a defibrillator to deliver one or more defibrillation shocks while the sole responder continues chest compressions and/or other CPR maneuvers.

The systems and methods described herein may include and enable integration of the functions and capabilities of the management system 270 with functions and capabilities of an emergency medical services (EMS) agency 130. Integration of functions and capabilities may include interactions between the management system 270 and the EMS agency 130 and/or coordination of activities between the management system 270 and the EMS agency 130. In response to the occurrence of an emergency event, the emergency dispatch service 125 may receive notification of the emergency event. For example, a victim, bystander, or responder may call an emergency services number such as 9-1-1 in the United States or 1-1-2 in the European Union, for example. The emergency dispatch service 125 may be a public service answering point (PSAP) designated to automatically receive emergency notifications. The emergency dispatch service 125 may provide the emergency event information 150 to the EMS agency 130 and to the management system 270. The emergency event information 150 may include the location of the emergency event. The management system 270 may further receive EMS agency information from the EMS agency 130. The EMS agency information may include one or more of an estimated time of arrival of personnel from the EMS agency at the emergency event, instructions for the responder from the EMS agency, a recommendation of a particular item of registered medical equipment and/or a type of medical equipment for the responder to acquire and bring to the emergency event, a recommendation of a responder training level and/or responder proficiency level, and/or combinations thereof.

Instructions from the EMS agency may include treatment instructions and/or patient information. Based on the EMS agency information and the location of the emergency event, the management system 270 may select one or more registered responders. Additionally, the management system 270 may select one or more items of registered medical equipment based on the EMS agency information and the location of the emergency event. The management system 270 may provide the location of the emergency event and the medical equipment location information to the responder selected based at least in part on the EMS agency information. Further, the medical equipment location information may correspond to the registered medical equipment selected based at least in part on the EMS agency information. In an implementation, the management system 270 and the software application 225 may provide an activity log 780 to the one or more computing devices associated with registered responders. The activity log 780 may include time-stamped information about activities and locations of one or more responders. In an implementation, the activity log 780 may further include time-stamped information for the EMS agency response to the emergency event. In an implementation, the management system 270 and the software application 225 may provide an interactive map 410 to the one or more computing devices associated with registered responders. The interactive map 410 may include one or more location indicators 1930 for dispatched vehicle(s) and/or personnel from the EMS agency responding to the emergency event. In an implementation, the EMS agency 130 and/or the management system 270 may track the location of the dispatched vehicle(s) and/or personnel. The EMS agency 130 may provide the tracked location information to the management system 270. The management system 270 and the software application 225 may provide the tracked location information for the dispatched vehicle(s) and/or personnel from the EMS agency 130 at the interactive map 410. In an implementation, the management system 270 may filter responder registration information in the responder database based on the EMS agency information to identify one or more computing devices and associated responders located closer to the emergency event than the EMS agency and/or than a current location of any dispatched vehicle(s) and/or personnel. The location of the one or more computing devices may be a current tracked location or a registered location. The registered location may indicate a likely location of the computing device based on responder activities. For example, the responder may indicate at registration that they usually located at a home or work address or may provide hours and/or days of the week at this location. The management system 270 may select this filtered group of computing devices to receive the location of the emergency event and/or the emergency assistance request. In an implementation, the registered responder may provide a confirmation to the software application 225 that they have acquired a particular item of registered medical equipment. The management system 270 may receive this confirmation and may forward the confirmation to the EMS agency 130. The management system 270 may further provide equipment information to the EMS agency for the acquired item of equipment and/or may provide responder information for the responder that acquired the particular item of medical equipment. In an implementation, the management system 270 may receive a notification from the EMS agency 130 that at least one dispatched vehicle from the EMS agency arrived at the emergency event. Alternatively or additionally, the management system 270 may track the location of the dispatched vehicle and determine that the vehicle has arrived at the emergency event. In response to the notification and/or determination that the EMS vehicle has arrived at the emergency event, the management system 270 and the software application 225 may provide an end of event screen 1310 to the one or more computing devices corresponding to the one or more registered responders associated with the emergency event. The end of event screen 1310 may provide an exit control for the responder to confirm that they are exiting the event and are therefore available for a different event. The software application 225 may provide the end of event screen 1310 to more than one responder associated with the emergency event including responders that may still be en route to the event. In an implementation, the EMS agency 130 may provide a patient care record to the management system 270. The management system 270 may append stored information about the response to the event (e.g., responder information, equipment information, time stamped activities, etc.) and return the appended patient care report to the EMS agency 130. The stored information about the response may be an event response report. Additionally or alternatively, in response to the selection of the exit control, the management system 270 may store and/or provide the event response report to the EMS agency 130. The event response report may be in a format that enables the EMS agency 130 to append the report to the patient care report.

Referring to FIG. 30A, a schematic diagram of an example of computing device components is shown. For example, the mobile computing device 220 may include the processor 1010*a*, the memory 1020*a*, the input device 1030*a*, the output device 1040*a*, the location module 1050*a*, and the transceiver 1070*a*. The remote computing device 240 may also include one or more of the components shown in FIG. 30A. The components 1010*a*, 1020*a*, 1030*a*, 1040*a*, 1050*a*, and 1070*a* are communicatively coupled (directly and/or indirectly) to each other for bi-directional communication. Although shown as separate entities in FIG. 30A, two or more of the components 1010*a*, 1020*a*, 1030*a*, 1040*a*, 1050*a*, and 1070*a* may be combined into one or more discrete components and/or may be part of the processor 1010*a*. The processor 1010*a* and the memory 1020*a* may include and/or be coupled to associated circuitry in order to perform the functions described herein. A quantity of each component shown in FIG. 30A is an example only and other quantities of each, or any, component could be used.

Figure 30B:
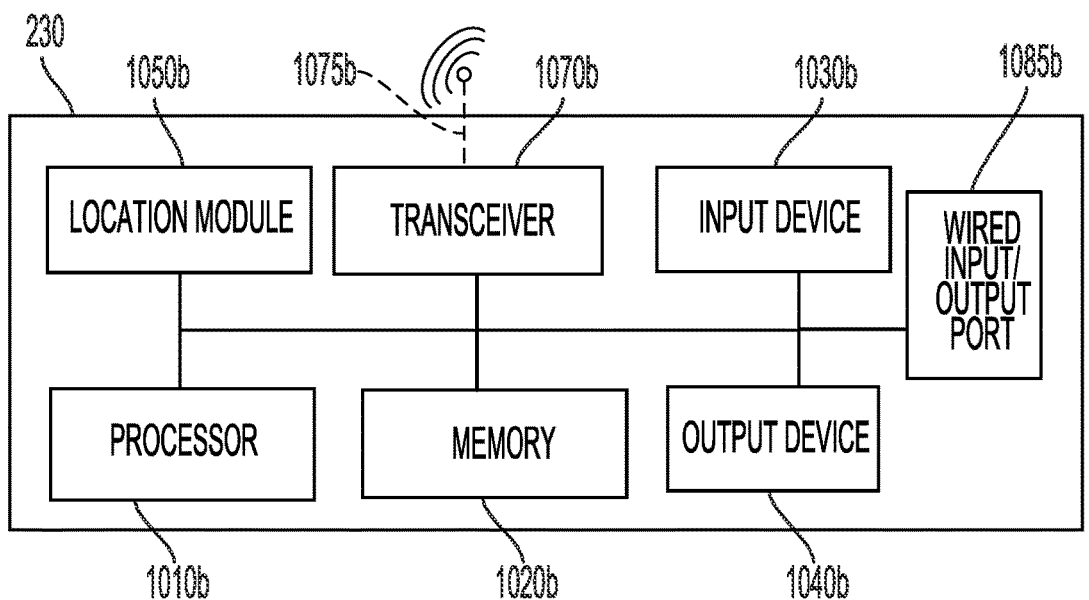
FIG. 30B shows a schematic diagram of an example of medical equipment components.

Referring to FIG. 30B, a schematic diagram of an example of medical equipment components is shown. For example, the medical equipment 230 may include the processor 1010*b*, the memory 1020*b*, the input device 1030*b*, the output device 1040*b*, the location module 1050*b*, and the transceiver 1070*b*. A quantity of each component shown in FIG. 30A is an example only and other quantities of each, or any, component could be used. The components 1010*b*, 1020*b*, 1030*b*, 1040*b*, 1050*b*, and 1070*b* are communicatively coupled (directly and/or indirectly) to each other for bi-directional communication. Although shown as separate entities in FIG. 30B, two or more of the components 1010*b*, 1020*b*, 1030*b*, 1040*b*, 1050*b*, and 1070*b* may be combined into one or more discrete components and/or may be part of the processor 1010*b*. The processor 1010*b* and the memory 1020*b* may include and/or be coupled to associated circuitry in order to perform the functions described herein. A quantity of each component shown in FIG. 30B is an example only and other quantities of each, or any, component could be used.

The processors 1010*a* and 1010*b* are each one or more physical processors (i.e., an integrated circuit configured to execute operations on the mobile computing device 220, the remote computing device 240, or the medical equipment 230 as specified by software and/or firmware). Each of the processors 1010a, 1010b may be an intelligent hardware device, e.g., a central processing unit (CPU), one or more microprocessors, a controller or microcontroller, an application specific integrated circuit (ASIC), digital signal processor (DSP), or other programmable logic device, a state machine, discrete gate or transistor logic, discrete hardware components, or any combination thereof designed to perform the functions described herein and operable to carry out instructions on the mobile computing device 220, the remote computing device 240, or the medical equipment 230. Each of the processors 1010a, 1010b may utilize various architectures including but not limited to a complex instruction set computer (CISC) processor, a reduced instruction set computer (RISC) processor, or a minimal instruction set computer (MISC). In various implementations, each of the processors 1010a, 1010b may be a single threaded or a multi-threaded processor. Each of the processors 1010a, 1010b may be one or more processors and may be implemented as a combination of computing devices (e.g., a combination of DSP and a microprocessor, a plurality of microprocessors, one or more microprocessors in conjunction with a DSP core, or any other such configuration). Each of the processors 1010a, 1010b may include multiple separate physical entities that may be distributed in the mobile computing device 220, the remote computing device 240, or in the medical equipment 230. Each of the processors 1010a, 1010b is configured to execute processor-readable, processor-executable software code containing one or more instructions or code for controlling the processor 1010a, 1010b to perform the functions as described herein.

The processors 1010a, 1010b are operably coupled, respectively, to the memory 1020a, 1020b. The memory 1020a, 1020b refers generally to any type of computer storage medium, including but not limited to RAM, ROM, FLASH, disc drives, fuse devices, and portable storage media, such as Universal Serial Bus (USB) flash drives, etc. The USB flash drives can store operating systems and other applications. The USB flash drives can include input/output components, such as a wireless transmitter and/or USB connector that can be inserted into a USB port of another computing device. The memory 1020a, 1020b may be long term, short term, or other memory associated with the mobile computing device 220, the remote computing device 240, or the medical equipment 230 and is not to be limited to any particular type of memory or number of memories, or type of media upon which memory is stored. The memory 1020a, 1020b includes a non-transitory processor-readable storage medium (or media) that stores the processor-readable, processor-executable software code.

The input devices 1030a, 1030b may include one or more of a keyboard, a microphone, and a mouse, joystick, trackball, or other pointing device. The processors 1010a and 1010b may, respectively, control the input devices 1030a and 1030b to capture user input. The input device 1030a may further include the camera 1080 and/or the asset tag reader 1090. For example, the asset tag reader 1090 may include an RFID tag reader and/or a barcode scanner.

The output devices 1040a, 1040b may be a one or more of a display, a speaker (e.g., the speaker 2966 or 2990), and a haptic device. The display may provide a graphical user interface (GUI). The display may be, for example, but not limited to, a liquid crystal display (LCD) and/or a light emitting diode (LED) display. The processors 1010a and 1010b may control, respectively, the output devices 1040a and 1040b to provide one or more of visible information, audible information, haptic information, numerical information, textual information, and graphical information.

In an implementation, the input device 1030a and the output device 1040a and/or the input device 1030b and the output device 1040b may be combined as an input/output device capable of capturing user input. For example, the input/output device may be a touchscreen.

The location module 1050a is illustrated separately from the processor 1010a for clarity but may be part of processor 1010a or may be implemented in the processor 1010a based on instructions in software stored in memory 1020a and implemented by processor 1010a. Similarly, the location module 1050b is illustrated separately from the processor 1010b for clarity but may be part of processor 1010b or may be implemented in the processor 1010b based on instructions in software stored in memory 1020b and implemented by processor 1010b. The location modules 1050a, 1050b can, but need not necessarily, include and/or be incorporated into, for example, one or more microprocessors, embedded processors, controllers, application specific integrated circuits (ASICs), digital signal processors (DSPs), etc. The location module 1050a is configured to determine a location of the mobile computing device 220 and the location module 1050b is configured to determine a location of the medical equipment 230.

In an implementation, the location modules 1050a, 1050b may determine locations based on signals from satellite positioning system (SPS) satellites 290 and/or terrestrial radio transmitters (e.g., outdoor radio transmitters 296 and/or indoor radio transmitters 295). The SPS satellites 290 include suitable logic, circuitry, and code to generate and send radio-frequency (RF) SPS signals that may be received at the mobile computing device 220 and/or the medical equipment 230 for use in determining a satellite positioning system based location of the mobile computing device 220 and/or the medical equipment 230. The SPS may include such systems as the Global Positioning System (GPS), Galileo, Glonass, Compass, Quasi-Zenith Satellite System (QZSS) over Japan, Indian Regional Navigational Satellite System (IRNSS) over India, Beidou over China, etc., and/or various augmentation systems (e.g., a Satellite Based Augmentation System (SBAS)) that may be associated with or otherwise enabled for use with one or more global and/or regional navigation satellite systems. As used herein, an SPS may include any combination of one or more global and/or regional navigation satellite systems and/or augmentation systems, and SPS signals may include SPS, SPS-like, and/or other signals associated with such one or more SPS. The terrestrial radio transmitters may include, for example, but not limited to, Wi-Fi®/WLAN access points, Worldwide Interoperability for Microwave Access (WiMAX) nodes, femtocells, communications network base stations and other cellular wireless nodes, a Bluetooth® or other similarly short-ranged wireless node, combinations thereof, and so forth. The indoor radio transmitters 295 may be located internal to the structure 205, external to the structure 205, or on a border of the structure 205 (e.g., partially interior and partially exterior).

In an implementation, the SPS-based location may be a geo-location for the mobile computing device 220 and/or the medical equipment 230. The geolocation may include a two-dimensional location in a global coordinate system (e.g., a latitude and longitude or other earth centered coordinates). The geolocation may further include an elevation (i.e., a three-dimensional location in a global coordinate system). The elevation may be a SPS-based elevation and/or may be an elevation determined based on an indicator of elevation such as barometric pressure.

In an implementation, the location modules 1050a and/or 1050b may determine an indoor location for the mobile computing device 220 and/or the medical equipment 230. Satellite positioning systems (SPS), such as, for example, global positioning systems (GPS) have enabled location determination for computing devices in outdoor environments. However, satellite signals may not always be reliably received and/or acquired in an indoor environment. Therefore, location determination techniques other than SPS-based positioning may be employed to enable indoor position estimation and related navigation services. For example, the location modules 1050a, 1050b may determine the indoor location by measuring ranges to three or more terrestrial radio transmitters including, for example, the radio transmitters 295 and/or 296. In an implementation, the location information may include indoor mapping information that includes indoor locations of medical equipment.

In an implementation, the location module 1050b may transmit the location of the medical equipment to the management system 270, the registration system 260, and/or the mobile computing device 220. In this manner, the medical equipment 230 may self-report its location. In an implementation, the location module 1050a may transmit the location of the mobile computing device 220 to the management system 270 and/or the registration system 210.

The location of the radio transmitter 295 may be a predetermined location relative to indoor mapping information for the structure 205. The location of the radio transmitter 295 and the indoor mapping information for the structure 205 may be stored in a positioning database, for example, at one or more positioning servers. The location modules 1050a and/or 1050b may access the indoor location of the radio transmitter 295 and/or the indoor mapping information via the network(s) 250. The location modules 1050a and/or 1050b may determine measured ranges to the three or more terrestrial radio transmitters, for example, by obtaining a media access control (MAC) address from signals received from such radio transmitters and measuring one or more characteristics of signals received from such radio transmitters such as, for example, a signal strength (e.g., a received signal strength indication (RSSI)) and/or a propagation time (e.g., a round-trip time (RTT)) for signals exchanged with various radio transmitters. The positioning database may identify the indoor location of a particular radio transmitter based on, for example, the MAC address.

The indoor mapping information may include a digital electronic map that includes navigation and routing information and/or location information for indoor features such as doors, hallways, entry ways, walls, etc., points of interest such as bathrooms, conference room names, stores, offices, etc. The indoor features may further include medical equipment locations. Such a digital electronic map may be stored at the positioning server to be accessible by the location module 1050a, 1050b through selection of an Internet-based universal resource locator (URL), for example. In an implementation, the processor 1010a and/or 1010b may control the output device 1040a and/or 1040b to display the digital electronic map. The location module 1050a, 1050b may determine the indoor location of the mobile computing device 220 or the medical equipment 230 relative to the indoor mapping information. In an implementation, the location module 1050a, 1050b may convert the indoor location to a geolocation based on a correlation between the indoor locations and earth coordinates.

The transceivers 1070a, 1070b can send and receive wireless signals via the antennas 1075a, 1075b over one or more wireless networks, for example, the network(s) 250 in FIG. 1. Although shown as single transceivers and antennas in FIGS. 30A and 30B, the transceiver 1070a and/or 1070b and the antenna 1075a and/or 1075b may include multiple transceivers and antennas, for example, to support multiple communication standards such as Wi-Fi®, Code Division Multiple Access (CDMA), Wideband CDMA (WCDMA), Long Term Evolution (LTE), Bluetooth, etc. The transceivers 1070a, 1070b may also be configured to receive SPS signals (e.g., from the SPS satellites 290 in FIG. 1) used to determine location information. The transceivers 1070a, 1070b may be further configured to enable the mobile computing device 220 and/or the medical equipment 230 to communicate and exchange information, either directly or indirectly with other communications network entities, including but not limited to, other computing devices and/or other medical equipment.

The servers 212, 216, 262, 272, and/or 282 may include or contribute to a cloud storage system. The cloud storage system may reside on one or more servers in a cloud server network. The one or more servers may be communicatively coupled in order to provide cloud computing and cloud storage services to the mobile computing device 220 and/or the remote computing device 240 via the network(s) 250. Cloud computing allows a user of the computing devices 220 and/or 240 to perform computing tasks where data, applications, and even complete virtualized computing systems are accessed via the network(s) 250. The network of servers and connections used to provide the cloud computing service is generally referred to as "the cloud." Cloud storage provides an abstraction for physical storage devices. Cloud storage generally involves delivering data storage as a service, often billed on a usage basis. That is, cloud storage allows users to store and access data files somewhere in "the cloud," without knowing the details of where files are stored or having to manage the physical storage devices. In the cloud storage system, capacity can be available on demand and files can be made available on a global basis.

The software application 225, the management system 270, the registration system 260 and the database 280 described herein can be implemented in digital electronic circuitry, or in computer hardware, firmware, software, or in combinations of them. Firmware and/or software can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program, including the software application 225, is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example, semiconductor memory devices, such as EPROM, 5PROM, and flash memory devices; magnetic disks such as internal hard disks and removable disks; magneto-optical disks; and CD-ROM and DVD-ROM disks.

The computing devices described herein may include, or be operatively coupled to communicate with, one or more mass storage devices for storing data files; such devices may include magnetic disks, such as internal hard disks and removable disks, magneto-optical disks, and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Components, functional or otherwise, shown in the figures and/or discussed herein as being connected or communicating with each other are communicatively coupled. That is, they may be directly or indirectly connected to enable communication between them. Features implementing functions may be physically located at various locations, including being distributed such that portions of functions are implemented at different physical locations.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., 1, 1B, A2C, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify applications presented by the present disclosure. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

What is claimed is:

1. A system for remote communications with mobile communication devices for managing responders to acquire medical equipment and to respond to an emergency medical event, the system comprising:
a first mobile computing device associated with a first registered responder;
a second mobile computing device associated with a second registered responder;
a computer aided dispatch (CAD) system; and
a medical equipment and responder management system communicatively coupled to the first and second mobile computing devices and to the CAD, the management system configured to:
receive emergency medical event information from the CAD, the emergency medical event information comprising an emergency medical event location,
retrieve medical equipment information stored in a medical equipment database, the medical equipment information comprising medical equipment locations,
receive a current first responder location from the first mobile computing device,
send the emergency medical event location and the medical equipment locations to the first mobile computing device,
generate an activity log for the emergency medical event, the activity log comprising first responder status information based at least in part on the current first responder location, the emergency medical event location, and the medical equipment locations,
send the activity log to the first mobile computing device,
send the emergency medical event location and the medical equipment locations to the second mobile computing device,
receive a current second responder location from the second mobile computing device,
update the activity log with second responder status information based at least in part on the current second responder location, the emergency medical event location, and the medical equipment locations, and
send the updated activity log to the first and the second mobile computing devices.

2. The system of claim 1 wherein the first and second responder status information comprises time stamped activity information for the first and second registered responders.

3. The system of claim 1 wherein the activity log comprises a timer that indicates an elapsed time between a current time and a time of receipt of the emergency medical event information from the CAD at the management system.

4. The system of claim 1, wherein the first and second responder status information comprises a navigation status and an equipment acquisition status.

5. The system of claim 4 wherein the navigation status comprises one of:

(a) en route to an item of medical equipment in the medical equipment database,
(b) arrived at the item of medical equipment in the medical equipment database,
(c) en route to the emergency medical event, and
(d) arrived at the emergency medical event.

6. The system of claim 4, wherein the equipment acquisition status comprises one of:
(a) acquired an item of medical equipment in the medical equipment database, and
(b) proceeding to the emergency medical event without acquiring any medical equipment in the medical equipment database.

7. The system of claim 1, wherein the management system is configured to:
retrieve registered responder information stored in a responder database,
retrieve user selected tracking permission settings from the responder database for the first and second responders,
automatically track locations for the first and second mobile computing devices in response to the user selected tracking permission settings, and
update the first and second responder statuses in the activity log at the first and second mobile computing devices based on the automatically tracked locations.

8. The system of claim 7, wherein the management system is configured to:
provide interactive map information at the first and second mobile computing devices, wherein the interactive map information comprises:
the automatically tracked locations of the first and second mobile computing devices,
the emergency medical event location, and
the medical equipment location information.

9. The system of claim 8, wherein the management system is configured to:
filter equipment registration information in the medical equipment database to identify a set of medical equipment located within a vicinity of the emergency medical event location, and
send the medical equipment location information for only the set of medical equipment located within the vicinity of the emergency medical event location to the first mobile computing device.

10. The system of claim 9, wherein the vicinity of the emergency medical event location corresponds to a distance of 0-400 meters from the emergency medical event.

11. The system of claim 9, wherein the vicinity of the emergency medical event location corresponds to a distance within a pre-determined travel time from the emergency medical event based on a speed associated with a responder mode of transport.

12. The system of claim 8, wherein the management system is configured to:
estimate a plurality of first travel times for the first and second responders between the automatically tracked locations of the first and second mobile computing devices and the medical equipment locations,
estimate a plurality of second travel times for the first and second responders between the medical equipment locations and the emergency medical event location,
send an equipment acquisition recommendation configured for display on the interactive map based at least in part on the plurality of first and second travel times.

13. The system of claim 12, wherein the management system is configured to:

retrieve a mode of transport stored in the responder database for each of the first and second responders, and estimate the first and second travel times based on an estimated speed for the mode of transport, wherein the mode of transport comprises walking or driving.

14. The system of claim 12, wherein the equipment acquisition recommendation comprises an indication of a navigable routes between the emergency medical event location, the automatically tracked locations of the first and second mobile computing devices, and the medical equipment locations for a set of medical equipment located within a vicinity of the emergency medical event location.

15. The system of claim 14, wherein the navigable routes comprise one or more of graphic or text representations of turn-by-turn directions.

16. The system of claim 12, wherein the management system is configured to estimate the first and second travel times based on one or more interior maps corresponding to one or more facilities storing medical equipment in the medical equipment database.

17. The system of claim 16, wherein the one or more interior maps are three-dimensional maps that include multiple stories and access routes comprising at least one of stairs and elevators.

18. The system of claim 16, wherein the estimated first and second travel times account for a distance from a facility entryway to a medical equipment storage location.

19. The system of claim 12, wherein the management system is configured to:

estimate a plurality of third travel times for the first and second responders between the automatically tracked locations of the first and second mobile computing devices and the emergency medical event location, rank the first and second responders according to the third travel times and a sum of the first and second travel times, select one of the first or second responders to acquire the medical equipment based on the rank, select another one of the first or second responders to proceed to the emergency medical event location without acquiring the medical equipment, and send instructions to the first and second mobile computing devices based on the selections.

20. The system of claim 8, wherein one or more of the activity log and the interactive map include an indication of medical equipment acquisition by the first and/or second responder.

21. The system of claim 1, wherein the medical equipment database comprises registration information for one or more of automated external defibrillators and trauma kits.

22. The system of claim 21, wherein the registration information comprises equipment status information and the medical equipment information.

23. The system of claim 1, wherein the management system is configured to:

send the location of the emergency medical event to a plurality of computing devices associated with registered responders and included in a responder database, receive availability indications from one or more computing devices, wherein a respective computing device has self-determined itself to be located within a vicinity of the location of the emergency medical event and wherein the one or more computing devices comprise the first and second mobile computing devices, and send the emergency medical event location to the first and second mobile computing devices in response to the received availability indications.

24. The system of claim 23, wherein the responder database comprises responder training information indicative of a proficiency level for a category of emergency medical event, and wherein the management system is configured to:

determine the category of the emergency medical event based on the emergency medical event information received from the CAD, and send the one or more computing devices the emergency medical event location based on the proficiency level of an associated responder and the category of the emergency medical event.

* * * * *